(12) United States Patent
Boehringer et al.

(10) Patent No.: US 6,861,440 B2
(45) Date of Patent: Mar. 1, 2005

(54) DPP IV INHIBITORS

(75) Inventors: Markus Boehringer, Moehlin (CH); Daniel Hunziker, Moehlin (CH); Holger Kuehne, Grenzach-Wyhlen (DE); Bernd Michael Loeffler, Oberrimsingen (DE); Ramakanth Sarabu, Towaco, NJ (US); Hans Peter Wessel, Schliengen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/269,519

(22) Filed: Oct. 14, 2002

(65) Prior Publication Data

US 2003/0130281 A1 Jul. 10, 2003

(30) Foreign Application Priority Data

Oct. 26, 2001 (EP) .......................... 01125338
Aug. 21, 2002 (EP) .......................... 02018227

(51) Int. Cl.[7] .................. C07D 403/12; C07D 413/12; A61K 31/4178; A61K 31/422
(52) U.S. Cl. .................. 514/341; 514/374; 546/274.1; 548/236
(58) Field of Search .................. 546/274.1; 548/236; 514/374, 341

(56) References Cited

U.S. PATENT DOCUMENTS

| | | |
|---|---|---|
| 5,455,351 A | 10/1995 | Kempf et al. |
| 6,011,115 A | 1/2000 | Miharu et al. |
| 6,110,949 A | 8/2000 | Villhauer |
| 6,124,305 A | 9/2000 | Villhauer |

FOREIGN PATENT DOCUMENTS

| | | |
|---|---|---|
| DE | 19616486 C2 | 10/1997 |
| DE | 19616486 A1 | 10/1997 |
| DE | 19834591 | 2/2000 |
| WO | WO 95/01976 | 1/1995 |
| WO | WO 96/10018 | 4/1996 |
| WO | WO 98/19998 | 5/1998 |
| WO | WO 99/38501 A3 | 8/1999 |
| WO | WO 99/38501 A2 | 8/1999 |
| WO | WO 00/08002 | 2/2000 |
| WO | WO 00/34241 | 6/2000 |
| WO | WO 01/19805 | 3/2001 |
| WO | WO 0134594 | 5/2001 |
| WO | WO 01/40180 | 6/2001 |
| WO | WO 01/55105 | 8/2001 |
| WO | WO 0162266 | 8/2001 |
| WO | WO 0230890 | 4/2002 |

OTHER PUBLICATIONS

Schunack et al., Z. Naturforschung, 42b, pp. 238–242 (1987).
Lipp et al., Eur. J. Med. Chem., 30, pp. 219–225 (1995).
Horne et al., Heterocycles, 39, pp. 139–153, (1994).
Francis et al., Tetrahedron Letters, 28, pp. 5133–5136 (1987).
Ali et al., Pak. J. Sci. Ind. Res., 36, pp. 502–510 (1993).
Weintraub, P.M., J. Med. Chem, 15, pp. 419–420 (1972).
Goto et al., Chem. Pharm. Bull., 19, pp. 2050–2057 (1971).
Golfier et al., J. Heterocycl. Chem., 10, pp. 989–991 (1973).
Singh et al., Ind. J. Chem., 22B, pp. 1177–1178 (1983).
Carrera et al., Synlett, 1, p. 93–94 (1994).
Agarwal et al., Synth. Commun., 23, pp. 1101–1110 (1993).
Qizhuang et al., J. Med. Chem., 32, pp. 478–486 (1989).
Freedman et al., J. Heterocycl. Chem., 27, pp. 343–346 (1990).
Collins et al., J. Med. Chem., 41, pp. 5037–5054 (1998).
Novartis AG, Expert Opinion on Therapeutic Patents, Ashley Publications, GB, vol. 10, No. 12, pp. 1937–1942 (2000).

*Primary Examiner*—Joseph K. McKane
*Assistant Examiner*—Rebecca Anderson
(74) *Attorney, Agent, or Firm*—George W. Johnston; Dennis P. Tramaloni; Samuel H. Megerditchian

(57) ABSTRACT

The present invention relates to compounds of formula (I)

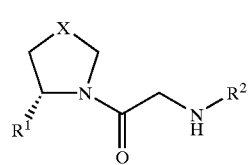

(I)

wherein $R^1$, $R^2$, and X are as defined in the description and claims, and pharmaceutically acceptable salts thereof. The compounds are useful for the treatment and/or prophylaxis of diseases which are associated with DPP IV, such as diabetes, particularly non-insulin dependent diabetes mellitus, and impaired glucose tolerance.

8 Claims, No Drawings

DPP IV INHIBITORS

BACKGROUND OF THE INVENTION

The present invention is concerned with novel pyrrolidin derivatives, their manufacture and their use as medicaments. The present invention further relates to pharmaceutically acceptable salts of these pyrrolidine compounds and pharmaceutical compositions containing these compounds.

The enzyme dipeptidyl peptidase IV (EC.3.4.14.5, abbreviated in the following as DPP-IV) is involved in the regulation of the activities of several hormones. In particular DPP-IV is degrading efficiently and rapidly glucagon like peptide 1 (GLP-1), which is one of the most potent stimulator of insulin production and secretion. Inhibiting DPP-IV would potentiate the effect of endogenous GLP-1, and lead to higher plasma insulin concentrations. In patients suffering from impaired glucose tolerance and type 2 diabetes mellitus, higher plasma insulin concentration would moderate the dangerous hyperglycaemia and accordingly reduce the risk of tissue damage. Consequently, DPP-IV inhibitors have been suggested as drug candidates for the treatment of impaired glucose tolerance and type 2 diabetes mellitus (e.g. Vilhauer, WO98/19998). Other related state of the art can be found in WO 99/38501, DE 19616486, DE 19834591, WO 01/40180, WO 01/55105, U.S. Pat. No. 6,110,949, WO 00/34241 and U.S. Pat. No. 6,011,155.

SUMMARY OF THE INVENITON

Briefly stated, novel DPP-IV inhibitors have been found that very efficiently lower plasma glucose levels. Consequently, the compounds of the present invention are useful for the treatment and/or prophylaxis of diabetes, particularly non-insulin dependent diabetes mellitus, and/or impaired glucose tolerance, as well as other conditions wherein the amplification of action of a peptide normally inactivated by DPP-IV gives a therapeutic benefit. Surprisingly, the compounds of the present invention can also be used in the treatment and/or prophylaxis of bowl disease, colitis ulcerosa, morbus crohn, obesity and/or metabolic syndrome. Unexpectedly, the compounds of the present invention exhibit improved therapeutic and pharmacological properties compared to other DPP IV inhibitors known in the art, such as e.g. in context with pharmacokinetics and bioavailability.

According to one aspect of the present invention, there is provided a compound of formula (I)

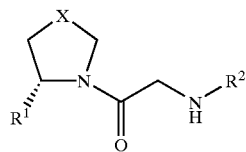

(I)

wherein
$R^1$ is H or CN,
$R^2$ is —C($R^3$,$R^4$)—(CH$_2$)$_n$—$R^5$, —C($R^3$,$R^4$)—CH$_2$—NH—$R^6$, —C($R^3$,$R^4$)—CH$_2$—O—$R^7$; or tetralinyl, tetrahydroquinolinyl or tetrahydroisoquinolinyl, which tetralinyl, tetrahydroquinolinyl or tetrahydroisoquinolinyl group can be unsubstituted or substituted with 1 to 3 substituents independently selected from the group consisting of lower-alkyl, lower-alkoxy, halogen, CN, and CF$_3$, $R^3$ is hydrogen, lower-alkyl, benzyl, hydroxybenzyl or indolylmethylene,
$R^4$ is hydrogen or lower-alkyl, or
$R^3$ and $R^4$ are bonded to each other to form a ring together with the carbon atom to which they are attached and —$R^3$—$R^4$— is —(CH$_2$)$_{2-5}$—,
$R^5$ is 5-membered heteroaryl, bi- or tricyclic heterocyclyl, or aminophenyl; which can be unsubstituted or substituted with 1 to 3 substituents independently selected from the group consisting of lower-alkyl, lower-alkoxy, halogen, CN, CF$_3$, trifluoroacetyl, thiophenyl, phenyl, heteroaryl and monocyclic heterocyclyl, which phenyl, heteroaryl or monocyclic heterocyclyl can be unsubstituted or substituted with 1 to 3 substituents independently selected from the group consisting of lower-alkyl, lower-alkoxy, benzyloxy, halogen, CF$_3$, CF$_3$—O, CN and NH—CO-lower-alkyl,
$R^6$ is a) pyridinyl or pyrimidinyl, which is substituted with 1 to 3 substituents independently selected from the group consisting of aryl and heteroaryl, which aryl or heteroaryl group can be unsubstituted or substituted with 1 to 3 substituents independently selected from the group consisting of lower-alkyl, lower-alkoxy, halogen, CN, and CF$_3$, or b) 5-membered heteroaryl or bi- or tricyclic heterocyclyl, which 5-membered heteroaryl or bi- or tricyclic heterocyclyl can be unsubstituted or substituted with 1 to 3 substituents independently selected from the group consisting of lower-alkyl, carbonyl, aryl and heteroaryl, which aryl or heteroaryl group can be unsubstituted or substituted with 1 to 3 substituents independently selected from the group consisting of lower-alkyl, lower-alkoxy, halogen, CN, and CF$_3$, and which carbonyl group can be unsubstituted or substituted with lower-alkyl, lower-alkoxy, halogen, CN, CF$_3$, aryl, or heteroaryl, which aryl or heteroaryl group can be unsubstituted or substituted with 1 to 3 substituents independently selected from the group consisting of lower-alkyl, lower-alkoxy, halogen, CN, and CF$_3$,
$R^7$ is aminophenyl, naphthyl or quinolinyl, which can be unsubstituted or substituted with 1 to 3 substituents independently selected from the group consisting of lower-alkyl, lower-alkoxy, halogen, CN and CF$_3$,
X is C($R^8$,$R^9$) or S,
$R^8$ and $R^9$ independently from each other are H or lower-alkyl,
n is 0, 1 or 2,
and pharmaceutically acceptable salts thereof.

According to another aspect of the present invention, there is provided a pharmaceutical composition comprising a compound of formula (I), or pharmaceutically acceptable salts thereof, and a pharmaceutically acceptable carrier and/or adjuvant.

According to a further aspect of the present invention, there is provided a method for treating or preventing diseases which are associated with DPP IV, comprising administering to a patient in need thereof, a therapeutically effective amount of a compound of the following formula (I).

These and other features, aspects and advantages of the present invention will become better understood with reference to the following drawings, description and claims.

DETAILED DESCRIPTION OF THE INVENTION

Unless otherwise indicated, the following definitions are set forth to illustrate and define the meaning and scope of the various terms used to describe the invention herein.

In this specification the term "lower" is used to mean a group consisting of one to seven, preferably of one to four carbon atom(s).

The term "halogen" refers to fluorine, chlorine, bromine and iodine, preferably to fluorine and chlorine.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms. Alkyl groups can optionally be substituted e.g. with halogen, hydroxy, lower-alkoxy, lower-alkoxy-carbonyl, $NH_2$, N(H, lower-alkyl) and/or N(lower-alkyl)$_2$. Unsubstituted alkyl groups are preferred.

The term "lower-alkyl", alone or in combination with other groups, refers to a branched or straight-chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the like. A lower-alkyl group may optionally have a substitution pattern as described earlier in connection with the term "alkyl". Unsubstituted lower-alkyl groups are preferred.

The term "alkoxy" refers to the group R'—O—, wherein R' is alkyl. The term "lower-alkoxy" refers to the group R'—O—, wherein R' is lower-alkyl. Examples of lower-alkoxy groups are e.g. methoxy, ethoxy, propoxy, isopropoxy, butoxy, isobutoxy and hexyloxy. Alkoxy and lower-alkoxy groups may optionally have a substitution pattern as described earlier in connection with the term "alkyl". Unsubstituted alkoxy and lower-alkoxy groups are preferred.

The term "aryl" relates to the phenyl or naphthyl group, preferably the phenyl group, which can optionally be mono- or multiply-substituted by lower-alkyl, lower-alkoxy, halogen, CN, $CF_3$, hydroxy, $NO_2$, $NH_2$, N(H, lower-alkyl), N(lower-alkyl)$_2$, carboxy, aminocarbonyl, phenyl, benzyl, phenoxy, and/or benzyloxy. Preferred substituents are lower-alkyl, lower-alkoxy, halogen, CN, and/or $CF_3$.

The term "heteroaryl" refers to an aromatic 5- or 6-membered ring which can comprise 1, 2 or 3 atoms selected from nitrogen, oxygen and/or sulphur such as furyl, pyrrolyl, pyridyl, 1,2-, 1,3- and 1,4-diazinyl, thienyl, oxazolyl, oxadiazolyl, isoxazolyl, thiazolyl, isothiazolyl or imidazolyl. A heteroaryl group may optionally have a substitution pattern as described earlier in connection with the term "aryl".

The term "5-membered heteroaryl" refers to an aromatic 5-membered ring which can comprise 1 to 4 atoms selected from nitrogen, oxygen and/or sulphur such as furyl, thienyl, pyrrolyl, imidazolyl, pyrazolyl, oxazolyl, isoxazolyl, thiazolyl, isothiazolyl, oxadiazolyl such as 1,3,4- and 1,2,4-oxadiazolyl, triazolyl or tetrazolyl. Preferred 5-membered heteroaryl groups are oxazolyl, imidazolyl, pyrazolyl, triazolyl, 1,3,4- and 1,2,4-oxadiazolyl and thiazolyl. A 5-membered heteroaryl group can optionally be substituted with lower-alkyl, lower-alkoxy, halogen, CN, $CF_3$, trifluoroacetyl, aryl, heteroaryl, and carbonyl, which carbonyl group can optionally be substituted with lower-alkyl, lower-alkoxy, halogen, CN, $CF_3$, aryl, or heteroaryl.

The term "monocyclic heterocyclyl" refers to non aromatic monocyclic heterocycles with 5 or 6 ring members, which comprise 1, 2 or 3 hetero atoms selected from nitrogen, oxygen and sulfur. Examples of suitable monocyclic heterocyclyl groups are piperidinyl and morpholinyl. A monocyclic heterocyclyl may be substituted with lower-alkyl.

The term "bi- or tricyclic heterocyclyl" refers to bicyclic or tricyclic aromatic groups comprising two or three 5- or 6-membered rings, in which one or more rings can comprise 1, 2 or 3 atoms selected from nitrogen, oxygen and/or sulphur, and which can be partially hydrogenated. Examples of bi- or tricyclic heterocyclyl groups are e.g. indolyl, aza-indolyl such as 2-, 3-, 4-, 5-, 6- or 7-aza-indolyl, indolinyl carbazolyl, benzothiophenyl, benzothiazolyl, benzooxazolyl, benzimidazolyl, 4,5,6,7-tetrahydro-thiazolo[5,4-c]pyridinyl, 4,5,6,7-tetrahydro-benzthiazolyl, 8H-indeno[1,2-d]thiazolyl and quinolinyl. Preferred bi- or tricyclic heterocyclyl groups are benzothiazolyl and 4,5,6,7-tetrahydro-thiazolo[5,4-c]pyridinyl. A bi- or tricyclic heterocyclyl group can optionally have a substitution pattern as described earlier in connection with the term "5-membered heteroaryl".

The term "pharmaceutically acceptable salts" embraces salts of the compounds of formula (I) with inorganic or organic acids such as hydrochloric acid, hydrobromic acid, nitric acid, sulphuric acid, phosphoric acid, citric acid, formic acid, maleic acid, acetic acid, fumaric acid, succinic acid, tartaric acid, methanesulphonic acid, p-toluenesulphonic acid and the like, which are non toxic to living organisms. Preferred salts with acids are formates, maleates, citrates, hydrochlorides, hydrobromides and methanesulfonic acid salts.

The term "leaving group" relates to a group which is removed or replaced during a reaction. Examples of leaving groups are halogen, mesylate and tosylate.

In detail, the present invention relates to compounds of formula (I)

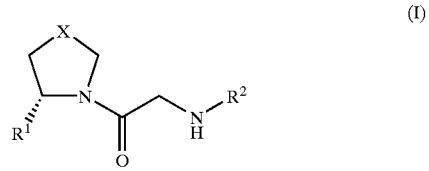

(I)

wherein
R$^1$ is H or CN,
R$^2$ is —C(R$^3$,R$^4$)—(CH$_2$)$_n$—R$^5$, —C(R$^3$,R$^4$)—CH$_2$—NH—R$^6$, —C(R$^3$,R$^4$)—CH$_2$—O—R$^7$; or tetralinyl, tetrahydroquinolinyl or tetrahydroisoquinolinyl, which tetralinyl, tetrahydroquinolinyl or tetrahydroisoquinolinyl group can optionally be substituted with 1 to 3 substituents independently selected from the group consisting of lower-alkyl, lower-alkoxy, halogen, CN, and CF$_3$,
R$^3$ is hydrogen, lower-alkyl, benzyl, hydroxybenzyl or indolylmethylene,
R$^4$ is hydrogen or lower-alkyl, or
R$^3$ and R$^4$ are bonded to each other to form a ring together with the carbon atom to which they are attached and —R$^3$—R$^4$— is —(CH$_2$)$_{2-5}$—,
R$^5$ is 5-membered heteroaryl, bi- or tricyclic heterocyclyl, or aminophenyl; optionally substituted with 1 to 3 substituents independently selected from the group consisting of lower-alkyl, lower-alkoxy, halogen, CN, CF$_3$, trifluoroacetyl, thiophenyl, phenyl, heteroaryl and monocyclic heterocyclyl, which phenyl, heteroaryl or monocyclic heterocyclyl can optionally be substituted with 1 to 3 substituents independently selected from the group consisting of lower-alkyl, lower-alkoxy, benzyloxy, halogen, CF$_3$, CF$_3$—O, CN and NH—CO— lower-alkyl, R$^6$ is a) pyridinyl or pyrimidinyl, which is substituted with 1 to 3 substituents independently selected from the group consisting of aryl and heteroaryl, which aryl or heteroaryl group can optionally be substituted with 1 to 3 substituents independently selected from the group consisting of lower-alkyl, lower-alkoxy, halogen, CN, and CF$_3$, or b) 5-membered heteroaryl or bi- or tricyclic heterocyclyl, which 5-membered heteroaryl or bi- or tricyclic heterocyclyl can optionally be substituted with 1 to 3 substituents independently selected from the group consisting of lower-alkyl, carbonyl, aryl and heteroaryl, which aryl or heteroaryl group can optionally be substituted with 1 to 3 substituents independently selected from the group consisting of lower-alkyl, lower-alkoxy, halogen, CN, and CF$_3$, and which carbonyl group can optionally be substituted with lower-alkyl, lower-alkoxy, halogen, CN, CF$_3$, aryl, or heteroaryl, which aryl or heteroaryl group can optionally be substituted with 1 to 3 substituents independently selected from the group consisting of lower-alkyl, lower-alkoxy, halogen, CN, and CF$_3$, R$^7$ is aminophenyl, naphthyl or quinolinyl, optionally substituted with 1 to 3 substituents independently selected from the group consisting of lower-alkyl) lower-alkoxy, halogen, CN and CF$_3$, X is C(R$^8$,R$^9$) or S, R$^8$ and R$^9$ independently from each other are H or lower-alkyl, n is 0, 1 or 2, and pharmaceutically acceptable salts thereof.

In a preferred embodiment, the present invention relates to compounds of formula (I), wherein R$^1$ is H or CN, R$^2$ is —C(R$^3$,R$^4$)—CH$_2$—R$^5$, —C(R$^3$,R$^4$)—CH$_2$—NH—R$^6$, —C(R$^3$,R$^4$)—CH$_2$—O—R$^7$, or tetralinyl optionally substituted with 1 to 3 substituents independently selected from the group consisting of lower-alkyl, lower-alkoxy, halogen, CN, and CF$_3$, R$^3$ is hydrogen, lower-alkyl, benzyl, hydroxybenzyl or indolylmethylene, R$^4$ is hydrogen or lower-alkyl, or R$^3$ and R$^4$ are bonded to each other to form a ring together with the carbon atom to which they are attached and —R$^3$—R$^4$— is —(CH$_2$)$_{2-5}$—, R$^5$ is 5-membered heteroaryl, bi- or tricyclic heterocyclyl, or aminophenyl; optionally substituted with 1 to 3 substituents independently selected from the group consisting of lower-alkyl, lower-alkoxy, halogen, CN, CF$_3$, trifluoroacetyl, thiophenyl, and phenyl which can optionally be substituted with 1 to 3 substituents independently selected from the group consisting of lower-alkyl, lower-alkoxy, benzyloxy, halogen, CF$_3$, and CN, R$^6$ is a) pyridinyl or pyrimidinyl, which is substituted with 1 to 3 substituents independently selected from the group consisting of aryl and heteroaryl, which aryl or heteroaryl group can optionally be substituted with 1 to 3 substituents independently selected from the group consisting of lower-alkyl, lower-alkoxy, halogen, CN, and CF$_3$, or b) 5-membered heteroaryl, which can optionally be substituted with 1 to 3 substituents independently selected from the group consisting of lower-alkyl, carbonyl, aryl and heteroaryl, which aryl or heteroaryl group can optionally be substituted with 1 to 3 substituents independently selected from the group consisting of lower-alkyl, lower-alkoxy, halogen, CN, and CF$_3$, and which carbonyl group can optionally be substituted with lower-alkyl, lower-alkoxy, halogen, CN, CF$_3$, aryl, or heteroaryl, which aryl or heteroaryl group can optionally be substituted with 1 to 3 substituents independently selected from the group consisting of lower-alkyl, lower-alkoxy, halogen, CN, and CF$_3$, R$^7$ is aminophenyl, naphthyl or quinolyl, optionally substituted with 1 to 3 substituents independently selected from the group consisting of lower-alkyl, lower-alkoxy, halogen, CN and CF$_3$, X is C(R$^8$,R$^9$) or S, R$^8$ and R$^9$ independently from each other are H or lower-alkyl, and pharmaceutically acceptable salts thereof.

In another preferred embodiment, the present invention relates to compounds of formula (I) as defined above, in which R$^1$ is CN. Other preferred compounds are those, in which X is —CH$_2$—.

In addition, compounds of formula (I) as defined above, wherein R$^2$ is —C(R$^3$,R$^4$)—CH$_2$—R$^5$ and R$^5$ is oxazolyl, thiazolyl, indolyl, aza-indolyl, indolinyl, aminophenyl, or carbazolyl; optionally substituted with 1 to 3 substituents independently selected from the group consisting of lower-alkyl, lower-alkoxy, halogen, CN, CF$_3$, trifluoroacetyl, thiophenyl, and phenyl which can optionally be substituted with 1 to 3 substituents independently selected from the group consisting of lower-alkyl, lower-alkoxy, benzyloxy, halogen, CF$_3$, and CN; and R$^3$ and R$^4$ are as defined above, relate to a preferred embodiment of the present invention. Of these compounds, those wherein R$^5$ is a) indolyl substituted with 1 to 3 substituents independently selected from the group consisting of methyl, methoxy, cyano, chlorine, bromine, trifluoroacetyl and phenyl; or b) aminophenyl optionally substituted with 1 to 2 methyl goups; or c) indolinyl substituted with methoxy-phenyl; or d) oxazolyl substituted with 1 to 3 substituents independently selected from the group consisting of methyl and phenyl which is optionally substituted with 1 to 3 substituents independently selected from the group consisting of fluoro, chloro, ethoxy and benzyloxy; or e) 2-aza-indolyl, 7-aza-indolyl or carbazolyl; and R$^3$ and R$^4$ independently from each other are hydrogen or methyl, are more preferred. Each of the above mentioned definitions a), b), c), d) and e) individually relates to a preferred embodiment. Compounds as defined above, wherein R$^5$ is 5-cyano-2-methyl-indolyl, 5-methyl-2-phenyl-oxazolyl, or 2-(4-fluoro-phenyl)-5-methyl-oxazolyl; and wherein R$^3$ is methyl and R$^4$ is hydrogen, are particularly preferred.

Compounds of formula (I), wherein R$^2$ is —C(R$^3$,R$^4$)—CH$_2$—NH—R$^6$ and R$^6$ is a) pyridinyl which is substituted with 1 to 3 substituents independently selected from the group consisting of aryl and heteroaryl, which aryl or heteroaryl group can optionally be substituted with 1 to 3 substituents independently selected from the group consisting of lower-alkyl, lower-alkoxy, halogen, CN, and CF$_3$, or b) thiazolyl which can optionally be substituted with 1 to 3 substituents independently selected from the group consisting of lower-alkyl, carbonyl, aryl and heteroaryl, which aryl or heteroaryl group can optionally be substituted with 1 to 3 substituents independently selected from the group consisting of lower-alkyl, lower-alkoxy, halogen, CN, and CF$_3$, and which carbonyl group can optionally be substituted with lower-alkyl, lower-alkoxy, halogen, CN, CF$_3$, aryl, or heteroaryl, which aryl or heteroaryl group can optionally be substituted with 1 to 3 substituents independently selected from the group consisting of lower-alkyl, lower-alkoxy, halogen, CN, and $CF_3$, and $R^3$ and $R^4$ are as defined above, represent another preferred embodiment of the present invention. Each of the above mentioned definitions a) and b) individually relates to a preferred embodiment. Those compounds, wherein $R^6$ is a) pyridinyl substituted with phenyl, methoxy-phenyl, cyanophenyl, or methyl-oxadiazolyl, or b) thiazolyl substituted with 1 to 2 substituents independently selected form the group consisting of methyl, cyanophenyl, methoxyphenyl and phenyl-isoxazolyl, and $R^3$ and $R^4$ independently from each other are hydrogen or methyl, are more preferred. Each of the above mentioned definitions a) and b) individually relates to a preferred embodiment. Compounds of formula (I) as defined above, wherein $R^6$ is 5-(4-methoxy-phenyl)-pyridin-2-yl, 5-(5-methyl-oxadiazol-2-yl)-pyridin-2-yl, or 4-(4-cyano-phenyl)-thiazol-2-yl, and $R^3$ and $R^4$ are hydrogen or $R^3$ and $R^4$ are methyl, are particularly preferred.

Another preferred embodiment of the present invention relates to compounds of formula (I) as defined above, wherein $R^2$ is —$C(R^3,R^4)$—$CH_2$—O—$R^7$ and $R^7$ is aminophenyl, naphthyl or quinolinyl, optionally substituted with 1 to 3 substituents independently selected from the group consisting of lower-alkyl, lower-alkoxy, halogen, CN and $CF_3$, and $R^3$ and $R^4$ are as defined above, with those compounds, wherein $R^7$ is aminophenyl, naphthyl or quinolinyl, optionally substituted with 1 to 3 methyl-substituents, and $R^3$ and $R^4$ independently from each other are hydrogen or methyl being particularly preferred.

Other preferred compounds of formula (I) are those, wherein $R^2$ is tetralinyl optionally substituted with 1 to 3 substituents independently selected from the group consisting of lower-alkyl, lower-alkoxy, halogen, CN, and $CF_3$, with those compounds, wherein $R^2$ is tetralinyl optionally substituted with methoxy being more preferred and with those compounds, wherein $R^2$ is 6-methoxy-tetralin-2-yl being most preferred.

In a preferred embodiment of the present invention, $R^2$ is —$C(R^3,R^4)$—$(CH_2)_n$—$R^5$ and $R^5$ is 5-membered heteroaryl, bi- or tricyclic heterocyclyl, or aminophenyl; optionally substituted with 1 to 3 substituents independently selected from the group consisting of lower-alkyl, lower-alkoxy, halogen, CN, $CF_3$, trifluoroacetyl, thiophenyl, phenyl, heteroaryl and monocyclic heterocyclyl, which phenyl, heteroaryl or monocyclic heterocyclyl can optionally be substituted with 1 to 3 substituents independently selected from the group consisting of lower-alkyl, lower-alkoxy, benzyloxy, halogen, $CF_3$, $CF_3$—O, CN and NH—CO— lower-alkyl, and $R^3$, $R^4$ and n are as defined above.

More preferably, $R^5$ is oxazolyl, thiazolyl, pyrazolyl, triazolyl, imidazolyl, benzimidazolyl, indolyl, aza-indolyl, indolinyl, aminophenyl, or carbazolyl; optionally substituted with 1 to 3 substituents independently selected from the group consisting of lower-alkyl, lower-alkoxy, halogen, CN, $CF_3$, trifluoroacetyl, thiophenyl, pyrazinyl, pyridinyl, morpholinyl, piperidinyl, and phenyl, which pyridinyl can optionally be substituted with 1 to 3 substituents independently selected from the group consisting of lower-alkyl, lower-alkoxy halogen and $CF_3$, and which phenyl can optionally be substituted with 1 to 3 substituents independently selected from the group consisting of lower-alkyl, lower-alkoxy, benzyloxy, halogen, $CF_3$, $CF_3$—O, CN and NH—CO-lower-alkyl, and $R^3$ and $R^4$ independently from each other are hydrogen or lower-alkyl, or $R^3$ and $R^4$ are bonded to each other to form a ring together with the carbon atom to which they are attached and —$R^3$—$R^4$— is —$(CH_2)_{2-5}$—.

Even more preferably, $R^5$ is selected from the group consisting of 5-Methoxy-2-methyl-indol-1-yl, 5-cyano-indol-1-yl, 2-methyl-indol-1-yl, 2,3-Dimethyl-indol-1-yl, 3-methyl-indol-1-yl, 5-Brom-indol-1-yl, 5-Brom-2,3-dihydro-indol-1-yl, 7-aza-indol-1-yl, 2-aza-indol-1-yl, 5-phenyl-2,3-dihydro-indol-1-yl, 5-cyano-2-methyl-indol-1-yl, 2-phenyl-indol-1-yl, Carbazol-9-yl, 6-Brom-indol-1-yl, 7-methyl-indol-1-yl, 7-Brom-indol-1-yl, 4-Chlor-indol-1-yl, 5,6-Dimethoxy-indol-1-yl, 5,6-Dimethoxy-3-trifluoroacetyl-indol-1-yl, 6-(4-Methoxy-phenyl)-2,3-dihydro-indole-1-yl, 4-N,N-dimethylamino-phenyl, 3-N,N-dimethylamino-phenyl, 5-Methyl-2-phenyl-oxazol-4-yl, 2-(4-Fluoro-phenyl)-5-methyl-oxazol-4-yl, 2-(4-Benzyloxy-phenyl)-5-methyl-oxazol-4-yl, 2-(2-Ethoxy-4-fluoro-phenyl)-5-methyl-oxazol-4-yl, 2-(4-Chloro-phenyl)-5-methyl-oxazol-4-yl, 5-Methyl-2-phenyl-thiazol-4-yl, 2-(3-Methyl-phenyl)-5-methyl-oxazol-4-yl, 2-(3,5-Dimethoxy-phenyl)-5-methyl-oxazol-4-yl, 2-(4-Fluoro-3-methyl-phenyl)-5-methyl-oxazol-4-yl, 2-(3-Methyl-phenyl)-5-methyl-thiazol-4-yl, 2-(2-Ethyl-pyridin-4-yl)-5-methyl-thiazol-4-yl, 5-Methyl-2-(5-trifluoromethyl-pyridin-2-yl)-thiazol-4-yl, 5-Methyl-2-(6-methyl-pyridin-3-yl)-thiazol-4-yl, 2-(3-Chloro-phenyl)-5-methyl-oxazol-4-yl, 2-(2-Chloro-phenyl)-5-methyl-oxazol-4-yl, 2-phenyl-oxazol-4-yl, 2-phenyl-thiazol-4-yl, 2-morpholin-4-yl-thiazol-4-yl, 2-piperidin-1-yl-thiazol-4-yl, 5-methyl-3-phenyl-pyrazol-1-yl, 5-methyl-3-(3-trifluoromethyl-phenyl)-pyrazol-1-yl, 5-methyl-3-(3-trifluoromethoxy-phenyl)-pyrazol-1-yl, 5-Ethyl-3-phenyl-pyrazol-1-yl, 5-methyl-3-pyridin-3-yl-pyrazol-1-yl, 3-methyl-5-pyridin-3-yl-pyrazol-1-yl, 3-(3-Chloro-phenyl)-5-methyl-pyrazol-1-yl, 3-(3,4-Dichloro-phenyl)-5-methyl-pyrazol-1-yl, 3-phenyl-5-trifluoromethyl-pyrazol-1-yl, 5-Isopropyl-3-phenyl-pyrazol-1-yl, 5-methyl-3-thiophen-2-yl-pyrazol-1-yl, 5-methyl-3-pyridin-4-yl-pyrazol-1-yl, 5-methyl-3-(6-methyl-pyridin-3-yl)-pyrazol-1-yl, 5-Cyclopropyl-3-phenyl-pyrazol-1-yl, 5-methyl-3-pyrazin-2-yl-pyrazol-1-yl, 3-(5-Chloro-pyridin-3-yl)-5-methyl-pyrazol-1-yl, 5-methyl-3-pyridin-2-yl-pyrazol-1-yl, 3-pyridin-3-yl-5-trifluoromethyl-pyrazol-1-yl, 3-pyridin-3-yl-pyrazol-1-yl, 5-methyl-3-pyridin-3-yl-[1,2,4]triazol-1-yl, 3-pyridin-3-yl-5-trifluoromethyl-[1,2,4]triazol-1-yl, 5methyl-3-pyrazin-2-yl-[1,2,4]triazol-1-yl, 2-methyl-benzoimidazol-1-yl, 2-methyl-4-pyridin-3-yl-imidazol-1-yl, 4-phenyl-imidazol-1-yl, 4-pyridin-2-yl-imidazol-1-yl, 4-pyridin-3-yl-imidazol-1-yl, 3-phenyl-pyrazol-1-yl, 3-(4-Methoxy-phenyl)-pyrazol-1-yl, 3-(4-Methoxy-phenyl)-[1,2,4]triazol-1-yl, 5-methyl-3-phenyl-[1,2,4]triazol-1-yl, 2-Phenyl-1H-imidazol-4-yl, 5-Methyl-2-phenyl-1H-imidazol-4-yl, 5-Methyl-2-pyridin-4-yl-1H-imidazol-4-yl, 5-Methyl-2-pyridin-3-yl-1H-imidazol-4-yl, 5-Methyl-2-pyridin-2-yl-1H-imidazol-4-yl, 2-(3-Fluoro-4-methyl-phenyl)-5-methyl-1H-imidazol-4-yl, 5-methyl-2-(4-trifluoromethyl-phenyl)-1H-imidazol-4-yl, 5-methyl-2-m-tolyl-1H-imidazol-4-yl, 5-methyl-2-(3-chlorophenyl)-1H-imidazol-4-yl, 2-(3,5-Bis-trifluoromethyl-phenyl)-5-methyl-1H-imidazol-4-yl, 2-(3,5-Dichloro-phenyl)-5-methyl-1H-imidazol-4-yl, 1-methyl-2-phenyl-1H-imidazol-4-yl, 1,5-Dimethyl-2-phenyl-1H-imidazol-4-yl, 2-(3-Fluoro-phenyl)-5-methyl-1H-imidazol-4-yl, 2-(3-Methoxy-phenyl)-5-methyl-1H-imidazol-4-yl, 2-(3-Ethoxy-phenyl)-5-methyl-1H-imidazol-4-yl, 2-(3,5-Difluoro-phenyl)-5-methyl-1H-imidazol-4-yl, 2-(3,5-Dimethoxy-phenyl)-5-methyl-1H-imidazol-4-yl, 5-methyl-2-(3-trifluoromethyl-phenyl)-1H-imidazol-4-yl, 5-methyl-2-(3-trifluoromethoxy-phenyl)-1H-imidazol-4-yl, 2-(4-Chloro-phenyl)-5-methyl-1H-imidazol-4-yl, 5-methyl-2-p-tolyl-1H-imidazol-4-yl, 2-(3-Chloro-4-methyl-phenyl)-5- methyl-1H-imidazol-4-yl, and 2-(3-acetamidophenyl)-5-methyl-1H-imidazol-4-yl, and $R^3$ and $R^4$ independently from each other are hydrogen or methyl or $R^3$ and $R^4$ are bonded to each other to form a ring together with the carbon atom to which they are attached and —$R^3$—$R^4$— is —(CH$_2$)$_{2-5}$—.

Most preferably, $R^5$ is 5-Methoxy-2-methyl-indol-1-yl, 2-methyl-indol-1-yl, 2,3-Dimethyl-indol-1-yl, 5-cyano-2-methyl-indol-1-yl, 2-(4-Fluoro-phenyl)-5-methyl-oxazol-4-yl, 2-(4-Benzyloxy-phenyl)-5-methyl-oxazol-4-yl, 5-methyl-2-phenyl-oxazol-4-yl, 5-methyl-3-pyridin-3-yl-pyrazol-1-yl, 5-methyl-3-pyrazin-2-yl-pyrazol-1-yl, 3-pyridin-3-yl-pyrazol-1-yl, 5-methyl-3-pyridin-3-yl-[1,2,4]triazol-1-yl, 2-methyl-4-pyridin-3-yl-imidazol-1-yl, 4-pyridin-3-yl-imidazol-1-yl, and 5-cyano-indol-1-yl, and $R^3$ and $R^4$ independently from each other are hydrogen or methyl.

Other preferred compounds of formula (I) as defined above are those, wherein $R^2$ is —C($R^3$,$R^4$)—CH$_2$—NH—$R^6$ and $R^6$ is a) pyridinyl or pyrimidinyl, which is substituted with 1 to 3 substituents independently selected from the group consisting of aryl and heteroaryl, which aryl or heteroaryl group can optionally be substituted with 1 to 3 substituents independently selected from the group consisting of lower-alkyl, lower-alkoxy, halogen, CN, and CF$_3$, or b) 5-membered heteroaryl or bi- or tricyclic heterocyclyl, which 5-membered heteroaryl or bi- or tricyclic heterocyclyl can optionally be substituted with 1 to 3 substituents independently selected from the group consisting of lower-alkyl, carbonyl, aryl and heteroaryl, which aryl or heteroaryl group can optionally be substituted with 1 to 3 substituents independently selected from the group consisting of lower-alkyl, lower-alkoxy, halogen, CN, and CF$_3$, and which carbonyl group can optionally be substituted with lower-alkyl, lower-alkoxy, halogen, CN, CF$_3$, aryl, or heteroaryl, which aryl or heteroaryl group can optionally be substituted with 1 to 3 substituents independently selected from the group consisting of lower-alkyl, lower-alkoxy, halogen, CN, and CF$_3$, and $R^3$ and $R^4$ are as defined above.

More preferred compounds are those, wherein $R^6$ is a) pyridinyl or pyrimidinyl, which is substituted with 1 to 3 substituents independently selected from the group consisting of pyridinyl, oxadiazolyl, and phenyl, which oxadiazolyl can optionally be substituted with lower-alkyl, and which phenyl can optionally be substituted with 1 to 3 substituents independently selected from the group consisting of lower-alkyl, lower-alkoxy, CN, and CF$_3$, or b) thiazolyl or oxadiazolyl, which can optionally be substituted with 1 to 3 substituents independently selected from the group consisting of lower-alkyl, phenyl, benzoyl, phenyl-isoxazolyl and pyridyl, which pyridyl can optionally be substituted with lower-alkyl or halogen, and which phenyl can optionally be substituted with 1 to 3 substituents independently selected from the group consisting of lower-alkoxy, halogen, CN, and CF$_3$, c) 8H-indeno[1,2-d]thiazolyl, 4,5,6,7-tetrahydro-benzothiazolyl, 4,5,6,7-tetrahydro-thiazolo[5,4-c]pyridinyl, benzothiazolyl, benzooxazolyl or 1H-benzoimidazolyl, which 1H-benzoimidazolyl can optionally be substituted with lower-alkyl, and which 4,5,6,7-tetrahydro-thiazolo[5,4-c]pyridinyl can optionally be substituted with lower-alkyl-carbonyl or lower-alkoxy-carbonyl, and $R^3$ and $R^4$ independently from each other are hydrogen or lower-alkyl.

Even more preferred are those, wherein $R^6$ is selected from the group consisting of 5-(4-Methoxy-phenyl)-pyridin-2-yl, 5-(3-Methoxy-phenyl)-pyridin-2-yl, 5-(2-Methoxy-phenyl)-pyridin-2-yl, 5-(4-Cyano-phenyl)-pyridin-2-yl, 5-Phenyl-pyridin-2-yl, 6-Phenyl-pyridin-2-yl, 5-(5-Methyl-[1,3,4]oxadiazol-2-yl)-pyridin-2-yl, 3-(5-Methyl-[1,3,4]oxadiazol-2-yl)-pyridin-2-yl, 4,5-Dimethyl-thiazol-2-yl, 4-(4-Cyano-phenyl)-thiazol-2-yl, 4-(4-Methoxy-phenyl)-thiazol-2-yl, 4-(3-Phenyl-isoxazol-5-yl)-thiazol-2-yl, 5-phenyl-pyridin-2-yl, 5-(3-Cyano-phenyl)-pyridin-2-yl, 5-(3-trifluoromethyl-phenyl)-pyridin-2-yl, 5-(4-trifluoromethyl-phenyl)-pyridin-2-yl, 5-(2-trifluoromethyl-phenyl)-pyridin-2-yl, 5-(3,5-Bis-trifluoromethyl-phenyl)-pyridin-2-yl, [3,3']Bipyridinyl-6-yl, 5-(2,4-Dimethoxy-phenyl)-pyridin-2-yl, 6-(4-Methoxy-phenyl)-pyridin-2-yl, 6-(4-Cyano-phenyl)-pyridin-2-yl, 6-(3-Methoxy-phenyl)-pyridin-2-yl, 6-(3-Cyano-phenyl)-pyridin-2-yl, 6-(2-Methoxy-phenyl)-pyridin-2-yl, 6-(3,5-Bis-trifluoromethyl-phenyl)-pyridin-2-yl, 6-(4-trifluoromethyl-phenyl)-pyridin-2-yl, 6-(2-trifluoromethyl-phenyl)-pyridin-2-yl, 6-(3-trifluoromethyl-phenyl)-pyridin-2-yl, [2,3']Bipyridinyl-6-yl, 6-(2,4-Dimethoxy-phenyl)-pyridin-2-yl, 6-m-tolyl-pyridin-2-yl, 5-phenyl-pyrimidin-2-yl, 5-(3-Methoxy-phenyl)-pyrimidin-2-yl, 5-(3-Cyano-phenyl)-pyrimidin-2-yl, 5-(4-Cyano-phenyl)-pyrimidin-2-yl, 4-(2,4-Dimethoxy-phenyl)-thiazol-2-yl, 4-(2-Methoxy-phenyl)-thiazol-2-yl, 4-Phenyl-thiazol-2-yl, 4-(3-Methoxy-phenyl)-thiazol-2-yl, 8H-Indeno[1,2-d]thiazol-2-yl, 5-Methyl-4-phenyl-thiazol-2-yl, 4,5-Diphenyl-thiazol-2-yl, 4-Benzoyl-thiazol-2-yl, 4-(4-Fluoro-phenyl)-thiazol-2-yl, 4-(4-Trifluoromethyl-phenyl)-thiazol-2-yl, 4-Pyridin-2-yl-thiazol-2-yl, 4-Pyridin-4-yl-thiazol-2-yl, 5-Methyl-4-(4-trifluoromethyl-phenyl)-thiazol-2-yl, 4-(4-Cyano-phenyl)-5-methyl-thiazol-2-yl, 4-Pyridin-3-yl-thiazol-2-yl, 4,5,6,7-Tetrahydro-benzothiazol-2-yl, 6-ethoxycarbonyl-4,5,6,7-tetrahydro-thiazolo[5,4-c]pyridine-2-yl, 6-acetyl-4,5,6,7-tetrahydro-thiazolo [5,4-c]pyridine-2-yl, Benzothiazol-2-yl, Benzooxazol-2-yl, 1-methyl-1H-benzoimidazol-2-yl, 5-phenyl-[1,3,4]oxadiazol-2-yl, 3-pyridin-3-yl-[1,2,4]oxadiazol-5-yl, 3-phenyl-[1,2,4]oxadiazol-5-yl, 3-pyridin-2-yl-[1,2,4]oxadiazol-5-yl, 3-pyridin-4-yl-[1,2,4]oxadiazol-5-yl, 3-(6-methyl-pyridin-3-yl)-[1,2,4]oxadiazol-5-yl, 3-(2-Chloro-pyridin-4-yl)-[1,2,4]oxadiazol-5-yl, 3-(3,5-Dichloro-phenyl)-[1,2,4]oxadiazol-5-yl, and $R^3$ and $R^4$ independently from each other are hydrogen or methyl.

Most preferred are those, wherein $R^6$ is selected from the group consisting of 5-(4-Methoxy-phenyl)-pyridin-2-yl, 5-(3-Methoxy-phenyl)-pyridin-2-yl, 5-(2-Methoxy-phenyl)-pyridin-2-yl, 5-(4-Cyano-phenyl)-pyridin-2-yl, 5-Phenyl-pyridin-2-yl, 5-(5-Methyl-[1,3,4]oxadiazol-2-yl)-pyridin-2-yl, 4-(4-Cyano-phenyl)-thiazol-2-yl, 4-(3-Phenyl-isoxazol-5-yl)-thiazol-2-yl, 6-acetyl-4,5,6,7-tetrahydro-thiazolo[5,4-c]pyridine-2-yl, Benzothiazol-2-yl, 5-phenyl-[1,3,4]oxadiazol-2-yl, 3-pyridin-3-yl-[1,2,4]oxadiazol-5-yl, 3-pyridin-2-yl-[1,2,4]oxadiazol-5-yl, 3-pyridin-4-yl-[1,2,4]oxadiazol-5-yl, 3-(6-methyl-pyridin-3-yl)-[1,2,4]oxadiazol-5-yl, and $R^3$ and $R^4$ independently from each other are hydrogen or methyl.

Other preferred compounds are those, wherein $R^2$ is tetralinyl or tetrahydroquinolinyl, optionally substituted with 1 to 3 substituents independently selected from the group consisting of lower-alkyl, lower-alkoxy, halogen, CN, and CF$_3$. More preferably, $R^2$ is tetralinyl or tetrahydroquinolinyl, optionally substituted with methoxy.

Compounds of formula (I) represent a preferred embodiment of the present invention and pharmaceutically acceptable salts of compounds of formula (I) individually also represent a preferred embodiment of the present invention.

Preferred compounds of general formula (I) are those selected from the group consisting of
- (2S)-1-[((1R/S)-1,2,3,4-Tetrahydro-naphthalen-1-ylamino)-acetyl]-pyrrolidine-2-carbonitrile,
- (2S)-1-[((2R/S)-6-Methoxy-1,2,3,4-tetrahydro-naphthalen-2-ylamino)-acetyl]-pyrrolidine-2-carbonitrile,
- (2S)-1-[((2R/S)-1,2,3,4-Tetrahydro-naphthalen-1-ylamino)-acetyl]-pyrrolidine-2-carbonitrile,
- (2S)-1-{[(1S)-2-(5-Methoxy-2-methyl-indol-1-yl)-1-methyl-ethylamino]-acetyl}-pyrrolidine-2-carbonitrile,
- (2S)-1-{[(1S)-2-(5-cyano-indol-1-yl)-1-methyl-ethylamino]-acetyl}-pyrrolidine-2-carbonitrile,
- (2S)-1-{[(1S)-1-Methyl-2-(2-methyl-indol-1-yl)-ethylamino]-acetyl}-pyrrolidine-2-carbonitrile,
- (2S)-1-{[(1S)-2-(2,3-Dimethyl-indol-1-yl)-1-methyl-ethylamino]-acetyl}-pyrrolidine-2-carbonitrile,
- (2S)-1-{[(1S)-1-Methyl-2-(3-methyl-indol-1-yl)-ethylamino]-acetyl}-pyrrolidine-2-carbonitrile,
- (2S)-1-{[(1S)-2-(5-Brom-indol-1-yl)-1-methyl-ethylamino]-acetyl}-pyrrolidine-2-carbonitrile,
- (2S)-1-{[2-(5-Brom-2,3-dihydro-indol-1-yl)-ethylamino]-acetyl}-pyrrolidine-2-carbonitrile,
- (2S)-1-{[(1S)-2-(7-aza-indol-1-yl)-1-methyl-ethylamino]-acetyl}-pyrrolidine-2-carbonitrile,
- (2S)-1-{[(1S)-2-(2-aza-indol-1-yl)-1-methyl-ethylamino]-acetyl}-pyrrolidine-2-carbonitrile,
- (2S)-1-{[(1S)-1-Methyl-2-(5-phenyl-2,3-dihydro-indol-1-yl)-ethylamino]-acetyl}-pyrrolidine-2-carbonitrile,
- (2S)-1-{[(1S)-2-(5-cyano-2-methyl-indol-1-yl)-1-methyl-ethylamino]-acetyl}-pyrrolidine-2-carbonitrile,
- (2S)-1-{[(1S)-1-Methyl-2-(2-phenyl-indol-1-yl)-ethylamino]-acetyl}-pyrrolidine-2-carbonitrile,
- (2S)-1-[((1S)-2-Carbazol-9-yl-1-methyl-ethylamino)-acetyl]-pyrrolidine-2-carbonitrile,
- (2S)-1-{[(1S)-2-(6-Brom-indol-1-yl)-1-methyl-ethylamino]-acetyl}-pyrrolidine-2-carbonitrile,
- (2S)-1-{[(1S)-1-Methyl-2-(7-methyl-indol-1-yl)-ethylamino]-acetyl}-pyrrolidine-2-carbonitrile,
- (2S)-1-{[(1S)-2-(7-Brom-indol-1-yl)-1-methyl-ethylamino]-acetyl}-pyrrolidine-2-carbonitrile,
- (2S)-1-{[2-(4-Chlor-indol-1-yl)-ethylamino]-acetyl}-pyrrolidine-2-carbonitrile,
- (2S)-1-{[2-(5-Methoxy-2-methyl-indol-1-yl)-ethylamino]-acetyl}-pyrrolidine-2-carbonitrile,
- (2S)-1-{[(1S)-2-(5,6-Dimethoxy-indol-1-yl)-1-methyl-ethylamino]-acetyl}-pyrrolidine-2-carbonitrile,
- (2S)-1-{[(S)-2-(5,6-Dimethoxy-3-trifluoroacetyl-indol-1-yl)-1-methyl-ethylamino]-acetyl}-pyrrolidine-2-carbonitrile,
- (2S)-1-({(1S)-2-[6-(4-Methoxy-phenyl)-2,3-dihydro-indole-1-yl]-1-methyl-ethylamino}-acetyl)-pyrrolidine-2-carbonitrile,
- (2S)-1-{[(1S)-1-Methyl-2-(naphthalen-2-yloxy)-ethylamino]-acetyl}-pyrrolidine-2-carbonitrile,
- (2S)-1-{[2-(quinolin-6-yloxy)-ethylamino]-acetyl}-pyrrolidine-2-carbonitrile,
- (2S)-1-{[2-(3-N,N-dimethylamino-phenoxy)-ethylamino]-acetyl}-pyrrolidine-2-carbonitrile,
- (2S)-1-{[(1S)-2-(4-N,N-dimethylamino-phenyl)-1-methyl-ethylamino]-acetyl}-pyrrolidine-2-carbonitrile,
- (2S)-1-{[(1R)-2-(4-N,N-dimethylamino-phenyl)-1-methyl-ethylamino]-acetyl}-pyrrolidine-2-carbonitrile,
- (2S)-1-{[(1S)-2-(3-N,N-dimethylamino-phenyl)-1-methyl-ethylamino]-acetyl}-pyrrolidine-2-carbonitrile,
- (2S)-1-{[2-(5-Methyl-2-phenyl-oxazol-4-yl)-ethylamino]-acetyl}-pyrrolidine-2-carbonitrile,
- (2S)-1-({2-[2-(4-Fluoro-phenyl)-5-methyl-oxazol-4-yl]-ethylamino}-acetyl)-pyrrolidine-2-carbonitrile,
- (2S)-1-({2-[2-(4-Benzyloxy-phenyl)-5-methyl-oxazol-4-yl]-ethylamino}-acetyl)-pyrrolidine-2-carbonitrile,
- (2S)-1-({2-[2-(2-Ethoxy-4-fluoro-phenyl)-5-methyl-oxazol-4-yl]-ethylamino}-acetyl)-pyrrolidine-2-carbonitrile,
- (2S)-1-({2-[2-(4-Chloro-phenyl)-5-methyl-oxazol-4-yl]-ethylamino}-acetyl)-pyrrolidine-2-carbonitrile,
- (2S)-1-({2-[5-(4-Methoxy-phenyl)-pyridin-2-ylamino]-1,1-dimethyl-ethylamino}-acetyl)-pyrrolidine-2-carbonitrile,
- (2S)-1-({2-[5-(4-Methoxy-phenyl)-pyridin-2-ylamino]-ethylamino}-acetyl)-pyrrolidine-2-carbonitrile,
- 1-({2-[5-(4-Methoxy-phenyl)-pyridin-2-ylamino]-ethylamino}-acetyl)-pyrrolidine,
- (2S)-1-({2-[5-(3-Methoxy-phenyl)-pyridin-2-ylamino]-ethylamino}-acetyl)-pyrrolidine-2-carbonitrile,
- (2S)-1-({2-[5-(2-Methoxy-phenyl)-pyridin-2-ylamino]-ethylamino}-acetyl)-pyrrolidine-2-carbonitrile,
- (2S)-1-({2-[5-(4-Cyano-phenyl)-pyridin-2-ylamino]-ethylamino}-acetyl)-pyrrolidine-2-carbonitrile,
- (2S)-1-({2-[5-Phenyl-pyridin-2-ylamino]-ethylamino}-acetyl)-pyrrolidine-2-carbonitrile,
- 1-({2-[5-Phenyl-pyridin-2-ylamino]-ethylamino}-acetyl)-pyrrolidine,
- (2S)-1-({2-[6-Phenyl-pyridin-2-ylamino]-ethylamino}-acetyl)-pyrrolidine-2-carbonitrile,
- (2S)-1-({2-[5-(5-Methyl-[1,3,4]oxadiazol-2-yl)-pyridin-2-ylamino]-ethylamino}-acetyl)-pyrrolidine-2-carbonitrile,
- (2S)-1-({2-[3-(5-Methyl-[1,3,4]oxadiazol-2-yl)-pyridin-2-ylamino]-ethylamino}-acetyl)-pyrrolidine-2-carbonitrile,
- (2S)-1-{[2-(4,5-Dimethyl-thiazol-2-ylamino)-ethylamino]-acetyl}-pyrrolidine-2-carbonitrile,
- (2S)-1-({2-[4-(4-Cyano-phenyl)-thiazol-2-ylamino]-ethylamino}-acetyl)-pyrrolidine-2-carbonitrile,
- 1-({2-[4-(4-Cyano-phenyl)-thiazol-2-ylamino]-ethylamino}-acetyl)-pyrrolidine,
- (2S)-1-({2-[4-(4-Methoxy-phenyl)-thiazol-2-ylamino]-ethylamino}-acetyl)-pyrrolidine-2-carbonitrile, and
- (2S)-1-({2-[4-(3-Phenyl-isoxazol-5-yl)-thiazol-2-ylamino]-ethylamino}-acetyl)-pyrrolidine-2-carbonitrile, and pharmaceutically acceptable salts thereof.

Other preferred compounds of general formula (I) are those selected from the group consisting of
- (2S)-1-{[2-(5-Methyl-2-phenyl-thiazol-4-yl)-ethylamino]-acetyl}-pyrrolidine-2-carbonitrile,
- (2S)-1-({2-[2-(3-Methyl-phenyl)-5-methyl-oxazol-4-yl]-ethylamino}-acetyl)-pyrrolidine-2-carbonitrile,
- (2S)-1-({2-[2-(3,5-Dimethoxy-phenyl)-5-methyl-oxazol-4-yl]-ethylamino}-acetyl)-pyrrolidine-2-carbonitrile, (2S)-1-({2-[2-(4-Fluoro-3-methyl-phenyl)-5-methyl-oxazol-4-yl]-ethylamino}-acetyl)-pyrrolidine-2-carbonitrile, (2S)-1-({2-[2-(3-Methyl-phenyl)-5-methyl-thiazol-4-yl]-ethylamino}-acetyl)-pyrrolidine-2-carbonitrile, (2S)-1-({2-[2-(2-Ethyl-pyridin-4-yl)-5-methyl-thiazol-4-yl]-ethylamino}-acetyl)-pyrrolidine-2-carbonitrile, (2S)-1-({2-[5-Methyl-2-(5-trifluoromethyl-pyridin-2-yl)-thiazol-4-yl]-ethylamino}-acetyl)-pyrrolidine-2-carbonitrile, (2S)-1-({2-[5-Methyl-2-(6-methyl-pyridin-3-yl)-thiazol-4-yl]-ethylamino}-acetyl)-pyrrolidine-2-carbonitrile, (2S)-1-{[1,1-Dimethyl-2-(5-methyl-2-phenyl-oxazol-4-yl)-ethylamino]-acetyl}-pyrrolidine-2-carbonitrile, (2S)-1-({1,1-Dimethyl-2-[2-(3-methyl-phenyl)-5-methyl-oxazol-4-yl]-ethylamino}-acetyl)-pyrrolidine-2-carbonitrile, (2S)-1-{[-(5-Methyl-2-phenyl-oxazol-4-ylmethyl)-cyclopentylamino]-acetyl}-pyrrolidine-2-carbonitrile, (2S)-1-{[-(5-Methyl-2-phenyl-oxazol-4-ylmethyl)-cyclobutylamino]-acetyl}-pyrrolidine-2-carbonitrile, (2S)-1-{[1-(5-Methyl-2-phenyl-oxazol-4-ylmethyl)-cyclopropylamino]-acetyl}-pyrrolidine-2-carbonitrile, (2S)-1-{[1,1-Dimethyl-2-(5-methyl-2-phenyl-thiazol-4-yl)-ethylamino]-acetyl}-pyrrolidine-2-carbonitrile, (2S)-1-{[1-(5-Methyl-2-phenyl-thiazol-4-ylmethyl)-cyclopentylamino]-acetyl}-pyrrolidine-2-carbonitrile, (2S)-1-{[1-(5-Methyl-2-phenyl-thiazol-4-ylmethyl)-cyclobutylamino]-acetyl}-pyrrolidine-2-carbonitrile, (2S)-1-({2-[2-(4-Fluoro-3-methyl-phenyl)-5-methyl-oxazol-4-yl]-1,1-dimethyl-ethylamino}-acetyl)-pyrrolidine-2-carbonitrile, (2S)-1-({2-[2-(3-Chloro-phenyl)-5-methyl-oxazol-4-yl]-1,1-dimethyl-ethylamino}-acetyl)-pyrrolidine-2-carbonitrile, (2S)-1-({2-[2-(2-Chloro-phenyl)-5-methyl-oxazol-4-yl]-1,1-dimethyl-ethylamino}-acetyl)-pyrrolidine-2-carbonitrile, (2S)1-({1-[2-(4-Fluoro-3-methyl-phenyl)-5-methyl-oxazol-4-ylmethyl]-cyclopropylamino}-acetyl)-pyrrolidine-2-carbonitrile, (2S)-1-({1-[2-(3-Chloro-phenyl)-5-methyl-oxazol-4-ylmethyl]-cyclopropylamino}-acetyl)-pyrrolidine-2-carbonitrile, (2S)-1-({1-[2-(2-Chloro-phenyl)-5-methyl-oxazol-4-ylmethyl]-cyclopropylamino}-acetyl)-pyrrolidine-2-carbonitrile, (2S)-1-{[1,1-Dimethyl-2-(2-phenyl-oxazol-4-yl)-ethylamino]-acetyl}-pyrrolidine-2-carbonitrile, (2S)-1-{[1,1-Dimethyl-2-(2-phenyl-thiazol-4-yl)-ethylamino]-acetyl}-pyrrolidine-2-carbonitrile, (2S)-1-{[1,1-Dimethyl-2-(2-morpholin-4-yl-thiazol-4-yl)-ethylamino]-acetyl}-pyrrolidine-2-carbonitrile, (2S)-1-{[1,1-Dimethyl-2-(2-piperidin-1-yl-thiazol-4-yl)-ethylamino]-acetyl}-pyrrolidine-2-carbonitrile, (2S)-1-{[1,1-Dimethyl-3-(5-methyl-3-phenyl-pyrazol-1-yl)-propylamino]-acetyl}-pyrrolidine-2-carbonitrile, methanesulfonic acid salt, (2S)-1-{[3-(5-Methyl-3-phenyl-pyrazol-1-yl)-propylamino]-acetyl}-pyrrolidine-2-carbonitrile, methanesulfonic acid salt, (2S)-1-({1,1-Dimethyl-3-[5-methyl-3-(3-trifluoromethyl-phenyl)-pyrazol-1-yl]-propylamino}-acetyl)-pyrrolidine-2-carbonitrile, methanesulfonic acid salt, (2S)-1-({1,1-Dimethyl-3-[5-methyl-3-(3-trifluoromethoxy-phenyl)-pyrazol-1-yl]-propylamino}-acetyl)-pyrrolidine-2-carbonitrile, methanesulfonic acid salt, (2S)-1-{[3-(5-Ethyl-3-phenyl-pyrazol-1-yl)-1,1-dimethyl-propylamino]-acetyl}-pyrrolidine-2-carbonitrile, methanesulfonic acid salt, (2S)-1-{[1,1-Dimethyl-3-(5-methyl-3-pyridin-3-yl-pyrazol-1-yl)-propylamino]-acetyl}-pyrrolidine-2-carbonitrile, methanesulfonic acid salt, (2S)-1-{[1,1-Dimethyl-3-(3-methyl-5-pyridin-3-yl-pyrazol-1-yl)-propylamino]-acetyl}-pyrrolidine-2-carbonitrile, methanesulfonic acid salt, (2S)-1-({3-[3-(3-Chloro-phenyl)-5-methyl-pyrazol-1-yl]-1,1-dimethyl-propylamino}-acetyl)-pyrrolidine-2-carbonitrile, methanesulfonic acid salt, (2S)-1-({3-[3-(3,4-Dichloro-phenyl)-5-methyl-pyrazol-1-yl]-1,1-dimethyl-propylamino}-acetyl)-pyrrolidine-2-carbonitrile, methanesulfonic acid salt, (2S)-1-{[1,1-Dimethyl-3-(3-phenyl-5-trifluoromethyl-pyrazol-1-yl)-propylamino]-acetyl}-pyrrolidine-2-carbonitrile, methanesulfonic acid salt, (2S)-1-{[3-(5-Isopropyl-3-phenyl-pyrazol-1-yl)-1,1-dimethyl-propylamino]-acetyl}-pyrrolidine-2-carbonitrile, methanesulfonic acid salt, (2S)-1-{[1,1-Dimethyl-3-(5-methyl-3-thiophen-2-yl-pyrazol-1-yl)-propylamino]-acetyl}-pyrrolidine-2-carbonitrile, methanesulfonic acid salt, (2S)-1-{[1,1-Dimethyl-3-(5-methyl-3-pyridin-4-yl-pyrazol-1-yl)-propylamino]-acetyl}-pyrrolidine-2-carbonitrile, methanesulfonic acid salt, (2S)-1-({1,1-Dimethyl-3-[5-methyl-3-(6-methyl-pyridin-3-yl)-pyrazol-1-yl]-propylamino}-acetyl)-pyrrolidine-2-carbonitrile methanesulfonic acid salt, (2S)-1-{[3-(5-Cyclopropyl-3-phenyl-pyrazol-1-yl)-1,1-dimethyl-propylamino]-acetyl}-pyrrolidine-2-carbonitrile, methanesulfonic acid salt, (2S)-1-{[1,1-Dimethyl-3-(5-methyl-3-pyrazin-2-yl-pyrazol-1-yl)-propylamino]-acetyl}-pyrrolidine-2-carbonitrile, methanesulfonic acid salt, (2S)-1-({3-[3-(5-Chloro-pyridin-3-yl)-5-methyl-pyrazol-1-yl]-1,1-dimethyl-propylamino}-acetyl)-pyrrolidine-2-carbonitrile, methanesulfonic acid salt, (2S)-1-{[1,1-Dimethyl-3-(5-methyl-3-pyridin-2-yl-pyrazol-1-yl)-propylamino]-acetyl}-pyrrolidine-2-carbonitrile, methanesulfonic acid salt, (2S)-1-{[1,1-Dimethyl-3-(3-pyridin-3-yl-5-trifluoromethyl-pyrazol-1-yl)-propylamino]-acetyl}-pyrrolidine-2-carbonitrile, methanesulfonic acid salt, (2S)-1-{[1,1-Dimethyl-3-(3-pyridin-3-yl-pyrazol-1-yl)-propylamino]-acetyl}-pyrrolidine-2-carbonitrile, methanesulfonic acid salt, (2S)-1-{[1,1-Dimethyl-3-(5-methyl-3-pyridin-3-yl-[1,2,4]triazol-1-yl)-propylamino]-acetyl}-pyrrolidine-2-carbonitrile, methanesulfonic acid salt, (2S)-1-{[1,1-Dimethyl-3-(3-pyridin-3-yl-5-trifluoromethyl-[1,2,4]triazol-1-yl)-propylamino]-acetyl}-pyrrolidine-2-carbonitrile, methanesulfonic acid salt, (2S)-1-{[1,1-Dimethyl-3-(5-methyl-3-pyrazin-2-yl-[1,2,4]triazol-1-yl)-propylamino]-acetyl}-pyrrolidine-2-carbonitrile, (2S)-1-{[1,1-Dimethyl-3-(2-methyl-benzoimidazol-1-yl)-propylamino]-acetyl}-pyrrolidine-2-carbonitrile, (2S)-1-{[1,1-Dimethyl-3-(2-methyl-4-pyridin-3-yl-imidazol-1-yl)-propylamino]-acetyl}-pyrrolidine-2-carbonitrile, (2S)-1-{[1,1-Dimethyl-3-(4-phenyl-imidazol-1-yl)-propylamino]-acetyl}-pyrrolidine-2-carbonitrile, methanesulfonic acid salt, (2S)-1-{[1,1-Dimethyl-3-(4-pyridin-2-yl-imidazol-1-yl)-propylamino]-acetyl}-pyrrolidine-2-carbonitrile, methanesulfonic acid salt, (2S)-1-{[1,1-Dimethyl-3-(4-pyridin-3-yl-imidazol-1-yl)-propylamino]-acetyl}-pyrrolidine-2-carbonitrile, methanesulfonic acid salt, (2S)-1-[(6R/S)-(2-Methoxy-5,6,7,8-tetrahydro-quinolin-6-ylamino)-acetyl]-pyrrolidine-2-carbonitrile, methanesulfonic acid salt, (2S)-1-{[1,1-Dimethyl-3-(5-cyano-2-methyl-indol-1-yl)-propylamino]-acetyl}-pyrrolidine-2-carbonitrile, (2S)-1-{[(1S)-1-Methyl-2-(3-phenyl-pyrazol-1-yl)-ethylamino]-acetyl}-pyrrolidine-2-carbonitrile, (2S)-1-({(1S)-2-[3-(4-Methoxy-phenyl)-pyrazol-1-yl]-1-methyl-ethylamino}-acetyl)-pyrrolidine-2-carbonitrile, (2S)-1-({(1S)-2-[3-(4-Methoxy-phenyl)-[1,2,4]triazol-1-yl]-1-methyl-ethylamino}-acetyl)-pyrrolidine-2-carbonitrile, (2S)-1-{[(1S)-1-Methyl-2-(5-methyl-3-phenyl-[1,2,4]triazol-1-yl)-ethylamino]-acetyl}-pyrrolidine-2-carbonitrile, (2S)-1-{[(1S)-1-Methyl-2-(5-methyl-3-phenyl-pyrazol-1-yl)-ethylamino]-acetyl}-pyrrolidine-2-carbonitrile, (2S)-1-{[1,1-Dimethyl-2-(5-phenyl-pyridin-2-ylamino)-ethylamino]-acetyl}-pyrrolidine-2-carbonitrile, hydrochloride salt, (2S)-1-({2-[5-(3-Methoxy-phenyl)-pyridin-2-ylamino]-1,1-dimethyl-ethylamino}-acetyl)-pyrrolidine-2-carbonitrile, hydrochloride salt, (2S)-1-({2-[5-(4-Cyano-phenyl)-pyridin-2-ylamino]-1,1-dimethyl-ethylamino}-acetyl)-pyrrolidine-2-carbonitrile, hydrochloride salt, (2S)-1-({2-[5-(2-Methoxy-phenyl)-pyridin-2-ylamino]-1,1-dimethyl-ethylamino}-acetyl)-pyrrolidine-2-carbonitrile, hydrochloride salt, (2S)-1-({2-[5-(3-Cyano-phenyl)-pyridin-2-ylamino]-1,1-dimethyl-ethylamino}-acetyl)-pyrrolidine2-carbonitrile, hydrochloride salt, (2S)-1-({2-[5-(3-Cyano-phenyl)-pyridin-2-ylamino]-ethylamino}-acetyl)-pyrrolidine-2-carbonitrile, hydrochloride salt, (2S)-1-({1,1-Dimethyl-2-[5-(3-trifluoromethyl-phenyl)-pyridin-2-ylamino]-ethylamino}-acetyl)-pyrrolidine-2-carbonitrile, methansolfonic acid salt, (2S)-1-({1,1-Dimethyl-2-[5-(4-trifluoromethyl-phenyl)-pyridin-2-ylamino]-ethylamino}-acetyl)-pyrrolidine-2-carbonitrile, methansolfonic acid salt, (2S)-1-({1,1-Dimethyl-2-[5-(2-trifluoromethyl-phenyl)-pyridin-2-ylamino]-ethylamino}-acetyl)-pyrrolidine-2-carbonitrile, methansolfonic acid salt, (2S)-1-({2-[5-(3,5-Bis-trifluoromethyl-phenyl)-pyridin-2-ylamino]-1,1-dimethyl-ethylamino}-acetyl)-pyrrolidine-2-carbonitrile, methansolfonic acid salt, (2S)-1-{[2-([3,3']Bipyridinyl-6-ylamino)-1,1-dimethyl-ethylamino]-acetyl}-pyrrolidine-2-carbonitrile, methansolfonic acid salt, (2S)-1-({2-[5-(2,4-Dimethoxy-phenyl)-pyridin-2-ylamino]-1,1-dimethyl-ethylamino}-acetyl)-pyrrolidine-2-carbonitrile, methansolfonic acid salt, (2S)-1-({2-[6-(4-Methoxy-phenyl)-pyridin-2-ylamino]-ethylamino}-acetyl)-pyrrolidine-2-carbonitrile, hydrochloride salt, (2S)-1-({2-[6-(4-Cyano-phenyl)-pyridin-2-ylamino]-ethylamino}-acetyl)-pyrrolidine-2-carbonitrile, hydrochloride salt, (2S)-1-({2-[6-(3-Methoxy-phenyl)-pyridin-2-ylamino]-ethylamino}-acetyl)-pyrrolidine-2-carbonitrile, hydrochloride salt, (2S)-1-({2-[6-(4-Cyano-phenyl)-pyridin-2-ylamino]-1,1-dimethyl-ethylamino}-acetyl)-pyrrolidine-2-carbonitrile, hydrochloride salt, (2S)-1-{[1,1-Dimethyl-2-(6-phenyl-pyridin-2-ylamino)-ethylamino]-acetyl}-pyrrolidine-2-carbonitrile, hydrochloride salt, (2S)-1-({2-[6-(3-Cyano-phenyl)-pyridin-2-ylamino]-ethylamino}-acetyl)-pyrrolidine-2-carbonitrile, hydrochloride salt, (2S)-1-({2-[6-(3-Methoxy-phenyl)-pyridin-2-ylamino]-1,1-dimethyl-ethylamino}-acetyl)-pyrrolidine-2-carbonitrile, methansolfonic acid salt, (2S)-1-({2-[6-(4-Methoxy-phenyl)-pyridin-2-ylamino]-1,1-dimethyl-ethylamino}-acetyl)-pyrrolidine-2-carbonitrile, methansolfonic acid salt, (2S)-1-({2-[6-(2-Methoxy-phenyl)-pyridin-2-ylamino]-1,1-dimethyl-ethylamino}-acetyl)-pyrrolidine-2-carbonitrile, methansolfonic acid salt, (2S)-1-({2-[6-(2-Methoxy-phenyl)-pyridin-2-ylamino]-ethylamino}-acetyl)-pyrrolidine-2-carbonitrile, methansolfonic acid salt, (2S)-1-({2-[6-(3-Cyano-phenyl)-pyridin-2-ylamino]-1,1-dimethyl-ethylamino}-acetyl)-pyrrolidine-2-carbonitrile, methansolfonic acid salt, (2S)-1-({2-[6-(3,5-Bis-trifluoromethyl-phenyl)-pyridin-2-ylamino]-1,1-dimethyl-ethylamino}-acetyl)-pyrrolidine-2-carbonitrile, methansolfonic acid salt, (2S)-1-({1,1-Dimethyl-2-[6-(4-trifluoromethyl-phenyl)-pyridin-2-ylamino]-ethylamino}-acetyl)-pyrrolidine-2-carbonitrile, methansolfonic acid salt, (2S)-1-({1,1-Dimethyl-2-[6-(2-trifluoromethyl-phenyl)-pyridin-2-ylamino]-ethylamino}-acetyl)-pyrrolidine-2-carbonitrile, methansolfonic acid salt, (2S)-1-({1,1-Dimethyl-2-[6-(3-trifluoromethyl-phenyl)-pyridin-2-ylamino]-ethylamino}-acetyl)-pyrrolidine-2-carbonitrile, methansolfonic acid salt, (2S)-1-{[2-([2,3']Bipyridinyl-6-ylamino)-1,1-dimethyl-ethylamino]-acetyl}-pyrrolidine-2-carbonitrile, methansolfonic acid salt, (2S)-1-({2-[6-(2,4-Dimethoxy-phenyl)-pyridin-2-ylamino]-1,1-dimethyl-ethylamino}-acetyl)-pyrrolidine-2-carbonitrile, methansolfonic acid salt, (2S)-1-{[1,1-Dimethyl-2-(6-m-tolyl-pyridin-2-ylamino)-ethylamino]-acetyl}-pyrrolidine-2-carbonitrile, methanesulfonic acid salt, (2S)-1-{[1,1-Dimethyl-2-(5-phenyl-pyrimidin-2-ylamino)-ethylamino]-acetyl}-pyrrolidine-2-carbonitrile, (2S)-1-({2-[5-(3-Methoxy-phenyl)-pyrimidin-2-ylamino]-1,1-dimethyl-ethylamino}-acetyl)-pyrrolidine-2-carbonitrile, (2S)-1-({2-[5-(3-Cyano-phenyl)-pyrimidin-2-ylamino]-1,1-dimethyl-ethylamino}-acetyl)-pyrrolidine-2-carbonitrile, (2S)-1-({2-[5-(4-Cyano-phenyl)-pyrimidin-2-ylamino]-1,1-dimethyl-ethylamino}-acetyl)-pyrrolidine-2-carbonitrile, (2S)-1-({2-[4-(2,4-Dimethoxy-phenyl)-thiazol-2-ylamino]-ethylamino}-acetyl)-pyrrolidine-2-carbonitrile, (2S)-1-({2-[4-(2-Methoxy-phenyl)-thiazol-2-ylamino]-ethylamino}-acetyl)-pyrrolidine-2-carbonitrile, (2S)-1-{[2-(4-Phenyl-thiazol-2-ylamino)-ethylamino]-acetyl}-pyrrolidine-2-carbonitrile, (2S)-1-({2-[4-(3-Methoxy-phenyl)-thiazol-2-ylamino]-ethylamino}-acetyl)-pyrrolidine-2-carbonitrile, (2S)-1-{[2-(8H-Indeno[1,2-d]thiazol-2-ylamino)-ethylamino]-acetyl}-pyrrolidine-2-carbonitrile, hydrochloride salt, (2S)-1-{[2-(5-Methyl-4-phenyl-thiazol-2-ylamino)-ethylamino]-acetyl}-pyrrolidine-2-carbonitrile, hydrochloride salt, (2S)-1-{[2-(4,5-Diphenyl-thiazol-2-ylamino)-ethylamino]-acetyl}-pyrrolidine-2-carbonitrile, hydrochloride salt, (2S)-1-{[2-(4-Benzoyl-thiazol-2-ylamino)-ethylamino]-acetyl}-pyrrolidine-2-carbonitrile, (2S)-1-({2-[4-(4-Fluoro-phenyl)-thiazol-2-ylamino]-ethylamino}-acetyl)-pyrrolidine-2-carbonitrile, (2S)-1-({2-[4-(4-Trifluoromethyl-phenyl)-thiazol-2-ylamino]-ethylamino}-acetyl)-pyrrolidine-2-carbonitrile, (2S)-1-{[2-(4-Pyridin-2-yl-thiazol-2-ylamino)-ethylamino]-acetyl}-pyrrolidine-2-carbonitrile, (2S)-1-{[2-(4-Pyridin-4-yl-thiazol-2-ylamino)-ethylamino]-acetyl}-pyrrolidine-2-carbonitrile, (2S)-1-({2-[5-Methyl-4-(4-trifluoromethyl-phenyl)-thiazol-2-ylamino]-ethylamino}-acetyl)-pyrrolidine-2-carbonitrile, (2S)-1-({2-[4-(4-Cyano-phenyl)-5-methyl-thiazol-2-ylamino]-ethylamino}-acetyl)-pyrrolidine-2-carbonitrile, (2S)-1-{[2-(4-Pyridin-3-yl-thiazol-2-ylamino)-ethylamino]-acetyl}-pyrrolidine-2-carbonitrile, (2S)-1-({2-[4-(4-Cyano-phenyl)-thiazol-2-ylamino]-1,1-dimethyl-ethylamino}-acetyl)-pyrrolidine-2-carbonitrile, methanesulfonic acid salt, (2S)-1-{[2-(4,5,6,7-Tetrahydro-benzothiazol-2-ylamino)-ethylamino]-acetyl}-pyrrolidine-2-carbonitrile, (2S)-1-{[1,1-dimethyl-2-(6-ethoxycarbonyl-4,5,6,7-tetrahydro-thiazolo[5,4-c]pyridine-2-ylamino)-ethylamino]-acetyl}-pyrrolidine-2-carbonitrile, methanesulfonic acid salt, (2S)-1-{[1,1-dimethyl-2-(6-acetyl-4,5,6,7-tetrahydro-thiazolo[5,4-c]pyridine-2-ylamino)-ethylamino]-acetyl}-pyrrolidine-2-carbonitrile, methanesulfonic acid salt, (2S)-1-{[2-(Benzothiazol-2-ylamino)-1,1-dimethyl-ethylamino]-acetyl}-pyrrolidine-2-carbonitrile, (2S)-1-{[2-(Benzothiazol-2-ylamino)-ethylamino]-acetyl}-pyrrolidine-2-carbonitrile, (2S)-1-{[2-(Benzooxazol-2-ylamino)-ethylamino]-acetyl}-pyrrolidine-2-carbonitrile, (2S)-1-{[2-(Benzooxazol-2-ylamino)-1,1-dimethyl-ethylamino]-acetyl}-pyrrolidine-2-carbonitrile, (2S)-1-{[1,1-Dimethyl-2-(1-methyl-1H-benzoimidazol-2-ylamino)-ethylamino]-acetyl}-pyrrolidine-2-carbonitrile, (2S)-1-{[1,1-Dimethyl-2-(5-phenyl-[1,3,4]oxadiazol-2-ylamino)-ethylamino]-acetyl}-pyrrolidine-2-carbonitrile, methanesulfonic acid salt, (2S)-1-{[1,1-Dimethyl-2-(3-pyridin-3-yl-[1,2,4]oxadiazol-5-ylamino)-ethylamino]-acetyl}-pyrrolidine-2-carbonitrile, methanesulfonic acid salt, (2S)-1-{[1,1-Dimethyl-2-(3-phenyl-[1,2,4]oxadiazol-5-ylamino)-ethylamino]-acetyl}-pyrrolidine-2-carbonitrile, methanesulfonic acid salt, (2S)-1-{[1,1-Dimethyl-2-(3-pyridin-2-yl-[1,2,4]oxadiazol-5-ylamino)-ethylamino]-acetyl}-pyrrolidine-2-carbonitrile, methanesulfonic acid salt, (2S)-1-{[1,1-Dimethyl-2-(3-pyridin-4-yl-[1,2,4]oxadiazol-5-ylamino)-ethylamino]-acetyl}-pyrrolidine-2-carbonitrile, methanesulfonic acid salt, (2S)-1-({1,1-Dimethyl-2-[3-(6-methyl-pyridin-3-yl)-[1,2,4]oxadiazol-5-ylamino]-ethylamino}-acetyl)-pyrrolidine-2-carbonitrile, methanesulfonic acid salt, (2S)-1-({2-[3-(2-Chloro-pyridin-4-yl)-[1,2,4]oxadiazol-5-ylamino]-1,1-dimethyl-ethylamino}-acetyl)-pyrrolidine-2-carbonitrile, methanesulfonic acid salt, (2S)-1-({2-[3-(3,5-Dichloro-phenyl)-[1,2,4]oxadiazol-5-ylamino]-1,1-dimethyl-ethylamino}-acetyl)-pyrrolidine-2-carbonitrile, methanesulfonic acid salt, (2S)-1-{[3-(2-Phenyl-1H-imidazol-4-yl)-propylamino]-acetyl}-pyrrolidine-2-carbonitrile, (2S)-1-{[(5-Methyl-2-phenyl-1H-imidazol-4-ylmethyl)-amino]-acetyl}-pyrrolidine-2-carbonitrile, (2S)-1-{[2-(5-Methyl-2-phenyl-1H-imidazol-4-yl)-ethylamino]-acetyl}-pyrrolidine-2-carbonitrile, (2S)-1-{[2-(5-Methyl-2-pyridin-4-yl-1H-imidazol-4-yl)-ethylamino]-acetyl}-pyrrolidine-2-carbonitrile, (2S)-1-{[2-(5-Methyl-2-pyridin-3-yl-1H-imidazol-4-yl)-ethylamino]-acetyl}-pyrrolidine-2-carbonitrile, (2S)-1-{[2-(5-Methyl-2-pyridin-2-yl-1H-imidazol-4-yl)-ethylamino]-acetyl}-pyrrolidine-2-carbonitrile, (2S)-1-{[2-(2-Phenyl-1H-imidazol-4-yl)-ethylamino]-acetyl}-pyrrolidine-2-carbonitrile, (2S)-1-({2-[2-(3-Fluoro-4-methyl-phenyl)-5-methyl-1H-imidazol-4-yl]-1,1-dimethyl-ethylamino}-acetyl)-pyrrolidine-2-carbonitrile, (2S)-1-({1,1-Dimethyl-2-[5-methyl-2-(4-trifluoromethyl-phenyl)-1H-imidazol-4-yl]-ethylamino}-acetyl)-pyrrolidine-2-carbonitrile, (2S)-1-{[1,1-Dimethyl-2-(5-methyl-2-m-tolyl-1H-imidazol-4-yl)-ethylamino]-acetyl}-pyrrolidine-2-carbonitrile, (2S)-({1,1-Dimethyl-2-[5-methyl-2-(3-chlorophenyl)-1H-imidazol-4-yl]-ethylamino}-acetyl)-pyrrolidine-2-carbonitrile, (2S)-1-({2-[2-(3,5-Bis-trifluoromethyl-phenyl)-5-methyl-1H-imidazol-4-yl]-1,1-dimethyl-ethylamino}-acetyl)-pyrrolidine-2-carbonitrile, (2S)-1-({2-[2-(3,5-Dichloro-phenyl)-5-methyl-1H-imidazol-4-yl]-1,1-dimethyl-ethylamino}-acetyl)-pyrrolidine-2-carbonitrile, (2S)-1-{[1,1-Dimethyl-2-(2-phenyl-1H-imidazol-4-yl)-ethylamino]-acetyl}-pyrrolidine-2-carbonitrile, (2S)-1-{[1,1-Dimethyl-2-(1-methyl-2-phenyl-1H-imidazol-4-yl)-ethylamino]-acetyl}-pyrrolidine-2-carbonitrile, (2S)-1-{[2-(1,5-Dimethyl-2-phenyl-1H-imidazol-4-yl)-1,1-dimethyl-ethylamino]-acetyl}-pyrrolidine-2-carbonitrile, (2S)-1-({2-[2-(3-Fluoro-phenyl)-5-methyl-1H-imidazol-4-yl]-1,1-dimethyl-ethylamino}-acetyl)-pyrrolidine-2-carbonitrile, (2S)-1-({2-[2-(3-Methoxy-phenyl)-5-methyl-1H-imidazol-4-yl]-1,1-dimethyl-ethylamino}-acetyl)-pyrrolidine-2-carbonitrile, (2S)-1-({2-[2-(3-Ethoxy-phenyl)-5-methyl-1H-imidazol-4-yl]-1,1-dimethyl-ethylamino}-acetyl)-pyrrolidine-2-carbonitrile, (2S)-1-({2-[2-(3,5-Difluoro-phenyl)-5-methyl-1H-imidazol-4-yl]-1,1-dimethyl-ethylamino}-acetyl)-pyrrolidine-2-carbonitrile, (2S)-1-({2-[2-(3,5-Dimethoxy-phenyl)-5-methyl-1H-imidazol-4-yl]-1,1-dimethyl-ethylamino}-acetyl)-pyrrolidine-2-carbonitrile, (2S)-1-({1,1-Dimethyl-2-[5-methyl-2-(3-trifluoromethyl-phenyl)-1H-imidazol-4-yl]-ethylamino}-acetyl)-pyrrolidine-2-carbonitrile, (2S)-1-{[1,1-Dimethyl-2-(5-methyl-2-pyridin-2-yl-1H-imidazol-4-yl)-ethylamino]-acetyl}-pyrrolidine-2-carbonitrile, (2S)-1-{[1,1-Dimethyl-2-(5-methyl-2-pyridin-3-yl-1H-imidazol-4-yl)-ethylamino]-acetyl}-pyrrolidine-2-carbonitrile, (2S)-1-{[1,1-Dimethyl-2-(5-methyl-2-pyridin-4-yl-1H-imidazol-4-yl)-ethylamino]-acetyl}-pyrrolidine-2-carbonitrile, (2S)-1-({1,1-Dimethyl-2-[5-methyl-2-(3-trifluoromethoxy-phenyl)-1H-imidazol-4-yl]-ethylamino}-acetyl)-pyrrolidine-2-carbonitrile, (2S)-1-{[1,1-Dimethyl-2-(5-methyl-2-phenyl-1H-imidazol-4-yl)-ethylamino]-acetyl}-pyrrolidine-2-carbonitrile, (2S)-1-({2-[2-(4-Chloro-phenyl)-5-methyl-1H-imidazol-4-yl]-1,1-dimethyl-ethylamino}-acetyl)-pyrrolidine-2-carbonitrile, (2S)-1-{[1,1-Dimethyl-2-(5-methyl-2-p-tolyl-1H-imidazol-4-yl)-ethylamino]-acetyl}-pyrrolidine-2-carbonitrile, (2S)-1-({2-[2-(3-Chloro-4-methyl-phenyl)-5-methyl-1H-imidazol-4-yl]-1,1-dimethyl-ethylamino}-acetyl)-pyrrolidine-2-carbonitril, and (2S)-1-({1,1-Dimethyl-2-[2-(3-acetamidophenyl)-5-methyl-1H-imidazol-4-yl]-ethylamino}-acetyl)-pyrrolidine-2-carbonitrile, and pharmaceutically acceptable salts thereof.

Especially preferred compounds of general formula (I) are those selected from the group consisting of (2S)-1-({2-[5-(5-Methyl-[1,3,4]oxadiazol-2-yl)-pyridin-2-ylamino]-ethylamino}-acetyl)-pyrrolidine-2-carbonitrile, (2S)-1-{[(1S)-2-(5-cyano-2-methyl-indol-1-yl)-1-methyl-ethylamino]-acetyl}-pyrrolidine-2-carbonitrile, (2S)-1-{[2-(5-Methyl-2-phenyl-oxazol-4-yl)-ethylamino]-acetyl}-pyrrolidine-2-carbonitrile, (2S)-1-[((2R/S)-6-Methoxy-1,2,3,4-tetrahydro-naphthalen-2-ylamino)-acetyl]-pyrrolidine-2-carbonitrile, (2S)-1-({2-[2-(4-Fluoro-phenyl)-5-methyl-oxazol-4-yl]-ethylamino}-acetyl)-pyrrolidine-2-carbonitrile, (2S)-1-({2-[5-(4-Methoxy-phenyl)-pyridin-2-ylamino]-1,1-dimethyl-ethylamino}-acetyl)-pyrrolidine-2-carbonitrile, and (2S)-1-({2-[4-(4-Cyano-phenyl)-thiazol-2-ylamino]-ethylamino}-acetyl)-pyrrolidine-2-carbonitrile, and pharmaceutically acceptable salts thereof.

Other especially preferred compounds of general formula (I) are those selected from the group consisting of (2S)-1-({2-[5-(3-Methoxy-phenyl)-pyridin-2-ylamino]-ethylamino}-acetyl)-pyrrolidine-2-carbonitrile, (2S)-1-{[(1S)-2-(5-Methoxy-2-methyl-indol-1-yl)-1-methyl-ethylamino]-acetyl}-pyrrolidine-2-carbonitrile, (2S)-1-(2-[5-(4-Cyano-phenyl)-pyridin-2-ylamino]-ethylamino}-acetyl)-pyrrolidine-2-carbonitrile, (2S)-1-({2-[5-Phenyl-pyridin-2-ylamino]-ethylamino}-acetyl)-pyrrolidine-2-carbonitrile, (2S)-1-({2-[4-(3-Phenyl-isoxazol-5-yl)-thiazol-2-ylamino]-ethylamino}-acetyl)-pyrrolidine-2-carbonitrile, (2S)-1-{[(1S)-1-Methyl-2-(2-methyl-indol-1-yl)-ethylamino]-acetyl}-pyrrolidine-2-carbonitrile, (2S)-1-({2-[5-(4-Methoxy-phenyl)-pyridin-2-ylamino]-ethylamino}-acetyl)-pyrrolidine-2-carbonitrile, (2S)-1-({2-[2-(4-Benzyloxy-phenyl)-5-methyl-oxazol-4-yl]-ethylamino}-acetyl)-pyrrolidine-2-carbonitrile, (2S)-1-{[(1S)-2-(2,3-Dimethyl-indol-1-yl)-1-methyl-ethylamino]-acetyl}-pyrrolidine-2-carbonitrile, (2S)-1-({2-[5-(2-Methoxy-phenyl)-pyridin-2-ylamino]-ethylamino}-acetyl)-pyrrolidine-2-carbonitrile, and (2S)-1-{[(1S)-2-(5-cyano-indol-1-yl)-1-methyl-ethylamino]-acetyl}-pyrrolidine-2-carbonitrile, and pharmaceutically acceptable salts thereof.

Other especially preferred compounds of general formula (I) are those selected from the group consisting of (2S)-1-{[1,1-Dimethyl-2-(5-methyl-2-phenyl-oxazol-4-yl)-ethylamino]-acetyl}-pyrrolidine-2-carbonitrile, (2S)-1-{[1,1-Dimethyl-3-(5-methyl-3-pyridin-3-yl-pyrazol-1-yl)-propylamino]-acetyl}-pyrrolidine-2-carbonitrile, (2S)-1-{[1,1-Dimethyl-3-(5-methyl-3-pyrazin-2-yl-pyrazol-1-yl)-propylamino]-acetyl}-pyrrolidine-2-carbonitrile, (2S)-1-{[1,1-Dimethyl-3-(3-pyridin-3-yl-pyrazol-1-yl)-propylamino]-acetyl}-pyrrolidine-2-carbonitrile, (2S)-1-{[1,1-Dimethyl-3-(5-methyl-3-pyridin-3-yl-[1,2,4]triazol-1-yl)-propylamino]-acetyl}-pyrrolidine-2-carbonitrile, (2S)-1-{[1,1-Dimethyl-3-(2-methyl-4-pyridin-3-yl-imidazol-1-yl)-propylamino]-acetyl}-pyrrolidine-2-carbonitrile, (2S)-1-{[1,1-Dimethyl-3-(4-pyridin-3-yl-imidazol-1-yl)-propylamino]-acetyl}-pyrrolidine-2-carbonitrile, (2S)-1-{[1,1-dimethyl-2-(6-acetyl-4,5,6,7-tetrahydro-thiazolo[5,4-c]pyridine-2-ylamino)-ethylamino]-acetyl}-pyrrolidine-2-carbonitrile, (2S)-1-{[2-(Benzothiazol-2-ylamino)-1,1-dimethyl-ethylamino]-acetyl}-pyrrolidine-2-carbonitrile, (2S)-1-{[1,1-Dimethyl-2-(5-phenyl-[1,3,4]oxadiazol-2-ylamino)-ethylamino]-acetyl}-pyrrolidine-2-carbonitrile, (2S)-1-{[1,1-Dimethyl-2-(3-pyridin-3-yl-[1,2,4]oxadiazol-5-ylamino)-ethylamino]-acetyl}-pyrrolidine-2-carbonitrile, (2S)-1-{[1,1-Dimethyl-2-(3-pyridin-2-yl-[1,2,4]oxadiazol-5-ylamino)-ethylamino]-acetyl}-pyrrolidine-2-carbonitrile, (2S)-1-{[1,1-Dimethyl-2-(3-pyridin-4-yl-[1,2,4]oxadiazol-5-ylamino)-ethylamino]-acetyl}-pyrrolidine-2-carbonitrile, and (2S)-1-({1,1-Dimethyl-2-[3-(6-methyl-pyridin-3-yl)-[1,2,4]oxadiazol-5-ylamino]-ethylamino}-acetyl)-pyrrolidine-2-carbonitrile, and pharmaceutically acceptable salts thereof.

Compounds of formula (I) can have one or more asymmetric carbon atoms and can exist in the form of optically pure enantiomers or as racemates. The invention embraces all of these forms.

It will be appreciated, that the compounds of general formula (I) in this invention may be derivatised at functional groups to provide derivatives which are capable of conversion back to the parent compound in vivo.

The present invention also relates to a process for the manufacture of compounds of formula (I) as defined above, which process comprises reacting a compound of formula (II)

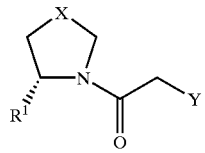

(II)

with a compound $R^2$—$NH_2$, wherein $R^1$, $R^2$ and X are as defined above and Y is a leaving group, to yield said compound of formula (I), and optionally converting the compound of formula (I) to a pharmaceutically acceptable salt. Preferred is a process as described above, in which Y is halogen, mesylate or tosylate, more preferably chlorine or bromine.

In general, a compound of formula (II) is treated with one to five equivalents of a compound $R^2$—$NH_2$, in the optional presence of an additional base such as a tertiary amine, a carbonate or a hydroxide at a temperature ranging from −78° to 70° in an inert solvent such as THF or DMF for 0.1 to 7 days and the resulting compound of formula (I) is isolated by standard isolation procedures. Optionally, the resulting compound of formula (I) can be converted to a salt (acid addition salt) using methods known to the person skilled in the art.

The invention further relates to compounds of formula (I) as defined above, when manufactured according to a process as defined above.

As described above, the compounds of formula (I) of the present invention can be used as medicaments for the treatment and/or prophylaxis of diseases which are associated with DPP IV such as diabetes, particularly non-insulin dependent diabetes mellitus, impaired glucose tolerance, bowl disease, colitis ulcerosa, morbus crohn, obesity, and/or metabolic syndrome, preferably non-insulin dependent diabetes mellitus and/or impaired glucose tolerance. Furthermore, the compounds of the present invention can be used as diuretic agents or for the treatment and/or prophylaxis of hypertension.

The invention therefore also relates to pharmaceutical compositions comprising a compound as defined above and a pharmaceutically acceptable carrier and/or adjuvant.

Further, the invention relates to compounds as defined above for use as therapeutic active substances, particularly as therapeutic active substances for the treatment and/or prophylaxis of diseases which are associated with DPP IV such as diabetes, particularly non-insulin dependent diabetes mellitus, impaired glucose tolerance, bowl disease, colitis ulcerosa, morbus crohn, obesity, and/or metabolic syndrome, preferably for use as therapeutic active substances for the treatment and/or prophylaxis of non-insulin dependent diabetes mellitus and/or impaired glucose tolerance. The invention relates furthermore to compounds as defined above for use as diuretic agents or for use as therapeutic active substances for the treatment and/or prophylaxis of hypertension.

In another embodiment, the invention relates to a method for the treatment and/or prophylaxis of diseases which are associated with DPP IV such as diabetes, particularly non-insulin dependent diabetes mellitus, impaired glucose tolerance, bowl disease, colitis ulcerosa, morbus crohn, obesity, and/or metabolic syndrome, preferably for the treatment and/or prophylaxis of non-insulin dependent diabetes mellitus and/or impaired glucose tolerance, which method comprises administering a compound as defined above to a human being or animal. The invention relates furthermore to a method for the treatment and/or prophylaxis as defined above, wherein the disease is hypertension or wherein a diuretic agent has a beneficial effect.

The invention further relates to the use of compounds as defined above for the treatment and/or prophylaxis of diseases which are associated with DPP IV such as diabetes, particularly non-insulin dependent diabetes mellitus, impaired glucose tolerance, bowl disease, colitis ulcerosa, morbus crohn, obesity, and/or metabolic syndrome, preferably for the treatment and/or prophylaxis of non-insulin dependent diabetes mellitus and/or impaired glucose tolerance. The invention relates furthermore to the use as defined above, wherein the disease is hypertension or to the use as diuretic agent.

In addition, the invention relates to the use of compounds as defined above for the preparation of medicaments for the treatment and/or prophylaxis of diseases which are associated with DPP IV such as diabetes, particularly non-insulin dependent diabetes mellitus, impaired glucose tolerance, bowl disease, colitis ulcerosa, morbus crohn, obesity, and/or metabolic syndrome, preferably for the treatment and/or prophylaxis of non-insulin dependent diabetes mellitus and/or impaired glucose tolerance. Such medicaments comprise a compound as defined above. The invention relates furthermore to the use as defined above, wherein the disease is hypertension or the use for the preparation of diuretic agents. In context with the methods and uses defined above, the following diseases relate to a preferred embodiment: diabetes, particularly non-insulin dependent diabetes mellitus, impaired glucose tolerance, obesity, and/or metabolic syndrome, preferably non-insulin dependent diabetes mellitus and/or impaired glucose tolerance.

The compounds of formula (I) can be manufactured by the methods given below, by the methods given in the examples or by analogous methods. Appropriate reaction conditions for the individual reaction steps are known to the person skilled in the art. Starting materials are either commercially available or can be prepared by methods analogous to the methods given below or in the examples or by methods known in the art.

The following tests were carried out in order to determine the activity of the compounds of formula I.

Activity of DPP-IV inhibitors are tested with natural human DPP-IV derived from a human plasma pool or with recombinat human DPP-IV. Human citrate plasma from different donors is pooled, filtered through a 0.2 micron membrane under sterile conditions and aliquots of 1 ml are shock frozen and stored at −120° C. until used. In the calorimetric DPP-IV assay 5 to 10 μl human plasma and in the fluorometric assay 1.0 µl of human plasma in a total assay volume of 100 µl is used as an enzyme source. The cDNA of the human DPP-IV sequence of amino acid 31- to 766, restricted for the N-terminus and the transmembrane domain, is cloned into pichia pastoris. Human DPP-IV is expressed and purified from the cultur medium using conventional column chromatography including size exclusion and anion and cation chromatography. The purity of the final enzyme preparation of Coomassie blue SDS-PAGE is >95%. In the calorimetric DPP-IV assay 20 ng rec.-h DPP-IV and in the fluorometric assay 2 ng rec-h DPP-IV in a total assay volume of 100 µl is used as an enzyme source.

In the fluorogenic assay Ala-Pro-7-amido-4-trifluoromethylcoumarin (Calbiochem No 125510) is used as a substrate. A 20 mM stock solution in 10% DMF/$H_2O$ is stored at −20° C. until use. In IC50 determinations a final substrate concentration of 50 µM is used. In assays to determine kinetic parameters as Km, Vmax, Ki, the substrate concentration is varied between 10 µM and 500 µM.

In the colorimetric assay H-Ala-Pro-pNA.HCl (Bachem L-1115) is used as a substrate. A 10 mM stock solution in 10% MeOH/$H_2O$ is stored at −20° C. until use. In IC50 determinations a final substrate concentration of 200 µM is used. In assays to determine kinetic parameters as Km, Vmax, Ki, the substrate concentration is varied between 100 µM and 2000 µM.

Fluorescence is detected in a Perkin Elmer Luminescence Spectrometer LS 50B at an excitation wavelength of 400 nm and an emission wavelength of 505 nm continuously every 15 seconds for 10 to 30 minutes. Initial rate constants are calculated by best fit linear regression.

The absorption of pNA liberated from the calorimetric substrate is detected in a Packard SpectraCount at 405 nM continuosly every 2 minutes for 30 to 120 minutes. Initial rate constants are calculated by best fit linear regression.

DPP-IV activity assays are performed in 96 well plates at 37° C. in a total assay volume of 100 µl. The assay buffer consists of 50 mM Tris/HCl pH 7.8 containing 0.1 mg/ml BSA and 100 mM NaCl. Test compounds are solved in 100% DMSO, diluted to the desired concentration in 10% DMSO/$H_2O$. The final DMSO concentration in the assay is 1% (v/v). At this concentration enzyme inactivation by DMSO is <5%. Compounds are with (10 minutes at 37° C.) and without preincubation with the enzyme. Enzyme reactions are started with substrate application follwed by immediate mixing.

IC50 determinations of test compounds are calculated by non-linear best fit regression of the DPP-IV inhibition of at least 5 different compound concentrations. Kinetic parameters of the enzyme reaction are calculated at at least 5 different substrate concentrations and at least 5 different test compound concentrations.

The preferred compounds of the present invention exhibit IC50 values of 1 nM to 10 µM, more preferrably of 1–100 nM, as shown in the following table.

| Example | IC50 [µM] |
|---|---|
| 6 | 0.069 |
| 7 | 0.088 |
| 23 | 0.128 |
| 119 | 0.007 |
| 129 | 0.001 |
| 188 | 0.001 |

The compounds of formula I and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragees, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragees and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 100 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1–500 mg, preferably 1–100 mg, of a compound of formula I.

The following Examples serve to illustrate the present invention in more detail. They are, however, not intended to limit its scope in any manner.

General Methods

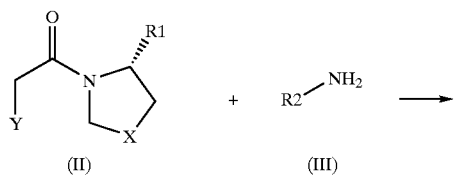

(II)

X = CH₂, R1 = CN, Y = Cl: IIA
X = CH₂, R1 = CN, Y = Br: IIB
X = CH₂, R1 = H,  Y = Br: IIC

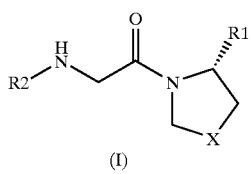

(I)

The compounds of formula (I) can be manufactured by the methods given below, by the methods outlined in the examples or by analogous methods. α-Haloamides (II) were made from (S)-prolylamide in analogy to procedures described in WO 98/19998. Starting amines of the general formula (III) are commercially available or can be prepared by methods found in the literature or according to the methods given below and within the example section (e.g. IIIA-IIIT). In general, an α-haloamide II is treated with one to five equivalents of an amine III, in the optional presence of an additional base such as a tertiary amine, a carbonate or a hydroxide, at a temperature ranging from −78° to 70° in an inert solvent such as THF or DMF for 0.1 to 7 days and the resulting product I is isolated by standard isolation procedures. Optionally, an acid addition salt can be made using methods known to people skilled in the art. Compounds in which X=S can be made either by analogous methods or by methods known to the person skilled in the art.

Compounds of the formula (I) wherein X is C(R⁸,R⁹) and R⁸,R⁹ are independently from each other lower alkyl can be obtained from suitable protected glutamic acid analogues by alkylation and subsequent cyclisation to proline derivatives. These can further be elaborated to the α-haloamides II in an analogue fashion as described for (S)-prolylamide.

Compounds of the formula (I) wherein R² is —C(R³, R⁴)—CH₂—NH—R⁶ might require the synthesis of the corresponding amine precursors IIIE, IIIF, IIIN, IIIO and IIIP. Preparation of these amine derivatives is described in the general schemes below:

Scheme 1:

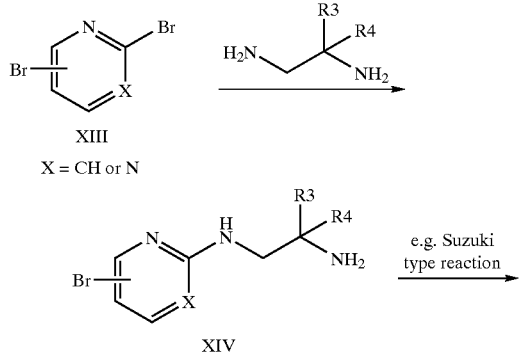

Amine derivatives IIIE can be prepared by the reaction of a dibromo-pyridine or pyrimidine derivative XIII with the appropriate 1,2-diaminoethane to form XIV. Subsequently, IIIE can be obtained by reaction of XIV with an appropriate phenyl or heteroaryl derivative in a Suzuki type reaction.

Scheme 2:

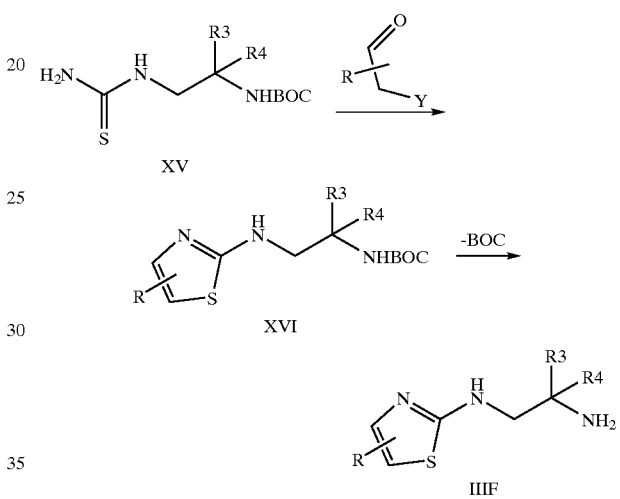

Amine derivatives IIIF can be prepared by the reaction of an optionally protected (2-amino-ethyl)-thiourea XV with an α-halo-carbonyl compound to form the corresponding N1-thiazol-2-yl-ethane-1,2-diamine XVI. Finally, deprotection leads to IIIF. The starting thiourea XV is known [R₃=R₄=H: CAS 331779-96-5] or can be derived in analogy from the corresponding diamine and benzoyl isothiocyanate.

Scheme 3:

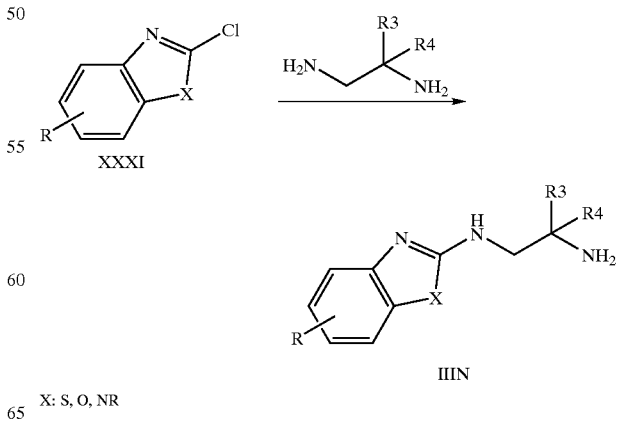

X: S, O, NR

Amine derivatives IIIN can be obtained if a chlorobenzthiazole, -benzoxazole, or -imidazole XXXI is treated with the appropriate 1,2-diaminoethane.

Scheme 4:

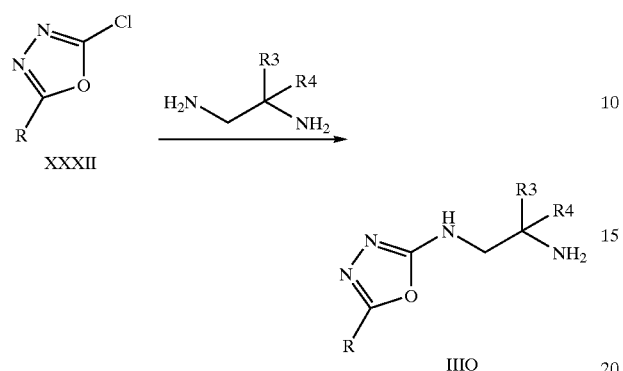

Amine derivatives IIIO can be obtained if 2-chloro-[1,3,4]oxadiazoles XXXII are treated with the appropriate 1,2-diaminoethanes. Starting [1,3,4]oxadiazoles are known or could be prepared in analogy to literature procedures (e.g. Singh, H. et al. *Ind. J. Chem.*, 1983, 22, 1177–1178 and Golfier, M. *J. Heterocycl. Chem.*, 1973, 10, 989).

Scheme 5:

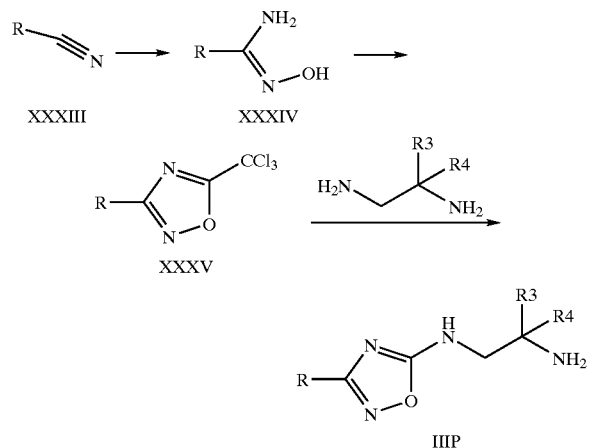

Amine derivatives IIIP can be obtained from nitrile derivatives XXXIII by conversion to the corresponding hydroxy-amidines XXXIV and subsequent cyclisation in the presence of trichloracetic anhydride and trichloracetic acid to the [1,2,4] oxadiazoles XXXV which are treated with the appropriate 1,2-diaminoethane.

Compounds of the formula (I) wherein $R^2$ is —C($R^3$, $R^4$)—(CH$_2$)$_n$—$R^5$ might require the synthesis of the corresponding amine precursors IIIA, IIIC, IIID, IIIG, IIIH, IIIK, IIIL, IIIM, IIIQ, IIIR, IIIS and IIIT. Preparation of these amine derivatives is described in the general schemes below:

Scheme 6:

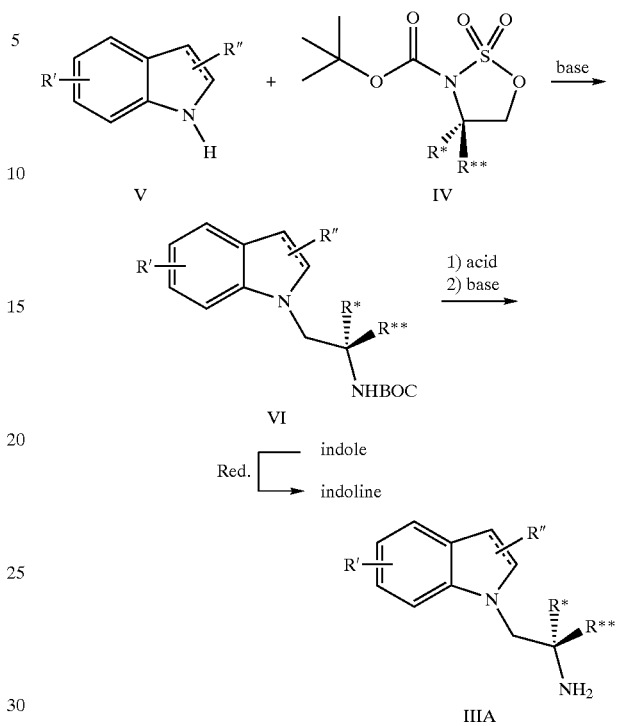

Amine derivatives IIIA can be obtained by reaction of indole derivatives V with a sulfimidate IV yielding intermediates VI that can subsequently be deprotected. Intermediates VI can optionally be reduced prior to the deprotection step. Sulfimidates represented by the general formula IV can be made from the suitably substituted α-amino acid. This starting material is reduced by methods known in the literature to give the corresponding 2-amino-alcohol. The intermediate thus obtained is then converted to the N-BOC protected derivative by standard methods. Further treatment with SOCl$_2$/imidazole and subsequent oxidation with NaIO$_4$/RuO$_2$ affords the desired sulfimidate IV.

Scheme 7:

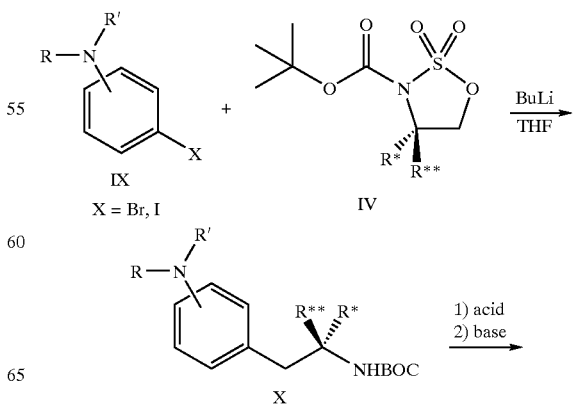

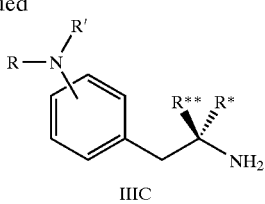

IIIC

Amine derivatives IIIC can be obtained from substituted aromatic bromides or iodides IX that are lithiated and further treated with a sulfimidate IV to yield the BOC protected intermediates X. These are then deprotected using methods known in the literature (Greene, T. W. et al. *Protective Groups in Organic Synthesis*; John Wiley &Sons, Inc.: New York, Chichester, Brisbane, Toronto, Singapore, 1991).

Scheme 8:

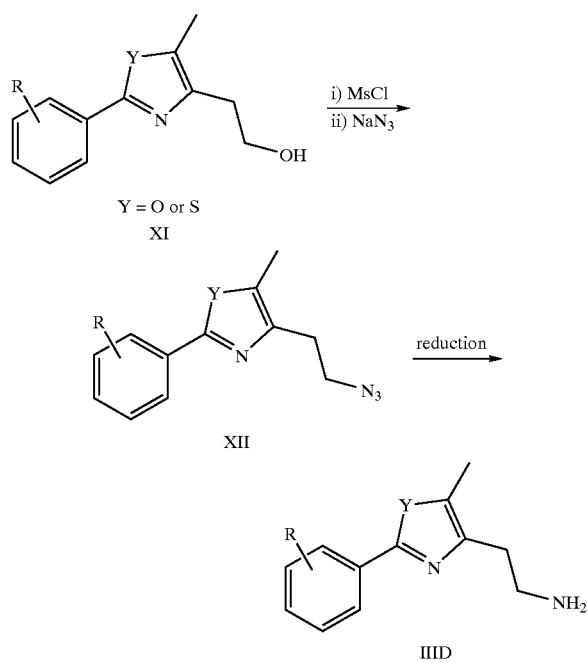

Amine derivatives IIID can be obtained by conversion of ethanol derivatives XI to the azide derivatives XII and subsequent reduction. The starting ethanol derivatives are known or were prepared from amides or thioamides in analogy to the procedures described in the literature (WO 00/08002 or Collins, J. L. et al. *J. Med. Chem.* 1998, 41, 5037–5054).

Scheme 9:

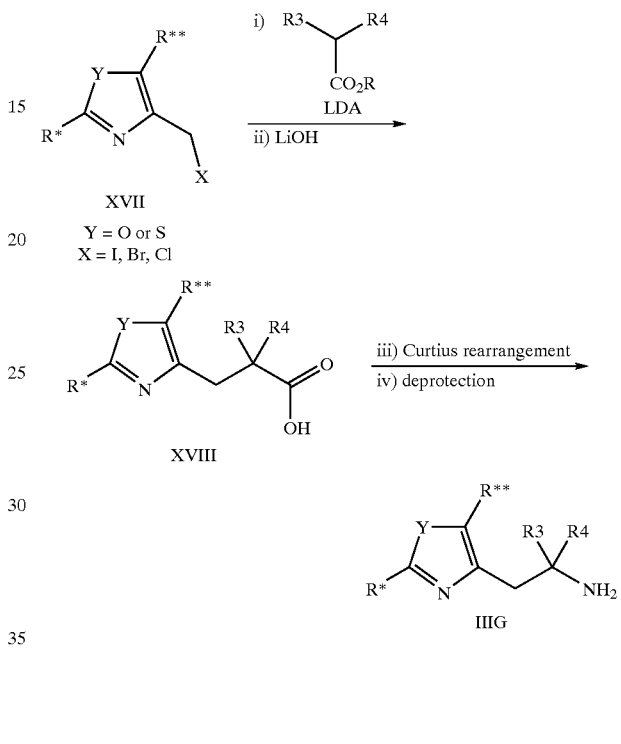

Amine derivatives IIIG can be obtained starting from the appropriate substituted halomethyl oxazole or thiazole derivatives XVII. Ester alkylation and subsequent saponification yielded the acid intermediates XVIII. These are subjected to a Curtius rearrangement. A final deprotection step resultes in the formation of the amines IIIG. The starting materials XVII are known or were prepared in analogy to the procedures described in the literature (WO 01/19805 A1, U.S. Pat. No. 545,531, *Chem. Pharm. Bull.* 1971, 19, 2050–2057 and *J. Med. Chem.* 1972, 15, 419–420).

Scheme 10:

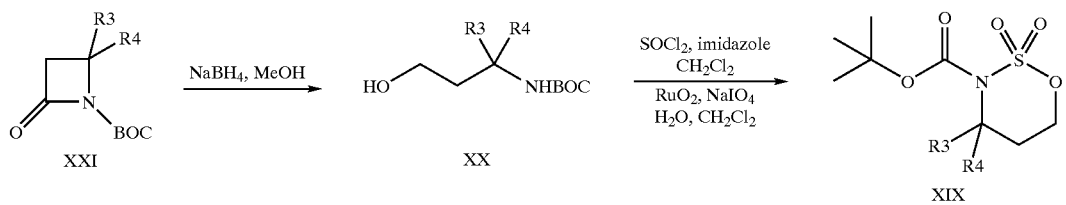

Pathway A:

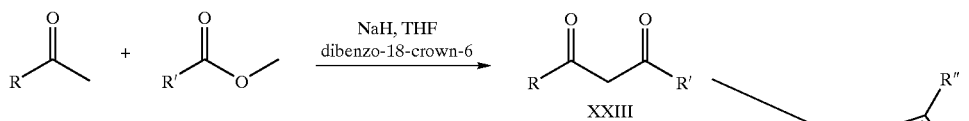

Pathway B:

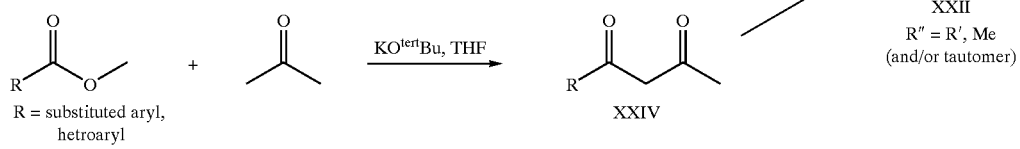

R = substituted aryl, hetroaryl

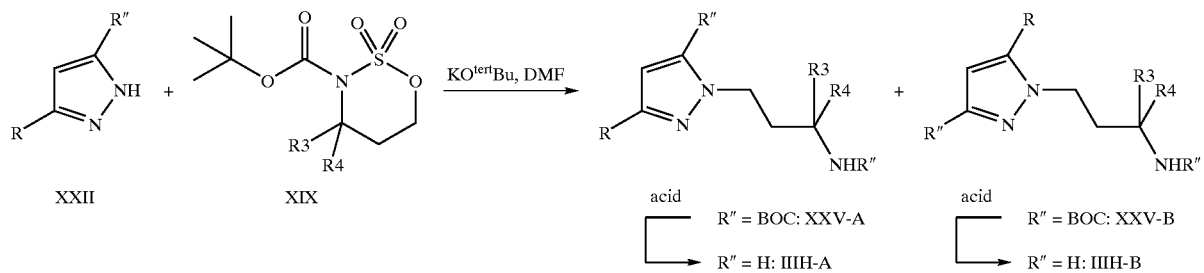

Amine derivatives IIIH-A and IIIH-B can be obtained by reaction of pyrazole derivaties XXII with sulfimidate reagents XIX and subsequent deprotection of the intermediates XXV-A and XXV-B. For the synthesis of the hitherto unknown 6-membered sulfimidate reagents XIX a BOC protected 3-aminopropan-1-ol XX (e.g. made by reduction from azetidinone XXI) is cyclized with SOCl$_2$ in the presence of imidazole. These intermediates are usually not isolated but subsequently oxidized to the BOC protected sulfonic acid derivatives XIX. As the 5 membered sulfimidates IV, these compounds are versatile alkylating agents that react readily with a variety of nitrogen and carbon based nucleophiles. Pyrazole derivatives XXII used are commercially available or can be accessed via pathways A or B known in the literature involving 1,3-diketones XXIII and XXIV as synthetic intermediates (e.g. Ali et al., *Pak. J. Sci. Ind. Res.* 1993, 36 (12), 502).

Scheme 11:

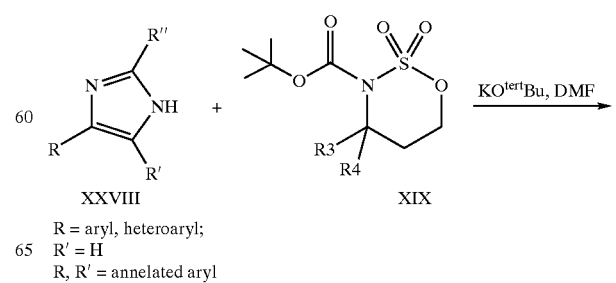

R: substituted aryl, heteroaryl

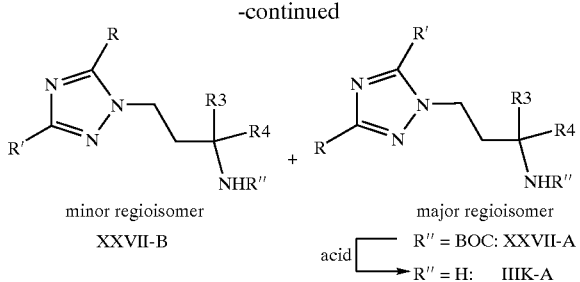

Amine derivatives IIIK-A (and IIIK-B) can be obtained by reaction of [1,2,4]triazole derivatives XXVI with sulfimidate reagents XIX and subsequent deprotection of the intermediates XXVII-A (and XXVII-B). [1,2,4]Triazoles XXVI used, are commercially available, known in the literature or were prepared in analogy to literature procedures (e.g. Francis et al., *Tetrahedron Lett.* 1987, 28 (43), 5133).

Scheme 12:

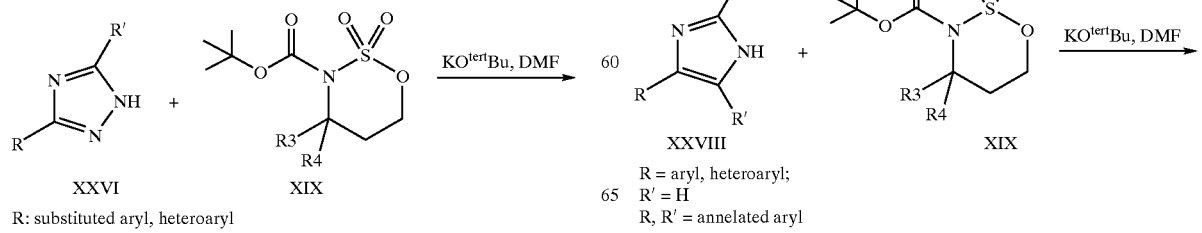

R = aryl, heteroaryl;
R' = H
R, R' = annelated aryl

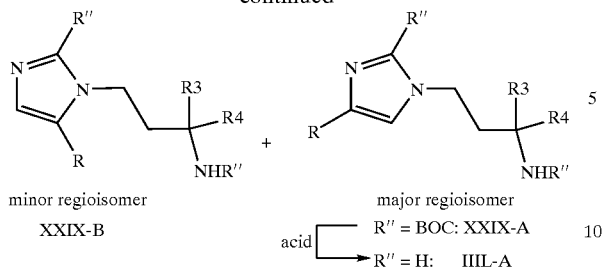

minor regioisomer XXIX-B   major regioisomer acid ⎡ R″ = BOC: XXIX-A
    ⎣ R″ = H: IIIL-A

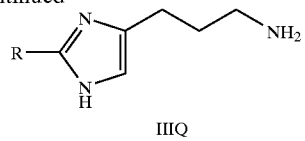

IIIQ

L = leaving group
PG = Protecting group

Amine derivatives IIIL-A (and IIIL-B) can be obtained by reaction of imidazole derivatives XXVII with sulfimidate reagents XIX and subsequent deprotection of the intermediates XXIX-A (and XXIX-B). Imidazoles XXVI used, are commercially available, known in the literature or were prepared in analogy to literature procedures (e.g. *Heterocycles* 1994, 39 (1), 139.

Amine derivatives IIIQ can be obtained by cyclization of amidine derivatives XXXVI with N-protected 4-oxo-pentylamine derivatives XXXVI activated at the primary 5-position. Amidines XXXVI are known in the literature or can be readily prepared from the corresponding nitrile derivatives employing standard methodologies as e.g. the Pinner reaction. N-protected 4-oxo-pentylamines XXXVII are known in the literature (Schunack, W. et al. Z. Naturforschung 1987, 42B, 238–242).

Scheme 13:

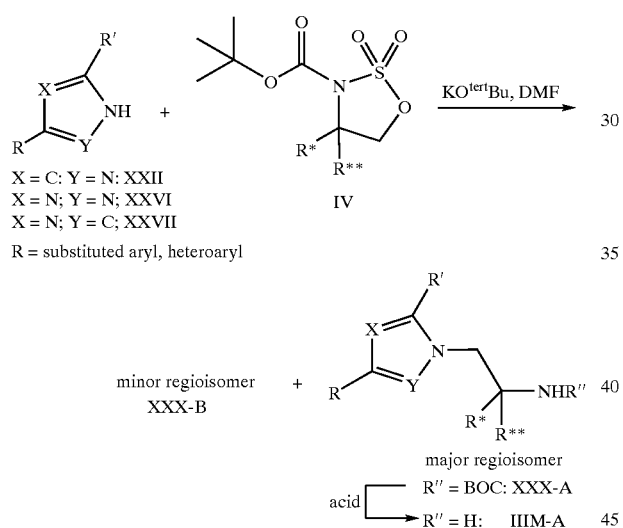

X = C; Y = N: XXII
X = N; Y = N; XXVI
X = N; Y = C; XXVII

R = substituted aryl, heteroaryl minor regioisomer XXX-B   major regioisomer acid ⎡ R″ = BOC: XXX-A
    ⎣ R″ = H: IIIM-A Amine derivatives IIIM-A (and IIIM-B) can be obtained by reaction of pyrazol derivatives XXII, [1,2,4]triazole derivatives XXVI and imidazole derivaties XXVII with sulfimidate reagents IV and subsequent deprotection of the intermediates XXX-A (and XXX-B). Starting pyrazols XXII, [1,2,4]triazoles XXVI and imidazols XXVIII are commercially available, are known or are prepared as described in the previous examples.

Scheme 14:

XXXVI + XXXVII → i) cyclization ii) deprotection

Scheme 15:

XXXVIII → i) azide formation ii) reduction → IIIR

Amine derivatives IIIR can be obtained from imidazoles XXXVIII via azide formation and reduction. Imidazoles XXXVIII are commercially available or can be prepared in analogy to literature procedures (WO 96/10018).

Scheme 16:

XXXVI + XXXIX → i) cyclization ii) deprotection → IIIS

L = leaving group
PG = Protecting group

Amine derivative IIIS can be obtained by cyclization of amidine derivatives XXXVI with N-protected 4-oxo-pentylamine derivatives XXXIX activated at the 3-position. Amidines XXXVI are known in the literature or can be readily prepared from the corresponding nitrile derivatives employing standard methodologies as e.g. the Pinner reaction. N-protected 4-oxo-pentylamines XXXIX are known in the literature (Schunack, W. et al. Z. Naturforschung 1987, 42B, 238–24).

Scheme 17:

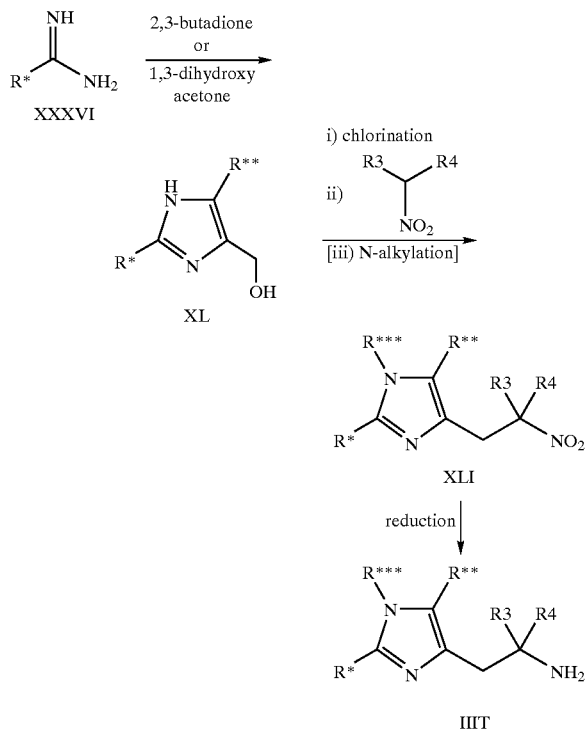

Amine derivatives IIIT can be obtained from imidazoles XL by chlorination, reaction with aliphatic nitro compounds under basic conditions (as for example described in *Eur. J. Med. Chem.* 1995, 30, 219–225) and subsequent reduction of the nitro intermediates XLI. Prior to the final reduction to the amine derivatives IIIT an N-alkylation step is optionally. Imidazoles XL are known or could be prepared from amidines XXXVI by reaction with 2,3-butadione or 1,3-dihydroxyacetone as described the literature (WO 96/10018 or in DE2528640).

Compounds of the formula (I) wherein $R^2$ is —C($R^3$, $R^4$)—CH$_2$—O—$R^7$ might require the synthesis of the corresponding amine precursors IIIB. Preparation of these amine derivatives is described in the general scheme below:

Scheme 18:

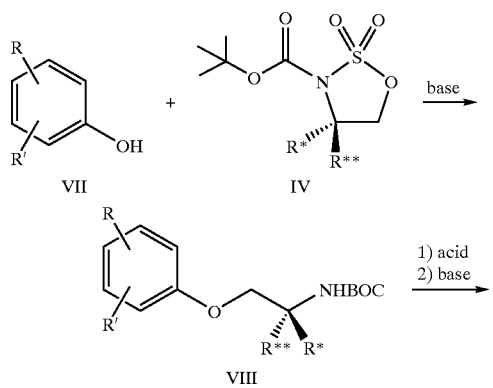

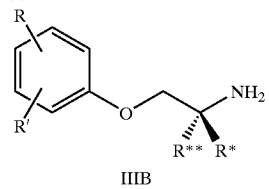

Amine derivatives IIIB can be obtained by reaction of phenol derivatives VII with a sulfimidate IV yielding intermediates VIII that can subsequently be deprotected.

EXAMPLES

Abbreviations:
BuLi=butyl lithium, BOC=tert-butyloxycarbonyl, THF=tetrahydrofuran, DIPEA=diisopropylethylamine (Huenig's base), LAH=lithium aluminium hydride, TFA=trifluoroacetic acid, RT=room temperature, MS=mass spectrometry, NMR=nuclear magnetic resonance spectroscopy, ISP=ion spray (positive ion) corresponds to ESI (electrospray, positive ion), TLC=thin layer chromatography, MsCl=methanesulphonyl chloride, Red.=reduction, TMS=tetramethylsilane, EI=electron ionization.

General Remarks:
$^1$H-NMR spectra were measured at 250 or 300 MHz in the solvent indicated in the example section. Chemical shifts are given in ppm relative to TMS. The remark (+Rotamer) indicates the presence of a second less intensive signal set in the spectrum that can be attributed to the rotamer. Mass spectra were taken with the ionization method indicated in the example section.

Example 1

(2S)-1-[((1R/S)-1,2,3,4-Tetrahydro-naphthalen-1-ylamino)-acetyl]-pyrrolidine-2-carbonitrile Racemic 1-amino-1,2,3,4-tetrahydronaphtalene (330 mg) was dissolved in dry THF (6 mL) under argon. A solution of IIA (130 mg) dissolved in 6 mL THF was added dropwise over a period of 5 hours at RT and the mixture was allowed to stir for another 20 hours. The resulting suspension was diluted with ethyl acetate and washed with saturated NaHCO$_3$ solution and brine. The organic layer was separated, dried over Na$_2$SO$_4$, filtered and evaporated. The residue was purified by flash chromatography (CH$_2$Cl$_2$/MeOH/NH$_4$OH 95:5:0.5) and the appropriate fractions were combined and evaporated to give the desired product as a mixture of two diastereomers (166 mg) as an oil.

MS (ISP): 284.2 (MH$^+$).
$^1$H-NMR (CDCl$_3$): 1.53 (broad s, 1H), 1.73 (m, 1H), 1.83 (m, 2H), 1.95–2.35 (m, 4H), 271 (m, 1H), 2.82 (m, 1H) m 3.42 m, 1H), 3.46 (s, 3H), 3.59 (m, 1H), 3.81 (m, 1H), 4.79 (m, 1H), 7.10 (m, 1H), 7.16 (m, 2H), 7.44 (m, 1H).

Example 2

(2S)-1-[((2R/S)-6-Methoxy-1,2,3,4-tetrahydro-naphthalen-2-ylamino)-acetyl]-pyrrolidine-2-carbonitrile, Hydrochloride Salt Step A]: 2-Amino-6-methoxy-1,2,3,4-tetrahydronaphtalene
6-Methoxy-3,4-dihydro-2(1H)-naphthalenone oxime (1.0 g) prepared from 6-methoxy-2-tetralone, according to Qizhuang, Y. et al. *J. Med. Chem.* 1989, 32, 478–486, was suspended in ethanol/water 1:1 and nickel-aluminium alloy (1.58 g) was added in portions. Sodium hydroxide solution (32%, 5.8 mL) was added drop by drop over a period of 5 minutes with intensive stirring—slight warming of the mixture was observed. The suspension was vigorously stirred and analyzed by TLC—all starting material had been consumed after 60 minutes. The suspension was filtered through dicalite and the filtrate extracted with CH$_2$Cl$_2$. The organic layer was washed with brine, dried and evaporated. The crude product was purified by flash chromatography (3*15 cm silica gel column) with CH$_2$Cl$_2$/MeOH/NH$_4$OH 95:5:0.5 and CH$_2$Cl$_2$/MeOH/NH$_4$OH 90:5:10.5 as eluents. The product was obtained as a dark green oil (660 mg).

MS(ISP): 178.1 (MH$^+$), 161.3 ([MH−NH$_3$]$^+$).

$^1$H-NMR (CDCl$_3$): 1.48 (broad s, 2H), 1.58 (m, 1H), 1.99 (m, 1H), 2.54 (dd, 1H), 2.80 (m, 2H), 2.96 (dd, 1H), 3.17 (m, 1H), 3.77 (s, 3H), 6.61 (d, 1H), 6.69 (dd, 1H), 7.00 (d, 1H).

Step B]: (2S)-1-[((2R/S)-6-Methoxy-1,2,3,4-tetrahydro-naphthalen-2-ylamino)-acetyl]-pyrrolidine-2-carbonitrile, Hydrochloride Salt The title compound was obtained in analogy to example 1 from racemic 2-amino-6-methoxy-1,2,3,4-tetrahydronaphthalene (357 mg) and IIA (116 mg). Yield: 156 mg. This compound was dissolved in THF/ether 1:3 (10 mL) and treated with 2.2 M HCl in ethyl acetate (1 ml). The resulting solid was isolated by filtration and dried in vacuo. Yield: 138 mg; mixture of 2 diastereomers.

MS (ISP): 314.4 (MH$^+$).

$^1$H-NMR (DMSO-d$_6$): 1.73 (m, 1H), 1H), 2.05 (m, 2H), 2.20 (m, 3H), 2.70 (m, 1H), 2.88 (m, 2H), 3.19 (m, 1H), 3.40 (m, 1H), 3.50 (q, 1H), 3.69 (m, 1H), 3.71 (s, 3H), 4.17 (m 2H), 4.87 (m, 1H), 6.66 (s, 1H), 6.73 (d, 1H), 7.02 (d, 1H), 9.18 (broad s, 2H).

Example 3

(2S)-1-[((2R/S)-1,2,3,4-Tetrahydro-naphthalen-1-ylamino)-acetyl]-pyrrolidine-2-carbonitrile Step A]: 2-Amino-1,2,3,4-tetrahydronaphtalene Racemic 2-amino-1,2,3,4-tetrahydronaphtalene was obtained in analogy to example 2, step A from β-tetralone oxime (CAS 3349-65-3).

$^1$H-NMR (CDCl$_3$): 1.48 (broad s, 2H), 1.60 (m, 1H), 2.01 (m, 1H), 2.56 (dd, 1H), 2.87 (m, 2H), 3.00 (dd, 1H), 3.19 (m, 1H), 7.10 (m, 4H).

Step B]: (2S)-1-[((2R/S)-1,2,3,4-Tetrahydro-naphthalen-2-ylamino)-acetyl]-pyrrolidine-2-carbonitrile This compound was obtained in analogy to example 1 from racemic 2-amino-1,2,3,4-tetrahydronaphtalene (153 mg) and IIB (75 mg). Yield: 83 mg, mixture of 2 diastereomers.

MS (ISP): 284.2 (MH$^+$).

$^1$H-NMR (CDCl$_3$): 1.66 (m, 1H), 1.87 (broad s, 1H), 2.00–2.40 (m, 5H), 2.67 (m, 1H), 2.75–3.05 (m, 5H), 3.46 (m, 1H), 3.52 (s, 2H), 3.62 (m, 1H), 4.78 (m, 1H), 7.10 (m, 4H).

Example 4

(2S)-1-{[(1S)-2-(5-Methoxy-2-methyl-indol-1-yl)-1-methyl-ethylamino]-acetyl}-pyrrolidine-2-carbonitrile, Hydrochloride Salt

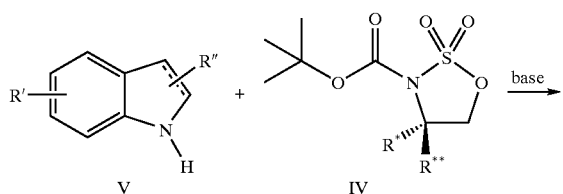

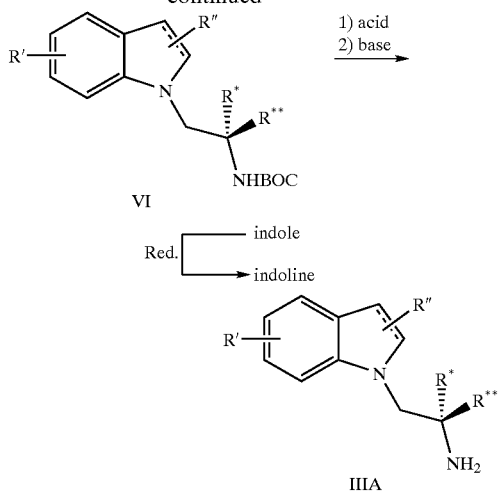

Synthesis of this compound requires the preparation of the corresponding amine precursor IIIA according to the general scheme shown above. In the initial step, an indole or indoline derivative V is treated with a suitable base such as NaH or potassium $^{tert}$butylate in an inert solvent such as THF or DMF or the like and then with a sulfimidate IV to give intermediate VI. Sulfimidates represented by the general formula TV can be made from the suitably substituted α-amino acid. This starting material is reduced by methods known in the literature to give the corresponding 2-amino-alcohol. The intermediate thus obtained is then converted to the N-BOC protected derivative by standard methods. Further treatment with SOCl$_2$/imidazole and subsequent oxidation with NaIO$_4$/RuO$_2$ affords the desired sulfimidate IV.

At this stage, reduction of the indole nucleus to the corresponding indoline can be carried out optionally by reduction with NaCNBH$_3$ or the like. The BOC protected intermediate VI is then deprotected using methods known in the literature (Greene, T. W. et al. Protective Groups in Organic Synthesis; John Wiley &Sons, Inc.: New York, Chichester, Brisbane, Toronto, Singapore, 1991) such as TFA/CH$_2$Cl$_2$ or HCl and the amine IIIA is liberated from its salt by base treatment.

Step A]: (S)-[2-(5-Methoxy-2-methyl-indol-1-yl)-1-methyl-ethyl]-carbamic Acid Tert-butyl Ester 5-Methoxy-2 methylindole (806 mg) was dissolved in DMF (25 mL) and cooled to 0° C. with an ice bath. Potassium tert-butylate (1M in THF, 6 mL) was added over 15 minutes and the resulting mixture was allowed to stir for further 30 minutes. (S)-4-Methyl-2,2-dioxo-[1,2,3] oxathiazolidine-3-carboxylic acid tert-butyl ester IV (1.42 g) was added in one portion and stirring was continued at RT until TLC analysis showed complete consumption of the starting material. The reaction mixture was partitioned between ether and saturated NH$_4$Cl solution and the organic layer was separated, washed with sat. NH$_4$Cl and brine, dried over Na$_2$SO$_4$, filtered and evaporated in vacuo. The residue was purified by flash chromatography (CH$_2$Cl$_2$). The appropriate fractions were combined and evaporated to give the product as an off-white solid (1.42 g).

MS (ISP): 341.3 (MNa$^+$), 319.4 (MH$^+$).

$^1$H-NMR (CDCl$_3$): 1.08 (d, 3H), 1.41 (s, 9H): 2.43 (s, 3H), 3.83 (s, 3H), 3.88 (m, 1H), 4.06 (m, 1H), 2.22 (broad m, 1H), 4.44 (broad s, 1H), 6.17 (s, 1H), 6.79 (dd, 1H), 6.98 (d, 1H), 7.26 (m, 1H). (+Rotamer).

Step B]: (S)-2-(5-Methoxy-2-methyl-indol-1-yl)-1-methyl-ethylamine

The product obtained in example 4, step A] (796 mg) was treated with TFA/CH$_2$Cl$_2$ 1:3 (25 mL) at 0 deg for 4 hours and then at RT for 1 hour with magnetic stirring. The mixture was concentrated in vacuo and the residue was taken up in ethyl acetate. The organic layer was washed twice with saturated NaHCO$_3$ and then with brine, dried (Na$_2$SO$_4$) and concentrated. The residue was purified by flash chromatography using CH$_2$Cl$_2$/MeOH/NH$_4$OH 95:5:0.5 as an eluent. Fractions containing pure product were combined and evaporated to give the desired compound (427 mg) as a yellow oil.

MS (ISP): 219.3 (MH$^+$), 202.2 ([MH–NH$_3$]$^+$).

$^1$H-NMR (CDCl$_3$): 1.13 (d, 3H), 1.15 (brad s, 2H), 2.43 (s, 3H). 3.35 (m, 1H), 3.84 (s, 3H), 3.87 (dd, 1H), 3.95 (dd, 1H), 6.18 (s, 1H), 6.78 (dd, 1H), 7.00 (d, 1H), 7.18 (d, 1H).

Step C]: (2S)-1-{[(1S)-2-(5-Methoxy-2-methyl-indol-1-yl)-1-methyl-ethylamino]-acetyl}-pyrrolidine-2-carbonitrile, Hydrochloride Salt α-Bromoamide IIB (50 mg) was treated with (S)-2-(5-Methoxy-2-methyl-indol-1-yl)-1-methyl-ethylamine (151 mg) according to example 1. The free amine thus obtained (66 mg) was converted to the hydrochloride salt as described in example 2.

MS (ISP): 377.3 (MNa$^+$), 355.3 (MH$^+$).

$^1$H-NMR (DMSO-d$_6$): 1.06 (d, 3H), 2.05 (m, 2H), 2.20 (m, 2H), 2.40 (s, 3H), 3.45 (q, 1H), 3.55 (m, 1H), 3.67 (m, 1H), 3.74 (s, 3H); 4.11 (m, 2H), 4.26 (m, 1H), 4.49 (m, 1H), 4.85 (m, 1H), 6.19 (s, 1H), 6.75 (d, 1H), 6.97 (s, 1H), 7.36 (d, 1H), 9.35 (broad s, 2H). (+Rotamer).

Example 5

(2S)-1-{[(1S)-2-(5-cyano-indol-1-yl)-1-methyl-ethylamino]-acetyl}-pyrrolidine-2-carbonitrile, Hydrochloride Salt Step A]: (S)-[2-(5-Cyano-indol-1-yl)-1-methyl-ethyl]-carbamic Acid Tert-butyl Ester This compound was obtained according to example 4, step A] from 5-cyanoindole (500 mg) and (S)-4-methyl-2,2-dioxo-[1,2,3]oxathiazolidine-3-carboxylic acid tert-butyl ester IV (1.0 g). Yield: 1.09 g, yellow solid.

MS (ISP): 317.4 (MNH$_4$$^+$).

$^1$H-NMR (CDCl$_3$): 1.12 (d, 3H), 1.41 (s, 9H), 3.95–4.20 (m, 2H), 4.20–4.40 (m, 2H), 6.59 (d, 1H), 7.18 (d, 1H), 7.40–7.60 (m, 2H), 7.96 (s, 1H).

Step B]: (S)-2-(5-Cyano-indol-1-yl)-1-methyl-ethylamine

The product obtained in step A] (500 mg) was treated with 2.2M HCl in ethyl acetate (15 mL) at RT for 60 minutes. After complete consumption of the starting material, the reaction mixture was diluted with ethyl acetate, washed with saturated NaHCO$_3$ solution and brine, dried, filtered and evaporated. The crude product was purified by flash chromatography using CH$_2$Cl$_2$/MeOH/NH$_4$OH 95:5:0.5 as an eluent. The fractions containing pure product were combined and evaporated to give the title compound as a colorless oil (251 mg).

MS (ISP): 200.2 (MH$^+$), 183.1 ([MH–NH$_3$]$^+$).

$^1$H-NMR (CDCl$_3$): 1.10 (broad s, 2H), 1.15 (d, 3H), 3.44 (m, 1H), 3.95 (dd, 1H), 4.11 (dd, 1H), 6.60 (d, 1H), 7.26 (d, 1H), 7.43 (m, 2H), 7.96 (d, 1H).

Step C]: (2S)-1-{[(1S)-2-(5-Cyano-indol-1-yl)-1-methyl-ethylamino]-acetyl}-pyrrolidine-2-carbonitrile, Hydrochloride Salt The amine formed in the previous step (215 mg) and IIB (80 mg) were coupled according to example 1. The resulting product was converted to the hydrochloride salt as described in example 2 step B], yielding 125 mg of the title compound.

MS (ISP): 358.3 (MNa$^+$), 336.2 (MH$^+$).

$^1$H-NMR (DMSO-d$_6$): 1.16 (d, 3H), 2.05 (m, 2H), 2.19 (m, 2H), 3.43 (m, 2H), 3.60 (m, 1H), 3.70 (m, 1H), 4.43 (dd, 1H), 4.74 (dd, 1H), 4.86 (m, 1H), 6.68 (d, 1H), 7.57 (d, 1H), 7.65 (d, 1H), 7.83 (d, 1H), 8.15 (s, 1H), 9.47 (broad s, 1H), 9.55 (broad s, 1H). (+Rotamer).

Example 6

(2S)-1-{[(1S)-1-Methyl-2-(2-methyl-indol-1-yl)-ethylamino]-acetyl}-pyrrolidine-2-carbonitrile The title compound was obtained from 2-methylindole, (S)-4-methyl-2,2-dioxo-[1,2,3]oxathiazolidine-3-carboxylic acid tert-butyl ester and IIB according to example 4, steps A] to C] as a brownish oil.

MS (ISP): 347.4 (MNa$^+$), 325.4 (MH$^+$).

$^1$H-NMR (CDCl$_3$): 1.56 (d, 3H), 1.74 (broad s, 1H), 1.80–2.20 (m, 4H), 2.49 (s, 3H), 2.59 (m, 1H), 2.69 (d, 1H), 2.96 (d, 1H), 3.08 (m, 1H), 3.19 (m, 1H), 4.02 (m, 2H), 4.57 (m, 1H); 6.25 (s, 1H), 7.00–7–17 (m, 2H), 7.28 (m, 1H), 7.48 (d, 1H). (+Rotamer).

Example 7

(2S)-1-{[(1S)-2-(2,3-Dimethyl-indol-1-yl)-1-methyl-ethylamino]-acetyl}-pyrrolidine-2-carbonitrile This compound was obtained from 2,3-dimethylindole, (S)-4-methyl-2,2-dioxo-[1,2,3]oxathiazolidine-3-carboxylic acid tert-butyl ester and IIB according to example 5, steps A] to C].

MS (ISP): 361.3 (MNa$^+$), 339.3 (MH$^+$).

$^1$H-NMR (DMSO-d$_6$):0.95 (d, 3H), 1.85–2.10 (m, 5H), 2.18 (s, 3H), 2.35 (s, 3H), 3.02 (m, 1H), 3.15 (m, 1H), 3.24 (broad s, 2H), 3.39 (m, 1H), 3.93 (dd, 1H), 4.07 (dd, 1H), 4.65 (m, 1H), 6.95 (t, 1H), 7.02 (t, 1H), 7.36 (m, 2H). (+Rotamer).

Example 8

(2S)-1-{[(1S)-1-Methyl-2-(3-methyl-indol-1-yl)-ethylamino]-acetyl}-pyrrolidine-2-carbonitrile, Hydrochloride Salt This compound was made from 3-methyl-indole, (S)-4-methyl-2,2-dioxo-[1,2,3]oxathiazolidine-3-carboxylic acid tert-butyl ester and IIA according to example 5, steps A] to C]. The hydrochloride salt of the title compound was obtained according to example 2.

MS (ISP): 347.4 (MNa$^+$), 325.4 (MH$^+$).

$^1$H-NMR (DMSO-d$_6$): 1.15 (d, 3H), 2.04 (m, 2H); 2.17 (m, 2H), 2.26 (s, 3H); 3.40 (m, 2H); 3.54 (m, 1H); 3.66 (m, 2H); 4.05 (broad s, 2H); 4.24 (dd, 1H); 4.58 (dd, 1H); 4.84 (dd, 1H); 7.06 (m, 1H); 7.18 (m, 2H); 7.52 (m, 2H), 9.23 (broad s, 1H); 9.30 (broad s, 1H). (+Rotamer).

Example 9

(2S)-1-{[(1S)-2-(5-Brom-indol-1-yl)-1-methyl-ethylamino]-acetyl}-pyrrolidine-2-carbonitrile This compound was obtained from 5-bromo-indole, (S)-4-methyl-2,2-dioxo-[1,2,3]oxathiazolidine-3-carboxylic acid tert-butyl ester and IIA according to example 5, steps A] to C].

MS (ISP): 411.5 (MNa$^+$), 389.2 (MH$^+$).

$^1$H-NMR (DMSO-d$_6$): 0.92 (d, 3H), 1.95 (m, 2H), 2.07 (m, 2H), 3.02 (m, 1H), 3.22 (m, 1H), 3.28 (broad s, 2H), 3.42 (m, 1H), 4.04 (dd, 1H), 4.16 (dd, 1H), 4.68 (t, 1H), 6.42 (d, 1H), 7.21 (dd, 1H), 7.42 (d, 1H), 7.49 (d, 1H), 7.72 (d, 1H). (+Rotamer).

Example 10
(2S)-1-{[2-(5-Brom-2,3-dihydro-indol-1-yl)-ethylamino]-acetyl}-pyrrolidine-2-carbonitrile, Hydrochloride Salt This compound was made from 5-brom-2,3-dihydroindole, 2,2-dioxo-[1,2,3]oxathiazolidine-3-carboxylic acid tert-butyl ester according to example 5, steps A] to C]. The hydrochloride salt of the title compound was obtained according to example 2.

MS (ISP): 399.3 (MNa$^+$), 377.3 (MH$^+$).

$^1$H-NMR (DMSO-d$_6$): 2.05 (m, 2H), 2.17 (m, 2H); 2.94 (t, 2H), 3.16(m, 2H), 3.38 (m, 5H), 3.60 (m, 1H), 4.00–4.30 (m, 5H), 4.85 (t, 1H), 6.55 (d, 1H), 7.20 (d, 2H), 7.21 (s, 1H), 9.10 (broad s, 2H). (+Rotamer).

Example 11
(2S)-1-{[(1S)-2-(7-aza-indol-1-yl)-1-methyl-ethylamino]-acetyl}-pyrrolidine-2-carbonitrile This compound was made from 7-azaindole, (S)-4-methyl-2,2-dioxo-[1,2,3]oxathiazolidine-3-carboxylic acid tert-butyl ester and IIB according to example 5, steps A] to C].

MS (ISP): 334.3 (MNa$^+$), 312.2 (MH$^+$).

$^1$H-NMR (DMSO-d$_6$): 0.93 (d, 3H), 1.97 (m, 2H), ~2.0 (very broad s, 1H), 2.08 (m, 2H), 3.12 (m, 1H), 3.20–3.40 (m, 3H), 3.49 (m, 1H), 4.14 (dd, 1H), 4.27 (dd, 1H), 4.69 (t, 1H), 6.46 (d, 1H), 7.07 (dd, 1H), 7.55 (d, 1H), 7.95 (d, 1H), 8.23 (d, 1H). (+Rotamer).

Example 12
(2S)-1-{[(1S)-2-(2-aza-indol-1-yl)-1-methyl-ethylamino]-acetyl}-pyrrolidine-2-carbonitrile This compound was made from 2-azaindole (indazole), (S)-4-methyl-2,2-dioxo-[1,2,3]oxathiazolidine-3-carboxylic acid tert-butyl ester and IIB according to example 5, steps A] to C].

MS (ISP): 334.3 (MNa$^+$), 312.2 (MH$^+$).

$^1$H-NMR (DMSO-d$_6$): 0.95 (d, 3H), 1.95 (m, 2H), ~2.0 (very broad s, 1H), 2.08 (m, 2H), 3.12 (m, 1H), 3.20–3.40 (m, 3H), 3.45 (M, 1H), 4.27 (dd, 1H), 4.40 (dd, 1H), 4.68 (t, 1H), 7.12 (t, 1H), 7.37 (t, 1H), 7.69 (d, 1H), 7.75 (d, 1H), 8.07 (s, 1H). (+Rotamer).

Example 13
(2S)-1-{[(1S)-1-Methyl-2-(5-phenyl-2,3-dihydro-indol-1-yl)-ethylamino]-acetyl}-pyrrolidine-2-carbonitrile This compound was obtained from 5-phenyl-2,3-dihydroindole (synthesized from 5-bromoindole according to WO 95/01976), (S)-4-methyl-2,2-dioxo-[1,2,3]oxathiazolidine-3-carboxylic acid tert-butyl ester and IIA according to example 4, steps A] to C].

MS (ISP): 389.3 (MH$^+$).

$^1$H-NMR (CDCl$_3$): 1.13 (d, 3H), 1.70 (broad s, 1H), 2.10–2.35 (m, 4H), 2.89 (m, 1H), 3.06 m, 3H), 3.17 (dd, 1H), 3.27 (q, 1H), 3.35–3.70 (m, 5H), 4.76 (m, 1H), 6.56 (d, 1H), 7.20–7.40 (m, 5H), 7.51 (d, 1H). (+Rotamer).

Example 14
(2S)-1-{[(1S)-2-(5-cyano-2-methyl-indol-1-yl)-1-methyl-ethylamino]-acetyl}-pyrrolidine-2-carbonitrile This compound was obtained from 5-cyano-2-methyl-indole (synthesized in analogy to Aggarwal, A. et al. *Synth. Commun.* 1993, 23, 1101–1110, from 5-bromo-2-methylindole), (S)-4-methyl-2,2-dioxo-[1,2,3] oxathiazolidine-3-carboxylic acid tert-butyl ester and IIA according to example 5, steps A] to C] with the exception that in step C] a reaction time of 72 hours had to be applied in order to achieve an acceptable yield.

MS (ISP): 350.4 (MH$^+$).

$^1$H-NMR (CDCl$_3$): 1.15 (d, 3H), 1.60 (broad s, 1H), 1.95–2.30 (m, 4H), 2.51 (s, 3H), 2.82 (d, 1H), 2.86 (m, 1H), 3.01 (d, 1H), 3.05–3.25 (m, 2H), 4.02 (m, 2H), 4.63 (m, 1H), 6.35 (s, 1H), 7.36 (m, 2H), 7.84 (s, 1H). (+Rotamer).

Example 15
(2S)-1-{[(1S)-1-Methyl-2-(2-phenyl-indol-1-yl)-ethylamino]-acetyl}-pyrrolidine-2-carbonitrile This compound was obtained from 2-phenylindole, (S)-4-methyl-2,2-dioxo-[1,2,3]oxathiazolidine-3-carboxylic acid tert-butyl ester and IIA according to example 5, steps A] to C].

MS (ISP): 387.3 (MH$^+$).

$^1$H-NMR (DMSO-d$_6$): 0.69 (d, 3H), 1.93 (m, 2H), 2.07 (m, 2H), 2.80 (m, 1H), 2.91 (d, 1H), 3.02 (m, 1H), 3.05 (d, 1H), 3.31 (m, 1H), 4.06 (dd, 1H), 4.28 (dd, 1H), 4.61 (dd, 1H), 6.52 (s, 1H), 7.05 (t, 1H), 7.16 (t, 1H), 7.40–7.62 (m, 7H). (+Rotamer).

Example 16
(2S)-1-[((1S)-2-Carbazol-9-yl-1-methyl-ethylamino)-acetyl]-pyrrolidine-2-carbonitrile This compound was obtained from carbazole, (S)-4-methyl-2,2-dioxo-[1,2,3]oxathiazolidine-3-carboxylic acid tert-butyl ester and IIA according to example 5, steps A] to C] as the free base.

MS (ISP): 361.3 (MH$^+$).

$^1$H-NMR (DMSO-d$_6$): 0.98 (d, 3H), 1.90 (m, 2H), 2.06 (m, 2H), 3.21 (m, 2H), 3.30–3.5 (m, 4H), 4.23 (dd, 1H), 4.39 (dd, 1H), 4.63 (dd, 1H), 7.19 (t, 2H), 7.44 (t, 2H), 7.63 (d, 2H), 8.14 (d, 2H). (+Rotamer).

Example 17
(2S)-1-{[(1S)-2-(6-Brom-indol-1-yl)-1-methyl-ethylamino]-acetyl}-pyrrolidine-2-carbonitrile The title compound was obtained from 6-brom-indole, (S)-4-methyl-2,2-dioxo-[1,2,3]oxathiazolidine-3-carboxylic acid tert-butyl ester and IIA according to example 5, steps A] to C] as the free base.

MS (ISP): 411.3 (MNa$^+$), 389.1 (MH$^+$)

$^1$H-NMR (DMSO-d$_6$): 0.94 (d, 3H), 1.85–2.15 (m, 5H), 3.02 (m, 1H), 3.20–3.40 (m, 4H), 3.43 (m, 1H), 4.04 (dd, 1H), 4.15 (dd, 1H), 4.67 (t, 1H), 6.45 (d, 1H), 7.12 (dd, 1H), 7.39 (d, 1H), 7.49 (d, 1H), 7.77 (s, 1H). (+Rotamer).

Example 18
(2S)-1-{[(1S)-1-Methyl-2-(7-methyl-indol-1-yl)-ethylamino]-acetyl}-pyrrolidine-2-carbonitrile This compound was obtained from 7-methyl-indole, (S)-4-methyl-2,2-dioxo-[1,2,3]oxathiazolidine-3-carboxylic acid tert-butyl ester and IIA according to example 5, steps A] to C] as the free base.

MS (ISP): 347.4 (MNa$^+$), 325.4 (MH$^+$)

$^1$H-NMR (DMSO-d$_6$): 0.94 (d, 3H), 1.85–2.10 (m, 5H); 2.67 (s, 3H), 2.96 (m, 1H); 3.10–3.23 (m, 3H), 3.38 (m, 1H), 4.15 (dd, 1H), 4.32 (dd, 1H), 4.66 (m, 1H), 6.39 (d, 1H), 6.86 (m, 2H), 7.26 (d, 1H), 7.36 (d, 1H). (+Rotamer).

Example 19
(2S)-1-{[(1S)-2-(7-Brom-indol-1-yl)-1-methyl-ethylamino]-acetyl}-pyrrolidine-2-carbonitrile This compound was obtained from 7-brom-indole, (S)-4-methyl-2,2-dioxo-[1,2,3]oxathiazolidine-3-carboxylic acid tert-butyl ester and IIA according to example 5, steps A] to C] as the free base.

MS (ISP): 411.3 (MNa$^+$), 389.1 (MH$^+$)

$^1$H-NMR (DMSO-d$_6$): 0.94 (d, 3H), 1.85–2.10 (m, 5H), 3.00–3.30 (m, 4H), 3.41 (m, 1H), 4.41 (m, 2H), 4.66 (m,

1H), 6.50 (d, 1H), 6.92 (t, 1H), 7.31 (d, 1H), 7.41 (d, 1H), 7.57 (d, 1H). (+Rotamer).

Example 20
(2S)-1-{[2-(4-Chlor-indol-1-yl)-ethylamino]-acetyl}-pyrrolidine-2-carbonitrile This compound was obtained from 4-chlor-indole, 2,2-dioxo-[1,2,3]oxathiazolidine-3-carboxylic acid tert-butyl ester and IIA according to example 5, steps A] to C] as the free base.

MS (ISP): 331.3 (MH$^+$)

$^1$H-NMR (CDCl$_3$): ~1.70 (broad s, 1H), 2.00–2.30 (m, 4H), 3.05–3.70 (m, 6H), 4.26 (t, 2H), 4.66 (m, 1H), 6.61 (d, 1H), 7.12 (m, 2H), 7.22 (d, 1H), 7.27 (m, 1H).

Example 21
(2S)-1-{[2-(5-Methoxy-2-methyl-indol-1-yl)-ethylamino]-acetyl}-pyrrolidine-2-carbonitrile This compound was obtained from 5-methoxy-2-methyl-indole, 2,2-dioxo-[1,2,3]oxathiazolidine-3-carboxylic acid tert-butyl ester and IIA according to example 5, steps A] to C] as the free base.

MS (ISP): 363.3 (MNa$^+$), 341.4 (MH$^+$).

$^1$H-NMR (CDCl$_3$): 1.60 (broad s, 1H), 2.00–2.30 (m, 4H), 2.44 (s, 3H), 2.99 (t, 2H), 3.07–3.40 (m, 3H), 3.83 (s, 3H), 4.18 (t, 2H), 4.68 (m, 1H), 6.16 (s, 1H), 6.78 (dd, 1H), 6.89 (d, 1H); 7.18 (d, 1H).

Example 22
(2S)-1-{[(1S)-2-(5,6-Dimethoxy-indol-1-yl)-1-methyl-ethylamino]-acetyl}-pyrrolidine-2-carbonitrile This compound was obtained from 5,6-dimethoxindole, (S)-4-methyl-2,2-dioxo-[1,2,3]oxathiazolidine-3-carboxylic acid tert-butyl ester and IIB according to example 4, steps A] to C] with the following exception in step B]: The desired intermediate 1-methyl-2-[5,6-dimethoxy-indol-1-yl] was obtained in only 25% yield. The major product was (S)-1-[1-(2-amino-propyl)-5,6-dimethoxy-1H-indol-3-yl]-2,2,2-trifluoro-ethanone (50% yield).

MS (ISP): 371.3 (MH$^+$).

$^1$H-NMR (CDCl$_3$): 1.16 (d, 3H), 1.68 (broad s, 1H), 1.90–2.21 (m, 4H), 2.80 (m, 2H), 2.02 (d, 1H), 2.20 (m, 2H), 3.91 (s, 3H), 3.94 8s, 3H), 3.95 (m, 2H), 4.62 (m, 1H), 6.39 (d, 1H), 6.85 (s, 1H), 7.02 (d, 1H), 7.06 (s, 1H).

Example 23
(2S)-1-{[(1S)-2-(5,6-Dimethoxy-3-trifluoroacetyl-indol-1-yl)-1-methyl-ethylamino]-acetyl}-pyrrolidine-2-carbonitrile, Hydrochloride Salt (S)-1-[1-(2-Amino-propyl)-5,6-dimethoxy-1H-indol-3-yl]-2,2,2-trifluoro-ethanone, obtained in example 22, Step B] was coupled with IIB according to example 1.

MS (ISP): 467.2 (MH$^+$).

$^1$H-NMR (DMSO-d$_6$): 1.21 (d, 3H), 2.05 (m, 2H), 2.19 (m, 2H), 3.37 (m, 2H), 3.46 (m, 1H), 3.59 (m, 1H), 3.77 (m, 1H), 3.83 (s, 3H), 3.90 (s, 3H), 4.10 (m, 2H), 4.55 (m, 1H), 4.78 (m, 1H), 4.86 (m, 1H), 7.49 (s, 1H), 7.68 (s, 1H), 8.45 (s, 1H), 9.37 (broad s, 1H), 9.55 (broad s, 1H).

Example 24
(2S)-1-({(1S)-2-[6-(4-Methoxy-phenyl)-2,3-dihydro-indol-1-yl]-1-methyl-ethylamino}-acetyl)-pyrrolidine-2-carbonitrile Step A]: (S)-{2-[6-(4-Methoxy-phenyl)-indol-1-yl]-1-methyl-ethyl}-carbamic Acid Tert-butyl Ester This compound was synthesized from 6-(4-methoxy-phenyl)-indole (synthesized from 6-bromo-indole according to Carrera, G. M. et al. *Synlett* 1994, 1, 93–94) and (S)-4-methyl-2,2-dioxo-[1,2,3]oxathiazolidine-3-carboxylic acid tert-butyl ester as described in example 4, step A].

MS (ISP): 381.4 (MH$^+$).

Step B]: (S)-{2-[6-(4-Methoxy-phenyl)-2,3-dihydro-indol-1-yl]-1-methyl-ethyl}-carbamic-acid tert-butyl ester (S)-{2-[6-(4-Methoxy-phenyl)-indol-1-yl]-1-methyl-ethyl}-carbamic acid tert-butyl ester (1.80 g) was dissolved in acetic acid (25 mL) and CH$_2$Cl$_2$ (10 mL) and cooled to 0° C. NaCNBH$_3$ (1.41 g) was added in portions and the resulting mixture was allowed to stir for 4 hours. The reaction mixture was diluted with ethyl acetate and extracted with concentrated NaOH solution. The organic layer was washed with brine, dried (Na$_2$SO$_4$) and evaporated. The residue was purified by flash chromatography (gradient of ethyl acetate in hexanes) to give the title compound as a brown oil (1.7 g).

MS (ISP): 405.6 (MNa$^+$), 383.4 (MH$^+$).

$^1$H-NMR (CDCl$_3$): 1.25 (d, 3H), 1.41 (s, 9H), 3.01 (t, 2H), 3.12 (d, 2H), 3.46 (m, 2H), 3.84 (s, 3H), 3.94 (m, 1H), 4.57 (broad s, 1H), 6.62 (s, 1H), 6.82 (d, 1H), 6.94 (m, 2H), 7.10 (d, 1H), 7.49 (m, 2H).

Step C]: (S)-2-[6-(4-Methoxy-phenyl)-2,3-dihydro-indol-1-yl]-1-methyl-ethylamine The title compound was obtained from (S)-{2-[6-(4-methoxy-phenyl)-indol-1-yl]-1-methyl-ethyl}-carbamic acid tert-butyl ester according to example 4, step B] as a gum.

MS (ISP): 283.4 (MH$^+$).

$^1$H-NMR (CDCl$_3$): 1.20 (d, 3H), 2.88 (dd, 1H), 2.96 (m, 2H), 3.14–3.29 (m, 4H), 3.51 (m, 1H), 3.83 (s, 3H), 6.70 (s, 1H), 6.85 (d, 1H), 6.94 (m, 2H), 7.06 (d, 1H), 7.49 (m, 2H).

Step D]: (2S)-1-({(1S)-2-[6-(4-Methoxy-phenyl)-2,3-dihydro-indol-1-yl]-1-methyl-ethylamino}-acetyl)-pyrrolidine-2-carbonitrile The title compound was obtained from (S)-{2-[6-(4-methoxy-phenyl)-2,3-dihydro-indol-1-yl]-1-methyl-ethylamine and IIA in analogy to example 1 as a foam.

MS (ISP): 419.5 (MH$^+$).

$^1$H-NMR (CDCl$_3$): 1.12 (d, 3H), 2.00–2.31 (m, 4H), 2.45 (very broad s, 1H), 2.89 (dd, 1H), 3.04 (m, 3H), 3.18 (dd, 1H), 3.27 (m, 1H), 3.35–3.70 (m, 5H), 3.84 (s, 3H), 4.75 (m, 1H), 6.65 (s, 1H), 6.83 (d, 1H), 6.94 (m, 2H), 7.10 (d, 1H), 7.48 (m, 2H). (+Rotamer).

Example 25
(2S)-1-{[(1S)-1-Methyl-2-(naphthalen-2-yloxy)-ethylamino]-acetyl}-pyrrolidine-2-carbonitrile

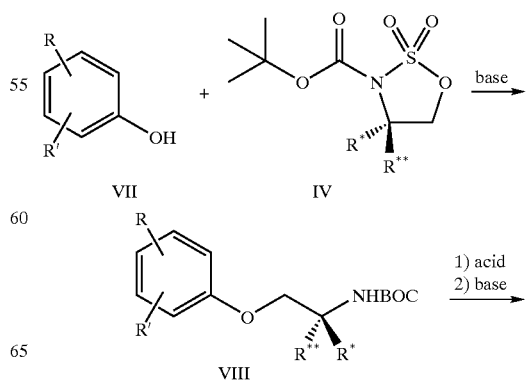

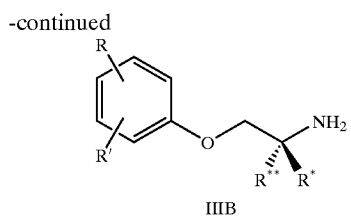

Synthesis of this compound requires the preparation of the corresponding amine precursor IIIB according to the general scheme shown above. In the initial step, an aminophenol or naphtol derivative VII is treated with a suitable base such as NaH or potassium *tert*butylate in an inert solvent such as THF or DMF or the like and then with a sulfimidate IV. Sulfimidates represented by the general formula IV can be made from the suitably substituted α-amino acid. This starting material is reduced by methods known in the literature to give the corresponding 2-amino-alcohol. The intermediate thus obtained is then converted to the N-BOC protected derivative by standard methods. Further treatment with SOCl$_2$/imidazole and subsequent oxidation with NaIO$_4$/RuO$_2$ affords the desired sulfimidate IV.

The resulting BOC protected intermediate VIII is then deprotected using methods known in the literature (Greene, T. W. et al. *Protective Groups in Organic Synthesis*; John Wiley &Sons, Inc.: New York, Chichester, Brisbane, Toronto, Singapore, 1991) such as TFA/CH$_2$Cl$_2$ or HCl and the amine IIIB is liberated from its salt by base treatment.

Step A]: (S)-[1-Methyl-2-(naphthalen-2-yloxy)-ethyl]-carbamic Acid Tert-Butyl Ester β-Naphthol (721 mg) was dissolved in DMF (25 mL) and cooled to 0° C. Potassium-tert-butylate (1M in THF, 6.0 mL) was added drop by drop over a periode of 15 minutes and the mixture was stirred for 30 min. (S)-4-Methyl-2,2-dioxo-[1,2,3]oxathiazolidine-3-carboxylic acid tert-butyl ester (IV, 1.42 g) was added in one portion and stirring was continued for 3 hours. The reaction mixture was poured into 1M NH$_4$Cl and extracted with ether. The organic phase was washed with 1M NH$_4$Cl and brine, dried over Na$_2$SO$_4$ and evaporated to yield a yellow solid. The crude product was purified by flash chromatography (ethyl acetate/hexanes 1:9) to give the desired product as a colorless solid (1.5 g).

MS (ISP): 324.3 (MNa$^+$), 302.3 (MH$^+$).

$^1$H-NMR (CDCl$_3$): 1.38 (d, 3H), 1.46 (s, 9H), 4.00–4.20 (m, 3H), 4.82 (broad s, 1H), 7.14 (m, 2H), 7.34 (m, 1H), 7.44 (m, 1H), 7.74 (m, 3H).

Step B]: (S)-1-Methyl-2-(naphthalen-2-yloxy)-ethyl-amine

Removal of the BOC protecting group from the material obtained in the previous step (610 mg) was accomplished using the TFA/CH$_2$Cl$_2$ method as described in example 4, step B]. Colorless solid, 268 mg.

MS (ISP): 202.2 (MH$^+$).

$^1$H-NMR (CDCl$_3$): 1.21 (d, 3H), 1.53 (broad s, 2H), 3.41 (m, 1H), 3.80 (dd, 1H), 3.99 (dd, 1H), 7.10–7.20 (m, 2H), 7.33 (t, 1H), 7.43 (t, 1H), 7.70–7.80 (m, 3H).

Step C]: (2S)-1-{[(1S)-1-Methyl-2-(naphthalen-2-yloxy)-ethylamino]-acetyl}-pyrrolidine-2-carbonitrile The title compound was obtained from (S)-1-methyl-2-(naphthalen-2-yloxy)-ethyl-amine (139 mg) and IIB (50 mg) following the procedure outlined in example 1. Flash chromatography furnished a colorless glass (75 mg).

MS (ISP): 360.2 (MNa$^+$), 338.2 (MH$^+$).

$^1$H-NMR (CDCl$_3$): 1.24 (d, 3H), 1.85 (broad s, 1H); 2.00–2.40 (m, 4H), 3.21 (m, 1H), 3.40–3.80 (m, 4H), 4.00 (m, 2H), 4.77 (m, 1H), 7.10–7.20 (m, 2H), 7.33 (t, 1H), 7.43 (t, 1H), 7.70–7.80 (m, 3H). (+Rotamer).

Example 26
(2S)-1-{[2-(quinolin-6-yloxy)-ethylamino]-acetyl}-pyrrolidine-2-carbonitrile This compound was obtained in analogy to example 25, steps A] to C] from 6-hydroxyquinoline, 2,2-dioxo-[1,2,3] oxathiazolidine-3-carboxylic acid tert-butyl ester and IIB with the following modification in step B]: The amine intermediate obtained in this step was very water soluble and could not be isolated by extraction. The aqueous phase was therefore neutralized with solid NaHCO$_3$ and the solvent was removed in high vacuum. The resulting solid was suspended in ethanol, stirred for 1 hour and then filtered. The filtrate was concentrated in vacuo and the residue was purified by flash chromatography to give the free amine III that was used in the final coupling step.

MS (ISP): 347.4 (MNa$^+$), 325.4 (MH$^+$).

$^1$H-NMR (CDCl$_3$): 1.75 (broad s, 1H), 2.10–2.30 (m, 4H), 3.15 (m, 2H), 3.45 (m, 1H), 3.54 (s, 2H), 3.63 (m, 1H), 4.21 (m, 2H), 4.76 (m, 1H), 7–08 (d, 1H), 7.33–7.41 (m, 2H), 7.99 (D, 1H), 8.04 (D, 1H), 8.77 (m, 1H). (+Rotamer).

Example 27
(2S)-1-{[2-(3-N,N-dimethylamino-phenoxy)-ethylamino]-acetyl}-pyrrolidine-2-carbonitrile This compound was obtained in analogy to example 25, steps A] to C] from 3-N,N-dimethylaminophenol, 2,2-dioxo-[1,2,3]oxathiazolidine-3-carboxylic acid tert-butyl ester and IIB.

MS (ISP): 329.3 (MNa$^+$), 317.3 (MH$^+$).

$^1$H-NMR (CDCl$_3$): 1.60 (broad s, 1H), 2.00–2.35 (m, 4H), 2.93 (s, 6H), 3.05 (m, 2H), 3.43 (m, 1H), 3.47 (s, 2H), 3.62 (m, 1H), 4.08 (m, 2H), 4.75 (m, 1H), 6.28 (m, 2H), 6.36 (m, 1H), 7.13 (t, 1H). (+Rotamer).

Example 28
(2S)-1-{[-(1S)-2-(4-N,N-dimethylamino-phenyl)-1-methyl-ethylamino]-acetyl}-pyrrolidine-2-carbonitrile

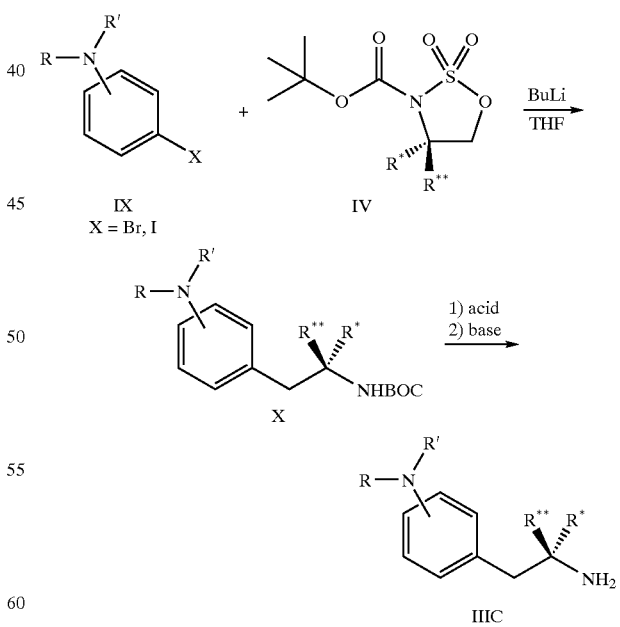

Synthesis of this compound requires the preparation of the corresponding amine precursor IIIC according to the general scheme shown above. A substituted aromatic bromide or iodide IX is treated with BuLi in an inert solvent such as THF at low temperature (−100 to 0° C.). The lithiated species thus generated is then further treated with a sulfimidate IV and BOC protected intermediate X is obtained. Compound X is then deprotected using methods known in the literature (Greene, T. W. et al. *Protective Groups in Organic Synthesis*; John Wiley &Sons, Inc.: New York, Chichester, Brisbane, Toronto, Singapore, 1991) such as TFA/CH$_2$Cl$_2$ or HCl and the amine with the general formula IIIC is liberated from its salt by base treatment.

Step A]: (S)-[2-(4-N,N-Dimethylamino-phenyl)-1-methyl-ethyl]-carbamic Acid Tert-butyl Ester 4-Brom-N,N-dimethylaniline (1.0 g) was dissolved in dry THF (17 mL) and cooled to −78 deg with a dry ice/acetone bath. BuLi (1.6 M in hexanes, 3.75 mL) was added dropwise by means of a syringe and a colorless precipitate was observed after addition. The mixture was allowed to stir for 20 min and then (S)-4-methyl-2,2-dioxo-[1,2,3]oxathiazolidine-3-carboxylic acid tert-butyl ester (1.54 g) was added in one portion. The suspension was stirred at −78 deg for 30 mins and then the excess solid dry ice was removed and the mixture allowed to warm to −30° C. over a period of 60 min. The suspension gradually cleared to give a slightly hazy yellow solution. This was quenched by addition of saturated NH$_4$Cl solution and extracted with CH$_2$Cl$_2$ (heavy emulsion). The organic layer was washed with brine (emulsion) and dried over Na$_2$SO$_4$. The organic layer gradually turned dark blue. The solvent was removed in vacuo and the residue was purified by flash chromatography (CH$_2$Cl$_2$ and then CH$_2$Cl$_2$/MeOH 95:5) to give the title compound as a light brown solid (563 mg).

MS (ISP): 301.3 (MNa$^+$), 279.2 (MH$^+$).

$^1$H-NMR (CDCl$_3$): 1.06 (d, 3H), 1.43 (s, 9H), 2.56 (dd, 1H), 2.74 (dd, 1H), 2.92 (s, 6H), 4.84 (broad s, 1H), 4.37 (broad s, 1H), 6.69 (d, 2H), 7.04 (d, 2H).

Step B]: (S)-2-(4-N,N-Dimethylamino-phenyl)-1-methyl-ethyl-amine

Removal of the BOC protecting group of the compound prepared in the previous step (150 mg) was accomplished according to example 4, step B] with TFA/CH$_2$Cl$_2$ (10 mL). Colorless solid: 75 mg.

MS (ISP): 179.1 (MH$^+$).

$^1$H-NMR (CDCl$_3$): 1.05 (d, 3H), 1.32 (broad s, 2H), 2.40 (dd, 1H), 2.63 (dd, 1H), 2.91 (S, 6H), 3.09 (m, 1H), 6.70 (d, 2H), 7.06 (d, 2H).

Step C]: (2S)-1-{[(1S)-2-(4-N,N-dimethylamino-phenyl)-1-methyl-ethylamino]-acetyl}-pyrrolidine-2-carbonitrile The title compound was obtained from (S)-2-(4-N,N-dimethylamino-phenyl)-1-methyl-ethyl-amine (124 mg) and IIB (50 mg) following the procedure outlined in example 1. Flash chromatography furnished a colorless solid (67 mg).

MS (ISP): 337.2 (MNa$^+$), 315.3 (MH$^+$).

$^1$H-NMR (CDCl$_3$): 1.06 (d, 3H), 2.08–2.30 (m, 5H), 2.50–2.68 (m, 2H), 2.86 (m, 1H), 2.91 (s, 6H), 3.28–3.60 (m, 4H), 4.74 (m, 1H), 6.69 (d, 2H), 7.06 (d, 2H).

Example 29

(2S)-1-{[(1R)-2-(4-N,N-dimethylamino-phenyl)-1-methyl-ethylamino]-acetyl}-pyrrolidine-2-carbonitrile This compound was obtained in analogy to example 28, steps A] to C] from 4-bromo-N,N-dimethylaniline, (R)-4-methyl-2,2-dioxo-[1,2,3]oxathiazolidine-3-carboxylic acid tert-butyl ester and IIB as a colorless solid.

MS (ISP): 337.3 (MNa$^+$), 315.4 (MH$^+$).

$^1$H-NMR (CDCl$_3$): 1.06 (d, 3H), 1.15 (very broad s, 1H), 2.08–2.30 (m, 4H), 2.53 (dd, 1H), 2.60 (dd, 1H), 2.87 (m, 1H), 2.91 (s, 6H), 3.30–3.50 (m, 4H), 4.74 (m, 1H), 6.69 (d, 2H), 7.06 (d, 2H). (+Rotamer).

Example 30

(2S)-1-{[(1S)-2-(3-N,N-dimethylamino-phenyl)-1-methyl-ethylamino]-acetyl}-pyrrolidine-2-carbonitrile This compound was obtained in analogy to example 28, steps A] to C] from 3-bromo-N,N-dimethylaniline, (S)-4-methyl-2,2-dioxo-[1,2,3]oxathiazolidine-3-carboxylic acid tert-butyl ester and IIB as a yellow gum.

MS (ISP): 315.4 (MH$^+$).

$^1$H-NMR (CDCl$_3$): 1.10 (d, 3H), 1.85 (broad s, 1H), 2.00–2.33 (m, 4H), 2.65 (m, 2H), 2.94 (s, 6H), 3.90–3.01 (m, 1H), 3.25–3.57 (m, 4H), 4.72 (m, 1H), 6.56–6.62 (m, 3H), 7.17 (t, 1H). (+Rotamer).

Example 31

(2S)-1-{[2-(5-Methyl-2-phenyl-oxazol-4-yl)-ethylamino]-acetyl}-pyrrolidine-2-carbonitrile

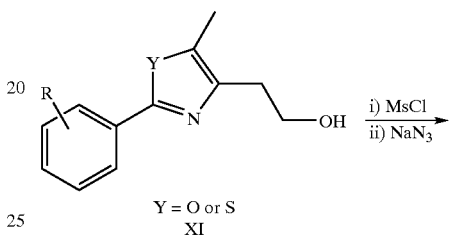

Y = O or S
XI

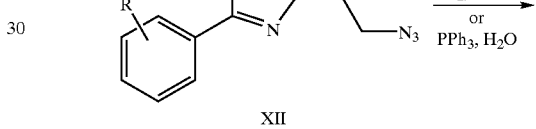

XII

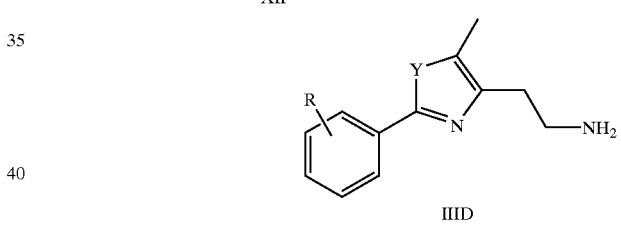

IIID

Synthesis of this compound requires the preparation of the corresponding amine precursor IIID in three steps starting from ethanol derivative XI according to the general scheme above. Reaction of XI with i) methanesulfonyl chloride, ii) sodium azide and subsequent reduction of the azide derivative XII using either triphenylphosphine/water or hydrogen in presence of palladium/carbon resulted in the formation of amine IIID as the free base or its salt. The starting ethanol derivatives are known or were prepared from amides or thioamides in analogy to the procedures described in WO 00/08002 or Collins, J. L. et al. *J. Med. Chem.* 1998, 41, 5037–5054.

Step A]: 4-(2-Azido-ethyl)-5-methyl-2-phenyl-oxazole 2-(5-Methyl-2-phenyl-oxazol-4-yl)-ethanol [CAS 103788-65-4, commercially available] (2.1 g) and DIPEA (2.6 ml) were dissolved in CH$_2$Cl$_2$ and the mixture was cooled to 0° C. Then methanesulfonyl chloride (0.85 ml) was added and stirring was continued for 4 hours at 0° C. After dilution with CH$_2$Cl$_2$ the reaction mixture was washed with water and brine and the organic layer was dried with MgSO$_4$. Filtration and evaporation of the solvent yielded a residue (2.81 g), which was redissolved in DMF (20 ml). Sodium azide (0.78 g) was added and the reaction mixture was heated to 60° C. for 4 hours. Then water was added and the resulting mixture was extracted three times with ethyl acetate. The combined extracts were washed with water and brine and dried with MgSO$_4$. After filtration and evaporation of the solvent the residue was purified by chromatography (hexane/ethyl acetate 1:1) to give the desired product as a light yellow oil (2.2 g).

MS (EI): 228.1 (M$^+$).

$^1$H-NMR (DMSO-d$_6$): 2.37 (s, 3H), 2.77 (t, 2H), 3.59 (t, 2H), 7.51 (m, 3H), 7.69 (m, 2H).

Step B]: 4-(2-Amino-ethyl)-5-methyl-2-phenyl-oxazole

The azide derivative prepared according to step A] (5.25 g) was dissolved in a mixture of MeOH (200 ml) and conc. HCl (20 ml). Then a catalytic amount of 10% palladium/carbon was added and the reaction vessel was charged with hydrogen. After complete consumption of the starting material (as indicated by TLC), the catalyst was filtered off and most of the MeOH was removed from the filtrate. The remaining mixture was diluted with water, washed with ethyl acetate and the pH of the aqueous phase was then adjusted to 10 by addition of solid sodium carbonate. The aqueous phase was extracted three times with ethyl acetate and the combined organic layers were washed with brine and dried over MgSO$_4$. Filtration and evaporation of the solvent yielded the title compound (4.6 g) as a brown solid.

$^1$H-NMR (CDCl$_3$): 1.39 (broad s, 2H+H$_2$O), 2.35 (s, 3H), 2.63 (t, 2H), 3.03 (t, 2H), 7.42 (m, 3H), 7.99 (m, 2H).

Step C]: (2S)-1-{[2-(5-Methyl-2-phenyl-oxazol-4-yl)-ethylamino]-acetyl}-pyrrolidine-2-carbonitrile The title compound was obtained from the amine derivative prepared according to step B] (2.6 g) and IIA (0.74 g) following the procedure outlined in example 1. Final chromatography (ethyl acetate/MeOH 2:1) gave a light yellow oil (1.1 g).

MS (ISP): 339.3 (MH$^+$).

$^1$H-NMR (DMSO-d$_6$): 2.00 (m, 2H), 2.10 (m, 3H), 2.34 (s, 3H), 2.60 (t, 2H), 2.80 (t, 2H), 3.39 (m, 3H), 3.53 (m, 1H), 4.74 (m, 1H), 7.49 (m, 3H), 7.90 (d, 2H). (+Rotamer).

Example 32

(2S)-1-({2-[2-(4-Fluoro-phenyl)-5-methyl-oxazol-4-yl]-ethylamino}-acetyl)-pyrrolidine-2-carbonitrile This compound was prepared in analogy to example 31, steps A] to C] starting from 2-[2-(4-fluoro-phenyl)-5-methyl-oxazol-4-yl]-ethanol [CAS 196810-30-7]. It was obtained as light brown oil.

MS (ISP): 357.4 (MH$^+$).

$^1$H-NMR (DMSO-d$_6$): 2.00 (m, 2H), 2.13 (m, 3H), 2.33 (s, 3H), 2.59 (t, 2H), 2.79 (t, 2H), 3.38 (m, 3H), 3.55 (m, 1H), 4.73 (dd, 1H), 7.34 (t, 2H), 7.94 (dd, 2H). (+Rotamer).

Example 33

(2S)-1-({2-[2-(4-Benzyloxy-phenyl)-5-methyl-oxazol-4-yl]-ethylamino}-acetyl)-pyrrolidine-2-carbonitrile This compound was prepared in analogy to example 31 starting from 2-[2-(4-benzyloxy-phenyl)-5-methyl-oxazol-4-yl]-ethanol. The starting material was prepared from 4-benzyloxy-benzamide [CAS 56442-43-4, commercially available] and 4-bromo-3-oxopentanoate as described with 4-fluoro-benzamide in Collins, J. L. et al. *J. Med. Chem.* 1998, 41, 5037–5054. Steps A] and C] were performed as outlined in example 31 but the azide to amine conversion in step B] was done alternatively:

To a solution of 4-(2-azido-ethyl)-2-(4-benzyloxy-phenyl)-5-methyl-oxazole (660 mg) in THF (10 ml) were added water (0.3 ml) and triphenylphosphine (570 mg). The reaction mixture was stirred over night at RT. Then the solvent was removed and the residue was purified by chromatography (CH$_2$Cl$_2$/MeOH 4:1) yielding 2-[2-(4-benzyloxy-phenyl)-5-methyl-oxazol-4-yl]-ethylamine (380 mg) as a white solid.

MS (ISP): 309.0 (MH$^+$).

$^1$H-NMR (DMSO-d$_6$): 1.49 (broad s, 2H), 2.31 (s, 3H), 2.47 (m, 2H), 2.77 (t, 2H), 5.16 (s, 2H), 7.12 (d, 2H), 7.36–7.49 (m, 5H), 7.83 (d, 2H).

After step C] the title compound was obtained as light brown oil.

MS (ISP): 446.2 (MH$^+$).

$^1$H-NMR (DMSO-d$_6$): 1.99 (m, 2H), 2.12 (m, 3H), 2.31 (s, 3H), 2.57 (t, 2H), 2.78 (t, 2H), 3.38 (m, 3H), 3.55 (m, 1H), 4.73 (dd, 1H), 5.17 (s, 2H), 7.12 (d, 2H), 7.36–7.49 (m, 5H), 7.83 (d, 2H). (+Rotamer).

Example 34

(2S)-1-({2-[2-(2-Ethoxy-4-fluoro-phenyl)-5-methyl-oxazol-4-yl]-ethylamino}-acetyl)-pyrrolidine-2-carbonitrile This compound was prepared in analogy to example 31 starting from 2-[2-(2-ethoxy-4-fluoro-phenyl)-5-methyl-oxazol-4-yl]-ethanol. The starting material was prepared from 4-fluoro-2-hydroxy-benzamide [CAS 1643-77-2] by reaction with ethyl bromide in presence of a base in analogy to a procedure described in Freedman, J. et al. *J. Heterocycl. Chem.* 1990, 27, 343-6 and then reaction with 4-bromo-3-oxopentanoate as described with 4-Fluoro-benzamide in Collins, J. L. et al. *J. Med. Chem.* 1998, 41, 5037–5054. Steps A] to C] yielded the title compound as light brown oil.

MS (ISP): 402.1 (MH$^+$).

$^1$H-NMR (DMSO-d$_6$): 1.35 (t, 3H), 2.00 (m, 2H), 2.12 (m, 2H), 2.29 (s, 3H), 2.58 (t, 2H), 2.76 (t, 2H), 3.37 (m, 3H), 3.57 (m, 1H), 4.13 (q, 2H), 4.73 (dd, 1H), 6.86 (dt, 1H), 7.06 (dd, 1H), 7.78 (dd, 1H). (+Rotamer).

Example 35

(2S)-1-({2-[2-(4-Chloro-phenyl)-5-methyl-oxazol-4-yl]-ethylamino}-acetyl)-pyrrolidine-2-carbonitrile This compound was prepared in analogy to example 31 starting from 2-[2-(4-chloro-phenyl)-5-methyl-oxazol-4-yl]-ethanol. The starting material was prepared from 4-chloro-benzamide and 4-Bromo-3-oxopentanoate as described with 4-Fluoro-benzamide in Collins, J. L. et al. *J. Med. Chem.* 1998, 41, 5037–5054. Steps A] and C] were performed as outlined in example 31, step B] was done according to example 33. The title compound was obtained as light brown oil.

MS (ISP): 391.2 (MH$^+$).

$^1$H-NMR (DMSO-d$_6$): 2.00 (m, 2H), 2.12 (m, 2H), 2.34 (s, 3H), 2.60 (t, 2H), 2.79 (t, 2H), 3.40 (m, 4H), 3.56 (m, 1H), 4.73 (dd, 1H), 7.56 (d, 2H), 7.90 (d, 2H). (+Rotamer).

Example 36

(2S)-1-({2-[5-(4-Methoxy-phenyl)-pyridin-2-ylamino]-1,1-dimethyl-ethylamino}-acetyl)-pyrrolidine-2-carbonitrile, Hydrochloride Salt XIII
X = CH or N

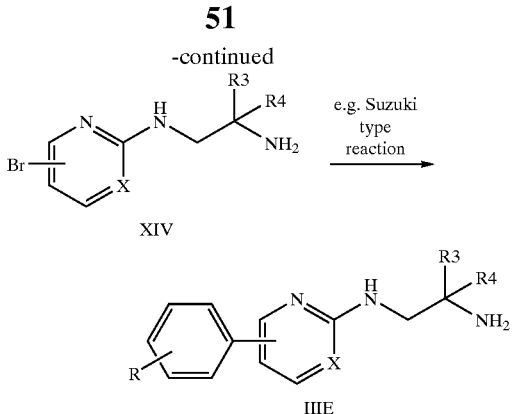

Synthesis of this compound requires the preparation of the corresponding amine precursor IIIE. A possible way for the preparation of IIIE is described in the general scheme above. According to this scheme a dibromo-pyridine or pyrimidine derivative XIII is treated with the appropriate 1,2-diaminoethane. Subsequently, IIIE can be obtained by conversion of XIV with the appropriate phenyl derivative in a Suzuki type reaction.

Step A1: N1-(5-Bromo-pyridin-2-yl)-2-methyl-propane-1,2-diamine

A solution of 2,5-dibromopyridine (1.7 g) and pyridine (0.75 ml) in 1,2-diamino-2-methlypropane (8.5 ml) was heated 5 hours at 140° C. After cooling to RT, the solvent was evaporated. Flash chromatography (100 g silica gel; $CH_2Cl_2$/MeOH/$NH_4OH$ 85:14.5:0.5) provided 1.8 g of a dark red oil.

MS(ISP): 244.2 and 246.2 ($M^+$).
$^1$H-NMR (DMSO-$d_6$): 1.03 (s, 6H), 2.7 (broad s, 2H), 3.16 (d, 2H), 6.56 (d, 1H), 6.66 (t, 1H), 7.48 (dd, 1H), 7.97 (d, 1H).

Step B]: N1-[5-(4-Methoxy-phenyl)-pyridin-2-yl]-2-methyl-propane-1,2-diamine

A solution of 4-methoxyphenylboronic acid (1.6 g) in EtOH (25 ml) and an aqueous solution of $Na_2CO_3$ (6.3 g in 34 ml) were added to a solution of N1-(5-bromo-pyridin-2-yl)-2-methyl-propane-1,2-diamine (1.7 g) and tetrakis(triphenylphosphine)palladium(0) (0.81 g) in DME (50 ml). The mixture was stirred 6 h at 85° C. The mixture was concentrated to approximately 20 ml. Ethyl acetate and 1N NaOH were added. After stirring 20 minutes insoluble parts were filtered off. The aqueous layer was extracted with ethyl acetate. The organic layers were washed with brine, combined, dried ($MgSO_4$) and evaporated. Flash chromatography (silica gel; $CH_2Cl_2$/MeOH/$NH_4OH$ 80:19:1) followed by crystallization from ether and ethyl acetate provided 1.24 g of colorless crystals.

MS(ISP): 272.3 ($MH^+$), 255.2 (($MH-NH_3$)$^+$).
$^1$H-NMR (DMSO-$d_6$): 1.04 (s, 6H), 1.9 (broad s, 2H), 3.20 (d, 2H), 3.77 (s, 3H), 6.44 (t, 1H), 6.62 (d, 1H), 6.96 (d, 2H), 7.47 (d, 2H), 7.62 (dd, 1H), 8.20 (d, 1H).

Step C]: (2S)-1-({2-[5-(4-Methoxy-phenyl)-pyridin-2-ylamino]-1,1-dimethyl-ethylamino}-acetyl)-pyrrolidine-2-carbonitrile, Hydrochloride Salt The title compound was obtained from N1-[5-(4-methoxy-phenyl)-pyridin-2-yl]-2-methyl-propane-1,2-diamine (0.60 g) and IIA (0.15 g) following the procedure outlined in example 1, whereas DMF was used as solvent. The residue obtained by flash chromatography was dissolved in THF and precipitated by treatment with HCl and ether yielding 0.35 g of a light yellow powder.

MS(ISP): 408.5 ($MH^+$).
$^1$H-NMR (DMSO-$d_6$): 1.39 (s, 6H), 1.95–2.13 (m, 2H), 2.21 (m, 2H), 3.60 (m, 1H), 3.74 (m, 2H), 3.80 (s, 3H), 3.85–4.30 (m, 5H), 4.87 (dd, 1H), 7.04 (d, 2H), 7.2 (broad s, 1H), 7.58 (m, 3H), 8.17 (broad s, 1H), 9.32 (broad s, 1H). (+Rotamer)

Example 37

(2S)-1-({2-[5-(4-Methoxy-phenyl)-pyridin-2-ylamino]-ethylamino}-acetyl)-pyrrolidine-2-carbonitrile, Hydrochloride Salt This compound was obtained in analogy to example 36, steps A] to C] starting from 2,5-dibromopyridine, 1,2-diaminoethane, 4-methoxyphenylboronic acid and IIA. It was isolated as a white powder.

MS(ISP): 380.5 ($MH^+$).
$^1$H-NMR (DMSO-$d_6$): 1.95–2.13 (m, 2H), 2.18 (m, 2H), 3.24 (m, 2H), 3.46 (m, 1H), 3.64 (m, 1H), 3.80 (s, 3H), 3.82 (m, 2H), 4.19 (m, 2H), 4.4 (very broad s, 2H), 4.86 (dd, 1H), 7.04 (d, 2H), 7.12 (broad s, 1H), 7.61 (m, 2H), 8.18 (broad s, 2H), 9.39 (broad s, 2H). (+Rotamer)

Example 38

1-({2-[5-(4-Methoxy-phenyl)-pyridin-2-ylamino]-ethylamino}-acetyl)-pyrrolidine

This compound was prepared in analogy to example 36, steps A1 to C1 starting from 2,5-dibromopyridine, 1,2-diaminoethane, 4-methoxyphenylboronic acid and IIC. It was isolated as a white powder.

MS(ISP): 355.3 ($MH^+$).
$^1$H-NMR (DMSO-$d_6$): 1.79 (m, 2H), 1.89 (m, 2H), 3.09 (t, 2H), 3.45 (m, 4H), 3.56 (q, 2H), 3.78 (s, 3H), 3.91 (s, 2H), 6.61 (d, 1H), 6.88 (t, 1H), 6.99 (d, 2H), 7.49 (d, 2H), 7.71 (dd, 1H), 8.24 (d, 1H), 8.55 (broad s, 2H). (+Rotamer)

Example 39

(2S)-1-({2-[5-(3-Methoxy-phenyl)-pyridin-2-ylamino]-ethylamino}-acetyl)-pyrrolidine-2-carbonitrile, Hydrochloride Salt This compound was prepared in analogy to example 36, steps A] to C] starting from 2,5-dibromopyridine, 1,2-diaminoethane, 3-methoxyphenylboronic acid and IIA. It was isolated as a colorless glass.

$^1$H-NMR (DMSO-$d_6$): 1.95–2.10 (m, 2H), 2.20 (m, 2H), 3.26 (m, 2H), 3.47 (m, 1H), 3.64 (m, 1H), 3.83 (s, 3H), 3.88 (m, 2H), 4.0 (very broad s, 2H), 4.19 (m, 2H), 4.85 (dd, 1H), 6.98 (d, 1H), 7.24 (m, 3H), 7.41 (t, 1H), 8.27 (m, 2H), 9.43 (broad s, 2H). (+Rotamer)

Example 40

(2S)-1-({2-[5-(2-Methoxy-phenyl)-pyridin-2-ylamino]-ethylamino}-acetyl)-pyrrolidine-2-carbonitrile, Hydrochloride Salt This compound was prepared in analogy to example 36, steps A] to C] starting from 2,5-dibromopyridine, 1,2-diaminoethane, 2-methoxyphenylboronic acid and IIA. It was isolated as a white powder.

MS(ISP): 380.5 ($MH^+$).
$^1$H-NMR (DMSO-$d_6$): 1.95–2.10 (m, 2H), 2.18 (m, 2H), 3.25 (m, 2H), 3.47 (m, 1H), 3.6 (very broad s, 2H), 3.60 (m, 1H), 3.80 (s, 3H), 3.80 (m, 2H), 4.18 (m, 2H), 4.86 (dd, 1H), 7.10 (m, 3H), 7.37 (m, 2H), 8.06 (m, 2H), 9.42 (broad s, 2H). (+Rotamer)

Example 41

(2S)-1-({2-[5-(4-Cyano-phenyl)-pyridin-2-ylamino]-ethylamino}-acetyl)-pyrrolidine-2-carbonitrile, Hydrochloride Salt This compound was prepared in analogy to example 36, steps A] to C] starting from 2,5-dibromopyridine, 1,2-diaminoethane, 4-cyanophenylboronic acid and IIA. It was isolated as a white powder.

MS(ISP): 375.5 (MH⁺).
¹H-NMR (DMSO-d₆): 1.95–2.10 (m, 2H), 2.18 (m, 2H), 3.25 (m, 2H), 3.49 (m, 1H), 3.62 (m, 1H), 3.87 (m, 2H), 4.18 (m, 2H), 4.0 (very broad s, 2H), 4.85 (dd, 1H), 7.18 (d, 1H), 7.91 (d, 2H), 7.95 (d, 2H), 8.28 (d, 1H), 8.38 (s, 1H), 9.42 (broad s, 2H). (+Rotamer)

Example 42
(2S)-1-({2-[5-Phenyl-pyridin-2-ylamino]-ethylamino}-acetyl)-pyrrolidine-2-carbonitrile This compound was prepared in analogy to example 36, steps A] to C] starting from 2,5-dibromopyridine, 1,2-diaminoethane, phenylboronic acid and IIA. It was isolated as its free amine, as a colorless gum.
MS(ISP): 350.5 (MH⁺).
¹H-NMR (DMSO-d₆): 1.90–2.05 (m, 2H), 2.12 (m, 2H), 2.73 (m, 2H), 3.25–3.45 (m, 6H), 3.55 (m, 1H), 4.74 (dd, 1H), 6.57 (d, 1H), 6.65 (t, 1H), 7.26 (t, 1H), 7.40 (dd, 2H), 7.56 (dd, 2H), 7.71 (dd, 1H), 8.29 (d, 1H). (+Rotamer)

Example 43
1-({2-[5-Phenyl-pyridin-2-ylamino]-ethylamino}-acetyl)-pyrrolidine

This compound was prepared in analogy to example 36, steps A] to C] starting from 2,5-dibromopyridine, 1,2-diaminoethane, phenylboronic acid and IIC. It was isolated as a light yellow powder.
MS(ISP): 325.4 (MH⁺).
¹H-NMR (DMSO-d₆): 1.77 (m, 2H), 1.86 (m, 2H), 2.77 (t, 2H), 3.28–3.39 (m, 8H), 3.5 (broad s, 1H), 6.57 (d, 1H), 6.68 (t, 1H), 7.26 (t, 1H), 7.40 (dd, 2H), 7.56 (dd, 2H), 7.70 (dd, 1H), 8.29 (d, 1H). (+Rotamer)

Example 44
(2S)-1-({2-[6-Phenyl-pyridin-2-ylamino]-ethylamino}-acetyl)-pyrrolidine-2-carbonitrile, Hydrochloride Salt This compound was prepared in analogy to example 36, steps A] to C] starting from 2,6-dibromopyridine, 1,2-diaminoethane, phenylboronic acid and IIA. It was isolated as its free amine, as a white powder.
MS(ISP): 423.3 (MH⁺).
¹H-NMR (DMSO-d₆): 1.90–2.08 (m, 2H), 2.19 (m, 2H), 3.22 (m, 2H), 3.41 (m, 1H), 3.60 (m, 1H), 3.78 (broad s, 2H), 4.13 (m, 2H), 4.84 (dd, 1H), 6.15 (very broad s, 1H), 6.73 (broad s, 1H), 7.23 (d, 1H), 7.50 (m, 3H), 7.78 (broad s, 1H), 8.03 (d, 2H), 9.30 (broad s, 2H). (+Rotamer)

Example 45
(2S)-1-({2-[5-(5-Methyl-[1,3,4]oxadiazol-2-yl)-pyridin-2-ylamino]-ethylamino}-acetyl)-pyrrolidine-2-carbonitrile This compound was prepared in analogy to example 36, steps A] and C] starting from 2-chloro-5-(5-methyl-[1,3,4]oxadiazol-2-yl)-pyridine [CAS 70291-28-0], 1,2-diaminoethane and IIB. It was isolated as its free amine, as a colorless gum.
MS (ISP): 378.3 (MNa⁺), 356.3 (MH⁺).
¹H-NMR (CDCl₃): 2.08–2.22 (m, 5H), 2.59 (s, 3H), 2.94 (t, 2H), 3.32–3.80 (m, 6H), 4.79 (dd, 1H), 5.63 (t, 1H), 6.50 (d, 1H), 8.00 (dd, 1H), 8.68 (d, 1H). (+Rotamer)

Example 46
(2S)-1-({2-[3-(5-Methyl-[1,3,4]oxadiazol-2-yl)-pyridin-2-ylamino]-ethylamino}-acetyl)-pyrrolidine-2-carbonitrile This compound was prepared in analogy to example 36, steps A] and C] starting from 2-chloro-3-(5-methyl-[1,3,4]oxadiazol-2-yl)-pyridine [CAS 70318-99-9], 1,2-diaminoethane and IIB. It was isolated as its free amine as a colorless gum.

MS (ISP): 378.3 (MNa⁺), 356.3 (MH⁺).
¹H-NMR (CDCl₃): 1.95–2.35 (m, 5H), 2.61 (s, 3H), 3.00 (m, 2H), 3.48 (m, 2H), 3.62 (m, 2H), 3.75 (m, 2H), 4.76 (d, 1H), 6.63 (d, 1H), 7.94 (d, 1H), 8.06 (t, 1H), 8.26 (d, 1H). (+Rotamer)

Example 47
(2S)-1-{[2-(4,5-Dimethyl-thiazol-2-ylamino)-ethylamino]-acetyl}-pyrrolidine-2-carbonitrile

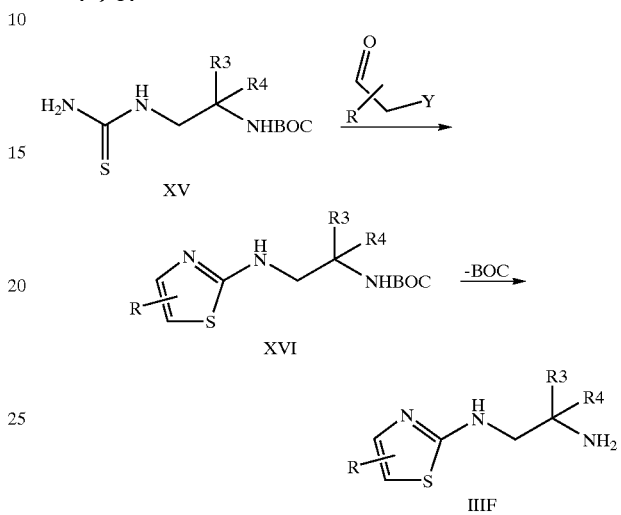

Synthesis of this compound requires the preparation of the corresponding amine precursor IIIF. A possible way for the preparation of IIIF is described in the general scheme above. According to this scheme an optionally protected (2-amino-ethyl)-thiourea XV is converted in the presence of an α-halo-carbonyl compound to the corresponding N1-thiazol-2-yl-ethane-1,2-diamine XVI. Finally, deprotection leads to IIIF. The starting thiourea XV is known [R₃=R₄=H: CAS 331779-96-5] or can be derived in analogy from the corresponding diamine and benzoyl isothiocyanate.

Step A]: [2-(4,5-Dimethyl-thiazol-2-ylamino)-ethyl]-carbamic Acid Tert-butyl Ester A solution of (2-thioureido-ethyl)-carbamic acid tert-butyl ester [CAS 331779-96-5] (3.6 g), 3-bromo-2-butanone (2.45 g), and DIPEA (5.5 ml) in ethanol (100 ml) was stirred overnight at RT and refluxed 1 hour. The mixture was concentrated. Ethyl acetate was added. Insoluble parts were filtered off and the remaining solution was extracted with brine. The organic layer was dried, evaporated and purified by flash chromatography yielding after crystallization 0.86 g of white crystals.
MS(ISP): 272.2 (MH⁺).
¹H-NMR (DMSO-d₆): 1.37 (s, 9H), 1.98 (s, 3H), 2.09 (s, 3H), 3.08 (dt, 2H), 3.16 (dt, 2H), 6.85 (broad t, 1H), 7.13 (broad t, 1H).

Step B]: N1-(4,5-Dimethyl-thiazol-2-yl)-ethane-1,2-diamine

A solution of [2-(4,5-dimethyl-thiazol-2-ylamino)-ethyl]-carbamic acid tert-butyl ester (2.71 g) in methylene chloride (50 ml) was treated with TFA (5 ml) overnight at RT and 1 hour at 60° C. The solvent was evaporated. Ethyl acetate and 1N HCl were added. The separated aqueous layer was extracted under basic conditions with ethyl acetate. The obtained organic layer was washed with brine, dried (MgSO₄) and evaporated yielding 0.42 g of a light yellow oil.

MS(ISP): 172.2 (MH$^+$).
$^1$H-NMR (CDCl$_3$): 2.11 (s, 3H), 2.18 (s, 3H), 2.93 (t, 2H), 3.28 (t, 2H).
Step C]: (2S)-1-{[2-(4,5-Dimethyl-thiazol-2-ylamino)-ethylamino]-acetyl}-pyrrolidine-2-carbonitrile The title compound was obtained from N1-(4,5-dimethyl-thiazol-2-yl)-ethane-1,2-diamine (0.40 g) and IIA (0.13 g) following the procedure outlined in example 1 yielding 57 mg of a light yellow oil.
MS(ISP): 308.2 (MH$^+$).
$^1$H-NMR (CDCl$_3$): 2.05–2.40 (m, 5H), 2.11 (s, 3H), 2.14 (s, 3H), 2.91 (m, 2H), 3.34 (m, 2H), 3.40 (s, 2H), 3.55 (m, 2H), 4.77 (dd, 1H), 5.36 (broad t, 1H). (+Rotamer)

Example 48
(2S)-1-({2-[4-(4-Cyano-phenyl)-thiazol-2-ylamino]-ethylamino}-acetyl)-pyrrolidine-2-carbonitrile, Hydrochloride Salt This compound was prepared in analogy to example 47, steps A] to C] starting from (2-thioureido-ethyl)-carbamic acid tert-butyl ester [CAS 331779-96-5], 4-cyanophenacyl bromide [CAS 20099-89-2] and IIA. The residue obtained by flash chromatography was dissolved in dioxane and precipitated by treatment with HCl in dioxane yielding a with powder.
MS(ISP): 381.3 (MH$^+$).
$^1$H-NMR (DMSO-d$_6$): 2.04 (m, 2H), 2.17 (m, 2H), 3.25 (t, 2H), 3.42 (m, 1H), 3.61 (m, 1H), 3.70 (t, 2H), 4.08 (m, 2H), 4.84 (dd, 1H), 7.15 (broad s, 1H), 7.46 (s, 1H), 7.84 (d, 2H), 8.06 (d, 2H), 8.10 (broad s, 1H), 9.29 (broad t, 2H). (+Rotamer)

Example 49
1-({2-[4-(4-Cyano-phenyl)-thiazol-2-ylamino]-ethylamino}-acetyl)-pyrrolidine This compound was prepared in analogy to example 47, steps A] to C] starting from (2-thioureido-ethyl)-carbamic acid tert-butyl ester [CAS 331779-96-5], 4-cyanophenacyl bromide [CAS 20099-89-2] and IIC. It was isolated as its free amine, as a light yellow oil.
MS(ISP): 356.3 (MH$^+$).

Example 50
(2S)-1-({2-[4-(4-Methoxy-phenyl)-thiazol-2-ylamino]-ethylamino}-acetyl)-pyrrolidine-2-carbonitrile This compound was prepared in analogy to example 47, steps A] to C] starting from (2-thioureido-ethyl)-carbamic acid tert-butyl ester [CAS 331779-96-5], 4-methoxyphenacyl bromide [2632-13-5] and IIA. It was isolated as its free amine, as a light yellow glass.
MS (ISP): 386.3 (MH$^+$).
$^1$H-NMR (CDCl$_3$): 2.05–2.40 (m, 5H), 2.97 (m, 2H), 3.32–3.80 (m, 6H), 3.83 (s, 3H), 4.78 (dd, 1H), 5.74 (broad t, 1H), 6.55 (s, 1H), 6.91 (m, 2H), 7.73 (m, 2H). (+Rotamer)

Example 51
(2S)-1-({2-[4-(3-Phenyl-isoxazol-5-yl)-thiazol-2-ylamino]-ethylamino}-acetyl)-pyrrolidine-2-carbonitrile This compound was prepared in analogy to example 47, steps A] to C] starting from (2-thioureido-ethyl)-carbamic acid tert-butyl ester [CAS 331779-96-5], 2-bromo-1-(3-phenylisoxazol-5-yl)ethan-1-one [CAS 14731-14-7] and IIA. It was isolated as its free amine, as a light brown oil.
MS (ISP): 423.3 (MH$^+$).
$^1$H-NMR (CDCl$_3$): 2.08–2.35 (m, 5H), 2.94 (m, 1H), 3.32–3.80 (m, 7H), 4.78 (dd, 1H), 6.04 (broad t, 1H), 6.85 (s, 1H), 7.08 (s, 1H), 7.46 (m, 3H), 7.85 (m, 2H). (+Rotamer)

Example 52
(2S)-1-{[2-(5-Methyl-2-phenyl-thiazol-4-yl)-ethylamino]-acetyl}-pyrrolidine-2-carbonitrile This compound was prepared in analogy to example 31 (steps A] and C] as outlined for example 31 and step B] according to example 33) starting from 2-(5-methyl-2-phenyl-thiazol-4-yl)-ethanol [CAS 175136-30-8, commercially available]. The compound was obtained as a light yellow oil.
MS (ISP): 355.2 (MH$^+$).

Example 53
(2S)-1-({2-[2-(3-Methyl-phenyl)-5-methyl-oxazol-4-yl]-ethylamino}-acetyl)-pyrrolidine-2-carbonitrile The title compound was prepared in analogy to example 31 starting from 2-[2-(3-methyl-phenyl)-5-methyl-oxazol-4-yl]-ethanol. The starting material could be prepared from 3-methyl-benzamide [CAS 618-47-3, commercially available] and methyl-4-bromo-3-oxopentanoate with 4-fluoro-benzamide as described in Collins, J. L. et al. *J. Med. Chem.* 1998, 41, 5037–5054. Steps A] to C] yielded a brown oil.
MS (ISP): 353.2 (MH$^+$).

Example 54
(2S)-1-({2-[2-(3,5-Dimethoxy-phenyl)-5-methyl-oxazol-4-yl]-ethylamino}-acetyl)-pyrrolidine-2-carbonitrile The title compound was prepared in analogy to example 31 starting from 2-[2-(3,5-dimethoxy-phenyl)-5-methyl-oxazol-4-yl]-ethanol. The starting material could be prepared from 3,5-dimethoxy-benzamide FCAS 17213-58-0, commercially available] and methyl-4-bromo-3-oxopentanoate with 4-fluoro-benzamide as described in Collins, J. L. et al. *J. Med. Chem.* 1998, 41, 5037–5054. Steps A] to C] yielded a brown gum.
MS (ISP): 399.5 (MH$^+$).

Example 55
(2S)-1-({2-[2-(4-Fluoro-3-methyl-phenyl)-5-methyl-oxazol-4-yl]-ethylamino}-acetyl)-pyrrolidine-2-carbonitrile The title compound was prepared in analogy to example 31 starting from 2-[2-(3-methyl-phenyl)-5-methyl-oxazol-4-yl]-ethanol. The starting material could be prepared from 4-fluoro-3-methyl-benzamide [CAS 261945-92-0, commercially available] and methyl-4-bromo-3-oxopentanoate with 4-fluoro-benzamide as described in Collins, J. L. et al. *J. Med. Chem.* 1998, 41, 5037–5054. Steps A] to C] yielded a yellow oil.
MS (ISP): 371.3 (MH$^+$).

Example 56
(2S)-1-({2-[2-(3-Methyl-phenyl)-5-methyl-thiazol-4-yl]-ethylamino}-acetyl)-pyrrolidine-2-carbonitrile The title compound was prepared in analogy to example 31 (steps A] and C] as outlined for example 31 and step B] according to example 33) starting from 2-[2-(3-methyl-phenyl)-5-methyl-thiazol-4-yl]-ethanol. This starting material could be prepared from 3-methyl-benzthioamide [CAS 2362-63-2, commercially available] and methyl-4-bromo-3-oxopentanoate with 4-fluoro-benzamide as described in Collins, J. L. et al *J. Med. Chem.* 1998, 41, 5037–5054. The compound was obtained as a yellow oil.
MS (ISP): 369.2 (MH$^+$).

Example 57
(2S)-1-({2-[2-(2-Ethyl-pyridin-4-yl)-5-methyl-thiazol-4-yl]-ethylamino}-acetyl)-pyrrolidine-2-carbonitrile The title compound was prepared in analogy to example 31 (steps A] and C] as outlined for example 31 and step B]

according to example 33) starting from 2-[2-(2-ethyl-pyridin-4-yl)-5-methyl-thiazol-4-yl]-ethanol. This starting material could be prepared from 2-ethyl-4-pyridinecarbothioamide [CAS 536-33-4, commercially available] and methyl-4-bromo-3-oxopentanoate with 4-fluoro-benzamide as described in Collins, J. L. et al. *J. Med. Chem.* 1998, 41, 5037–5054. The compound was obtained as a yellow gum.

MS (ISP): 384.2 (MH⁺).

Example 58

(2S)-1-({2-[5-Methyl-2-(5-trifluoromethyl-pyridin-2-yl)-thiazol-4-yl]-ethylamino}-acetyl)-pyrrolidine-2-carbonitrile The title compound was prepared in analogy to example 31 (steps A] and C] as outlined for example 31 and step B] according to example 33) starting from 2-[5-methyl-2-(5-trifluoromethyl-pyridin-2-yl)-thiazol-4-yl]-ethanol. This starting material could be prepared from 5-trifluoromethyl-2-pyridinecarbothioamide [CAS 175277-51-7, commercially available] and methyl-4-bromo-3-oxopentanoate with 4-fluoro-benzamide as described in Collins, J. L. et al. *J. Med. Chem.* 1998, 41, 5037–5054. The compound was obtained as a yellow gum.

MS (ISP): 424.3 (MH⁺).

Example 59

(2S)-1-({2-[5-Methyl-2-(6-methyl-pyridin-3-yl)-thiazol-4-yl]-ethylamino]-acetyl)-pyrrolidine-2-carbonitrile The title compound was prepared in analogy to example 31 (steps A] and C] as outlined for example 31 and step B] according to example 33) starting from 2-[5-methyl-2-(5-trifluoromethyl-pyridin-2-yl)-thiazol-4-yl]-ethanol. This starting material could be prepared from 2-methyl-5-pyridinecarbothioamide [CAS 175277-57-3, commercially available] and methyl-4-bromo-3-oxopentanoate with 4-fluoro-benzamide as described in Collins, J. L. et al. *J. Med. Chem.* 1998, 41, 5037–5054. The compound was obtained as a yellow gum.

MS (ISP): 370.3 (MH⁺).

Example 60

(2S)-1-{[1,1-Dimethyl-2-(5-methyl-2-phenyl-oxazol-4-yl)-ethylamino]-acetyl}-pyrrolidine-2-carbonitrile

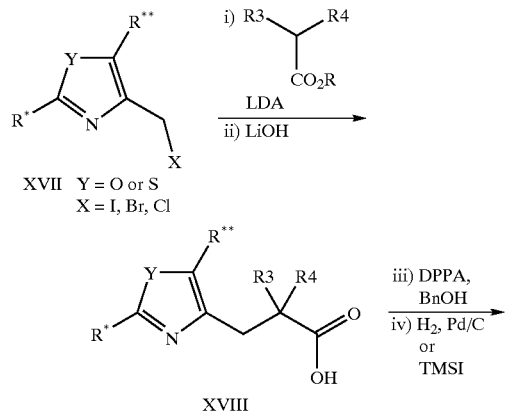

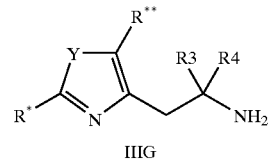

For the synthesis of this compound the preparation of the corresponding amine precursor IIIG is required. A possible synthetic sequence is described in the general scheme above which started with the appropriate substituted halomethyl oxazole or thiazole derivative XVII. Ester alkylation i) and subsequent saponification ii) yielded the acid intermediate XVIII. This was subjected to a Curtius rearrangement iii) which could be conducted by diphenylphosphoryl azide. A final deprotection step iv) resulted in the formation of the amine IIIG as the free base or its salt. The starting materials XVII are known or were prepared in analogy to the procedures described in WO 01/19805 A1, U.S. Pat. No. 545531, *Chem. Pharm. Bull.* 1971, 19, 2050–2057 and *J. Med. Chem.* 1972, 15,419–420.

Step A]: 2,2-Dimethyl-3-(5-methyl-2-phenyl-oxazol-4-yl)-propionic Acid n-Buthyllithium (1.6M in hexane, 5.05 ml) was added dropwise to a solution of diisopropylamine (1.16 ml) in THF (30 ml) at 0° C. under argon. The resulting mixture was stirred for another 15 minutes before it was cooled to −78° C. and a solution of methyl isobutyrate (0.84 ml) in THF (3 ml) was added dropwise. After the addition was completed, the reaction mixture was allowed to warm to 0° C. and than again cooled to −78° C. At this temperature a solution of 4-chloromethyl-5-methyl-2-phenyl-oxazole [CAS 103788-61-0, commercially available] (1.17 g) in THF (6 ml) and DMPU (7.7 ml) was added. Stirring was continued for another 30 minutes before a saturated NH₄Cl solution (1 ml) was added. Then the THF was removed in vacuo and water was added to the remaining residue. This mixture was extracted with ether and the combined organic extracts were washed with water and brine and dried (MgSO₄). After evaporation of the solvent the crude alkylation product (1.46 g) was dissolved in THF (20 ml) and LiOH solution (1M, 14.5 ml) was added. The reaction mixture was stirred overnight, concentrated and washed with ether. Then the pH was adjusted to 1 by addition of 3N HCl and the resulting suspension was extracted with ether. Finally the combined extracts were washed with water and brine, dried (MgSO₄) and the solvent was removed in vacuo. The product was obtained as a white solid (1.33 g).

MS (ISP): 260.2 (MH⁺).

Step B]: 1,1-Dimethyl-2-(5-methyl-2-phenyl-oxazol-4-yl)-ethylamine

The acid derivative prepared according to step A] (1.32 g) was suspended in toluene and triethylamine (0.71 ml) was added. After 15 min diphenylphosphoryl azide (1.1 ml) was added and the reaction mixture was refluxed for 2 hours. Then benzyl alcohol (0.79 ml) was added and heating was continued overnight. The mixture was then allowed to cool to RT, diluted with ether and washed with citric acid solution (0.5M), saturated KHCO₃ solution and brine and was dried (MgSO₄). After evaporation of the solvent, the residue was purified by chromatography (hexane/ethyl acetate 7:1). The pure rearrangement product was than dissolved in ethanol (37 ml), palladium on carbon (10%, 20 mg) was added and the reaction vessel was charged with hydrogen. After 24 hours the catalyst was filtered off and the solvent was removed in vacuo. The product was obtained as light yellow liquid (0.74 g).

MS (ISP): 231.2 (MH⁺).

Step C]: (2S)-1-{[1,1-Dimethyl-2-(5-methyl-2-phenyl-oxazol-4-yl)-ethylamino]-acetyl}-pyrrolidine-2-carbonitrile The title compound was obtained from the amine derivative prepared according to step B] (0.74 g) and IIA (0.18 g) following the procedure outlined in example 1. Final chromatography (CH$_2$Cl$_2$/MeOH 9:1) gave a light yellow gum (0.36 g).

MS (ISP): 367.3 (MH$^+$).

Example 61

(2S)-1-({1,1-Dimethyl-2-[2-(3-methyl-phenyl)-5-methyl-oxazol-4-yl]-ethylamino}-acetyl)-pyrrolidine-2-carbonitrile The title compound was prepared in analogy to example 60, steps A] to C] starting from 4-chloromethyl-5-methyl-2-(3-methyl-phenyl)-oxazole and methyl isobutyrate. The starting material could be prepared from 3-methylbenzaldehyde and 2,3-butanedione oxime as described for benzaldehyde in Chem. Pharm. Bull. 1971, 19, 2050–2057. It was obtained as a yellow gum.

MS (ISP): 381.3 (MH$^+$).

Example 62

(2S)-1-{[1-(5-Methyl-2-phenyl-oxazol-4-ylmethyl)-cyclopentylamino]-acetyl}-pyrrolidine-2-carbonitrile The title compound was prepared in analogy to example 60, steps A] to C] starting from 4-chloromethyl-5-methyl-2-phenyl-oxazole [CAS 103788-61-0, commercially available] and methyl cyclopentanecarboxylate. It was obtained as a colorless gum.

MS (ISP): 393.2 (MH$^+$).

Example 63

(2S)-1-{[1-(5-Methyl-2-phenyl-oxazol-4-ylmethyl)-cyclobutylamino]-acetyl}-pyrrolidine-2-carbonitrile The title compound was prepared in analogy to example 60, steps A] to C] starting from 4-chloromethyl-5-methyl-2-phenyl-oxazole [CAS 103788-61-0, commercially available] and ethyl cyclobutanecarboxylate. It was obtained as a yellow oil.

MS (ISP): 379.3 (MH$^+$).

Example 64

(2S)-1-[-(5-Methyl-2-phenyl-oxazol-4-ylmethyl)-cyclopropylamino]-acetyl}-pyrrolidine-2-carbonitrile The title compound was prepared in analogy to example 60, steps A] to C] starting from 4-chloromethyl-5-methyl-2-phenyl-oxazole [CAS 103788-61-0, commercially available] and tert.butyl cyclopropanecarboxylate. It was obtained as a yellow gum.

MS (ISP): 365.2 (MH$^+$).

Example 65

(2S)-1-{[1,1-Dimethyl-2-(5-methyl-2-phenyl-thiazol-4-yl)-ethylamino]-acetyl}-pyrrolidine-2-carbonitrile The title compound was prepared in analogy to example 60, steps A] to C] starting from 4-bromomethyl-5-methyl-2-phenyl-thiazole [CAS 329977-09-5] and methyl isobutyrate. It was obtained as a yellow solid.

MS (ISP): 384.3 (MH$^+$).

Example 66

(2S)-1-{[1-(5-Methyl-2-phenyl-thiazol-4-ylmethyl)-cyclopentylamino]-acetyl}-pyrrolidine-2-carbonitrile The title compound was prepared in analogy to example 60, steps A] to C] starting from 4-bromomethyl-5-methyl-2-phenyl-thiazole [CAS 329977-09-5] and methyl cyclopentanecarboxylate. It was obtained as a light yellow oil.

MS (ISP): 409.2 (MH$^+$).

Example 67

(2S)-1-{[1-(5-Methyl-2-phenyl-thiazol-4-ylmethyl)-cyclobutylamino]-acetyl}-pyrrolidine-2-carbonitrile The title compound was prepared in analogy to example 60, steps A] to C] starting from 4-bromomethyl-5-methyl-2-phenyl-thiazole [CAS 329977-09-5] and ethyl cyclobutanecarboxylate. It was obtained as a light yellow gum.

MS (ISP): 395.3 (MH$^+$).

Example 68

(2S)-1-({2-[2-(4-Fluoro-3-methyl-phenyl)-5-methyl-oxazol-4-yl]-1,1-dimethyl-ethylamino-acetyl)-pyrrolidine-2-carbonitrile The title compound was prepared in analogy to example 60, steps A] to C] starting from 4-chloromethyl-5-methyl-2-(4-fluoro-3-methyl-phenyl)-oxazole and methyl isobutyrate. The starting material could be prepared from 4-fluoro-3-methylbenzaldehyde and 2,3-butanedione oxime as described for benzaldehyde in Chem. Pharm. Bull. 1971, 19, 2050–2057. It was obtained as a yellow solid.

MS (ISP): 399.4 (MH$^+$).

Example 69

(2S)-1-({2-[2-(3-Chloro-phenyl)-5-methyl-oxazol-4-yl]-1,1-dimethyl-ethylamino}-acetyl)-pyrrolidine-2-carbonitrile The title compound was prepared in analogy to example 60 starting from 4-chloromethyl-5-methyl-2-(3-chloro-phenyl)-oxazole and methyl isobutyrate. The starting material could be prepared from 3-methylbenzaldehyde and 2,3-butanedione oxime as described for benzaldehyde in Chem. Pharm. Bull. 1971, 19,2050–2057. Steps A] and C] were performed as outlined in example 60 but the amine deprotection step B] was done alternatively:

{2-[2-(3-Chloro-phenyl)-5-methyl-oxazol-4-yl]-1,1-dimethyl-ethyl}-carbamic acid (0.95 g) and sodiumiodide (0.85 g) were dissolved in acetonitrile (10 ml) and trimethylchlorosilane was added slowly. The reaction mixture was stirred overnight, concentrated in vacuo and the remaining residue was purified by chromatography (CH$_2$Cl$_2$/MeOH 9:1 to 4:1). The title compound (275 mg) was obtained as a dark brown solid as its hydroiodide salt.

MS (ISP): 265.2 (MH$^+$) and 267.3 (MH$^+$).

After step C] the title compound was obtained as an off white foam.

MS (ISP): 401.3 (MH$^+$) and 403.3 (MH$^+$).

Example 70

(2S)-1-({2-[2-(2-Chloro-phenyl)-5-methyl-oxazol-4-yl]-1,1-dimethyl-ethylamino}-acetyl-2-carbonitrile The title compound was prepared in analogy to example 60 starting from 4-chloromethyl-5-methyl-2-(2-chloro-phenyl)-oxazole and methyl isobutyrate. The starting material could be prepared from 3-methylbenzaldehyde and 2,3-butanedione oxime as described for benzaldehyde in Chem. Pharm. Bull. 1971, 19, 2050–2057. Steps A] and C] were performed as outlined in example 60, step B] was done according to example 69. The compound was obtained as a light brown foam.

MS (ISP): 401.4 (MH$^+$) and 403.3 (MH$^+$).

Example 71

(2S)-1-{1-[2-(4-Fluoro-3-methyl-phenyl)-5-methyl-oxazol-4-ylmethyl]-cyclopropylamino}-acetyl)-pyrrolidine-2-carbonitrile The title compound was prepared in analogy to example 60, steps A] to C] starting from 4-chloromethyl-5-methyl- 2-(4-fluoro-3-methyl-phenyl)-oxazole and tert.butyl cyclopropanecarboxylate. The starting material could be prepared from 4-fluoro-3-methylbenzaldehyde and 2,3-butanedione oxime as described for benzaldehyde in *Chem. Pharm. Bull.* 1971, 19, 2050–2057. The title compound was obtained as a white gum.

MS (ISP): 397.3 (MH$^+$).

Example 72

(2S)-1-({1-[2-(3-Chloro-phenyl)-5-methyl-oxazol-4-ylmethyl]-cyclopropylamino}-acetyl)-pirrolidine-2-carbonitrile The title compound was prepared in analogy to example 60 starting from 4-chloromethyl-5-methyl-2-(3-chlorophenyl)-oxazole and tert.butyl cyclopropanecarboxylate. The starting material could be prepared from 3-methylbenzaldehyde and 2,3-butanedione oxime as described for benzaldehyde in *Chem. Pharm. Bull.* 1971, 19, 2050–2057. Steps A] and C] were performed as outlined in example 60, step B] was done according to example 69. The title compound was obtained as a brown gum.

MS (ISP): 399.3 (MH$^+$) and 401.3 (MH$^+$).

Example 73

(2S)-1-({1-[2-(2-Chloro-phenyl)-5-methyl-oxazol-4-ylmethyl]-cyclopropylamino}-acetyl)-pyrrolidine-2-carbonitrile The title compound was prepared in analogy to example 60 starting from 4-chloromethyl-5-methyl-2-(2-chlorophenyl)-oxazole and tert.butyl cyclopropanecarboxylate. The starting material could be prepared from 3-methylbenzaldehyde and 2,3-butanedione oxime as described for benzaldehyde in *Chem. Pharm. Bull.* 1971, 19, 2050–2057. Steps A] and C] were performed as outlined in example 60, step B] was done according to example 69. The title compound was obtained as a light brown gum.

MS (ISP): 399.3 (MH$^+$) and 401.4 (MH$^+$).

Example 74

(2S)-1-{[1,1-Dimethyl-2-(2-phenyl-oxazol-4-yl)-ethylamino]-acetyl}-pyrrolidine-2-carbonitrile The title compound was prepared in analogy to example 60, steps A] to C] starting from 4-chloromethyl-2-phenyl-oxazole [CAS 30494-97-4] and methyl isobutyrate. It was obtained as a light yellow oil.

MS (ISP): 353.2 (MH$^+$).

Example 75

(2S)-1-{[1,1-Dimethyl-2-(2-phenyl-thiazol-4-yl)-ethylamino]-acetyl}-pyrrolidine-2-carbonitrile The title compound was prepared in analogy to example 60, steps A] to C] starting from 4-chloromethyl-2-phenyl-thiazole [CAS 4771-13-7, commercially available] and methyl isobutyrate. It was obtained as a light yellow oil.

MS (ISP): 369.2 (MH$^+$).

Example 76

(2S)-1-{[1,1-Dimethyl-2-(2-morpholin-4-yl-thiazol-4-yl)-ethylamino]-acetyl}-pyrrolidine-2-carbonitrile The title compound was prepared in analogy to example 60 starting from 4-(chloromethyl)-2-(4-morpholinyl)-thiazole [CAS 172649-58-0] and methyl isobutyrate. Steps A] and C] were performed as outlined in example 60, step B] was done according to example 69. The compound was obtained as a light yellow gum.

MS (ISP): 378.3 (MH$^+$).

Example 77

(2S)-1-{[1,1-Dimethyl-2-(2-piperidin-1-yl-thiazol-4-yl)-ethylamino]-acetyl}-pyrrolidine-2-carbonitrile The title compound was prepared in analogy to example 60 starting from 4-(chloromethyl)-2-(1-piperidinyl)-thiazole and methyl isobutyrate. The starting material could be prepared as described for 4-(chloromethyl)-2-(4-morpholinyl)-thiazole in U.S. Pat. No. 545,531. Steps A] and C] were performed as outlined in example 60, step B] was done according to example 69. The compound was obtained as a brown gum.

MS (ISP): 376.3 (MH$^+$).

Example 78

(2S)-1-{[1,1-Dimethyl-3-(5-methyl-3-phenyl-pyrazol-1-yl)-propylamino]-acetyl}-pyrrolidine-2-carbonitrile, methanesulfonic acid salt Synthesis of this type of compound required the preparation of the hitherto unknown 6-membered sulfimidate reagents XIX for the preparation of amine precursors III-H–IIIL. In general, a BOC protected 3-aminopropan-1-ol XX (e.g. made by reduction from azetidinone XXI) is cyclized with SOCl$_2$ in the presence of imidazole. The intermediate is usually not isolated but subsequently oxidized to the BOC protected sulfonic acid derivative XIX. As the 5 membered sulfimidates IV, these compounds are versatile alkylating agents that react readily with a variety of nitrogen and carbon based nucleophiles.

Pyrazole derivatives XXII used for examples 78–97 are commercially available or can be accessed via pathways A or B known in the literature involving 1,3-diketones XXIII and XXIV as synthetic intermediates. If pyrazoles XXII are treated with strong bases such as potassium-tert-butoxide (KO$^{tert}$Bu) or the like followed by a sulfimidate XIX, N-alkylated products XXV-A and XXV-B (mixture of regioisomers) are obtained. Usually, regioisomer XXV-A can be isolated in larger amounts. Treatment of these BOC protected amines with acids such as TFA or the like results in liberation of the free amines IIIH-A and IIIH-B that are used in the coupling reaction with IIA to furnish cyanopyrrolidines I.

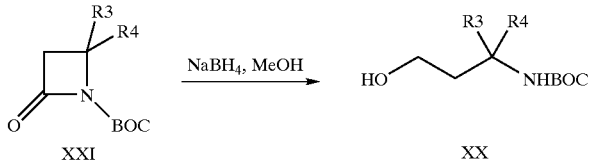

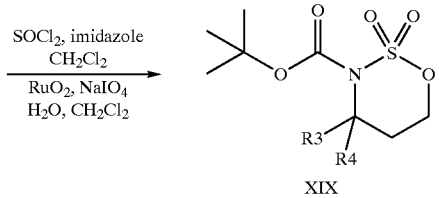

Pathway A:

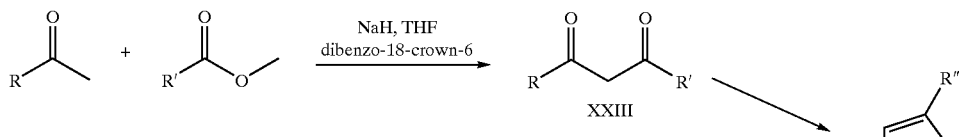

Pathway B:

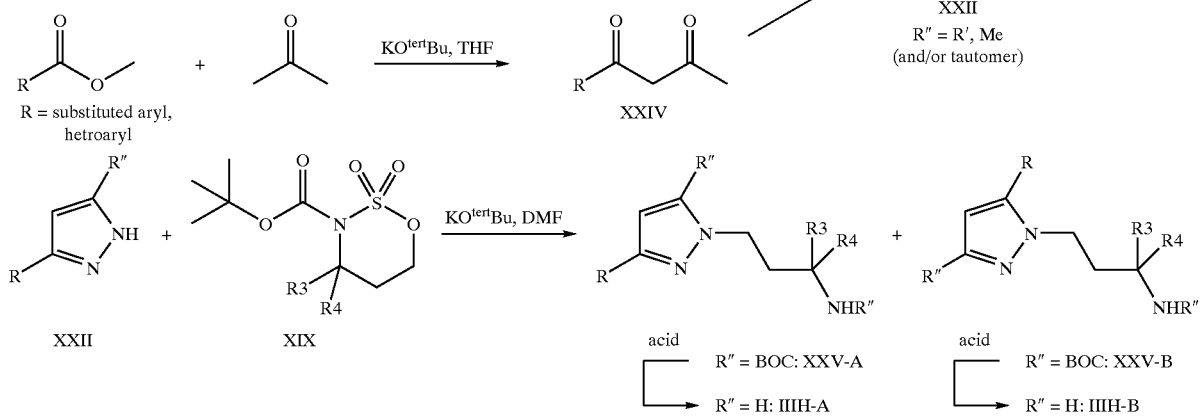

Step A]: (3-Hydroxy-1,1-dimethyl-propyl)-carbamic acid tert-butyl ester 4,4-Dimethyl-1-tert-butyloxycarbonyl-azetidine-2-one (32.5 g, synthesized according to Schoen et al., *J. Med. Chem.* 1994, 37 (7), 897) was dissolved in methanol (450 ml). The solution was cooled to 0° by means of an ice bath and treated with sodium borohydride (18.3 g, 6 portions over 45 minutes). The mixture was allowed to stir for 3 hours at 0°, warmed to room temperature and stirred for another 60 min. The reaction mixture was then poured into a mixture of ice, water and sat. $NH_4Cl$ solution and extracted with ether. The organic layer was separated, washed with brine, dried over $Na_2SO_4$ and evaporated. The residual oil was purified by flash chromatography (gradient of hexanes in ethyl acetate: 7/3 to 1/1). The fractions containing the product were combined, evaporated and dried in vacuo to leave a colorless oil (26.7 g).

$^1$H-NMR ($CDCl_3$): 1.32 (s, 3H), 1.43 (s, 9H), 1.88 (t, J=6.3Hz, 2H), 3.77 (t, J=6.2 Hz, 2H), 4.86 (broad s, 1H).

Step B]: 4,4-Dimethyl-2,2-dioxo-2λ'-[1,2,3]oxathiazinane-3-carboxylic acid tert-butyl ester Imidazole (53.6 g) was dissolved in $CH_2Cl_2$ and cooled to 0° by means of an ice bath. Thionylchloride (28.1 g) dissolved in 100 ml abs. $CH_2Cl_2$ was added drop by drop and the resulting mixture was allowed to warm to RT. Stirring was continued for 60 min at RT and then the mixture was cooled to −78° C. A solution of (3-hydroxy-1,1-dimethyl-propyl)-carbamic acid tert-butyl ester (26.7 g) in 150 ml $CH_2Cl_2$ was added over a period of 50 min and the resulting mixture was allowed to warm to RT and stirred for 24 hours. TLC analysis confirmed the complete consumption of the starting material. The mixture was filtered through dicalite and the filter aid was washed well with $CH_2Cl_2$. The organic layer was diluted with $CH_2Cl_2$, washed with water and brine, dried over $Na_2SO_4$, filtered and concentrated to a volume of approx. 750 ml.

A solution of $NaIO_4$ (61.2 g) in 620 ml water was added and the mixture was cooled to 0° C. Ru(IV)$O_2$ hydrate (1.23 g) was added and the black suspension was stirred for 90 min at 0° C. It was then warmed to RT and allowed to stir for another 20 hours. The mixture was filtered through dicalite and the filtrate was extracted with $CH_2Cl_2$. The combined organic layers were washed with brine, dried and filtered. Treatment of the filtrate with activated charcoal (6.9 g) for 30 min removed all traces of Ru. The mixture was filtered again and evaporated to give an oil that was purified by flash chromatography (hexanes/ethyl acetate 9:1 and then 8:2) to give the desired product as a colorless solid (yield: 17.3 g).

$^1$H-NMR ($CDCl_3$): 1.53 (s, 9H), 1.63 (s, 6H), 2.29 (t, J=6.8Hz, 2H), 4.62 (t, J=6.8Hz, 2H)

Step C]: [1,1-Dimethyl-3-(5-methyl-3-phenyl-pyrazol-1-yl)-propyl]-carbamic acid tert-butyl Ester 5-Methyl-3-phenyl-1H-pyrazole (320 mg, prepared from benzoylacetone and hydrazine according to Ali et al., *Pak. J. Sci. Ind. Res.* 1993, 36 (12), 502) was dissolved in DMF (7 ml) and cooled to 0° C. with an ice bath. Potassium-tert-butoxide (284 mg) was added in portions and the mixture was stirred for 45 min at 0° C. Then, 4,4-dimethyl-2,2-dioxo-2λ'-[1,2,3]oxathiazinane-3-carboxylic acid tert-butyl ester (617 mg) was added in one portion and the reaction mixture was allowed to stir for 20 hours at RT. HCl (1N aqueous solution, 10 ml) was added and stirring was continued for 15 minutes. The mixture was diluted with ether, washed with water and brine (the aqueous layers were re-extracted twice with ether), dried and evaporated. The crude product was purified by flash chromatography (0 to 15% gradient of $CH_3CN$ in $CH_2Cl_2$) to give the desired product as a yellow gum. Yield: 545 mg. A regioisomer present in minor amounts was removed in the chromatographic purification step.

MS (ISP): 344.5 (MH$^+$)

Step D]: 1,1-Dimethyl-3-(5-methyl-3-phenyl-pyrazol-1-yl)-propylamine

[1,1-Dimethyl-3-(5-methyl-3-phenyl-pyrazol-1-yl)-propyl]-carbamic acid tert-butyl ester (540 mg) was treated with TFA/CH$_2$Cl$_2$ 3:1 (20 ml) at 0° C. for 2 hours. The resulting mixture was concentrated in vacuo and the residue was diluted with ethyl acetate. The organic layer was washed with a mixture of brine/sat. Na$_2$CO$_3$ and brine, dried and evaporated to give a crude oil. This was purified by flash chromatography (5% to 40% gradient of MeOH in CH$_2$Cl$_2$, 0.5% NH$_4$OH content) to give the title compound (349 mg) as a yellow gum.

MS (ISP): 244.5 (MH$^+$)

Step E]: (2S)-1-{[1,1-Dimethyl-3-(5-methyl-3-phenyl-pyrazol-1-yl)-propylamino]-acetyl}-pyrrolidine-2-carbonitrile, methanesulfonic acid salt 1,1-Dimethyl-3-(5-methyl-3-phenyl-pyrazol-1-yl)-propylamine (344 mg) was dissolved in dry DMF (7 ml) under argon and calcium hydroxide (95 mg) was added. A solution of 222 mg (S)-1-(2-chloro-acetyl)-pyrrolidine-2-carbonitrile (IIA) in DMF (7 ml) was added within 5 hours by means of a syringe pump and the resulting cloudy mixture was allowed to stir for 3 days. The mixture was poured into 1 N NaOH and extracted with ether. The organic layer was washed with 1N NaOH and brine, dried and evaporated. The residue was purified by flash chromatography using a gradient of MeOH in CH$_2$Cl$_2$ (0 to 15%) to give the title compound as the free base (281 mg). For salt formation, 92 mg of this material were dissolved in abs. tert-butylmethyl ether (6 ml). To this solution was added methanesulfonic acid (2.42 ml, 0.1 M in tert-butylmethyl ether) drop by drop. The resulting suspension was stirred at RT for 30 min and then filtered. The title compound thus obtained was dried in vacuo. Yield: 101 mg.

MS (ISP): 380.5 (MH$^+$, free base).

Example 79

(2S)-1-{[3-(5-Methyl-3-phenyl-pyrazol-1-yl)-propylamino]-acetyl}-pyrrolidine-2-carbonitrile, methanesulfonic acid salt Step A]: 2,2-Dioxo-2λ'-[1,2,3] oxathiazinane-3-carboxylic acid tert-butyl ester This compound was prepared as described previously for 4,4-Dimethyl-2,2-dioxo-2λ'-[1,2,3]oxathiazinane-3-carboxylic acid tert-butyl ester (example 78, Step B]) from (3-hydroxy-propyl)-carbamic acid tert-butyl ester (10 g). The desired sulfimidate was obtained as a colorless foam (11 g).

$^1$H-NMR (δ, CDCl$_3$): 1.54 (s, 9H), 2.09 (m, 2H), 4.01 (t, J=5.6Hz, 2H), 4.67 (t, J=6.0, 2H).

Steps B] to D]: (2S)-1-{[3-(5-Methyl-3-phenyl-pyrazol-1-yl)-propylamino]-acetyl}-pyrrolidine-2-carbonitrile, methanesulfonic acid salt This compound was obtained in analogy to example 78, steps C] to E] from 5-methyl-3-phenyl-1H-pyrazole, 2,2-Dioxo-2λ'-[1,2,3]oxathiazinane-3-carboxylic acid tert-butyl ester and IIA as a methanesulfonic acid addition salt.

MS (ISP): 352.4 (MH$^+$, free base).

Example 80

(2S)-1-({1,1-Dimethyl-3-[5-methyl-3-(3-trifluoromethyl-phenyl)-pyrazol-1-yl]-propylamino}-acetyl)-pyrrolidine-2-carbonitrile, methanesulfonic acid salt Step A]: 5-Methyl-3-(3-trifluoromethyl-phenyl)-1H-pyrazole Ethyl acetate (2.45 ml) was added to THF (50 ml) and treated with sodium hydride (1.09 g, 60% dispersion in oil) under argon. A catalytic amount of ethanol (2 drops) was added followed by dibenzo-18-crown-6 (90 mg) and 3-trifluoromethylacetophenone (2.35 g) dissolved in THF (20 ml)) added over a period of 20 min. The brown mixture was heated to reflux for 2 hours) cooled and poured into water. The pH was adjusted to 5 to 6 with 2 N HCl and 2 N Na$_2$CO$_3$, respectively. The aqueous phase was extracted with ethyl acetate and the organic layer was washed with brine, dried and evaporated to give the intermediate 1,3-dicarbonyl compound as an orange solid.

This material was dissolved in ethanol/water 1:1 (50 ml) and treated with hydrazine monohydrate (0.8 ml). The mixture was refluxed for 3 hours, cooled and poured into water. The pH was adjusted to 8–9 with Na$_2$CO$_3$ solution (2M) and the aqueous layer was then extracted with ethyl acetate. The organic layers were washed with brine, dried and evaporated to give a crude oil. This was purified by flash chromatography (gradient of hexanes in ethyl acetate) to give the title compound as a light yellow solid (1.4 g).

MS (ISP): 227.2 (MH$^+$).

Steps B] to D]: (2S)-1-({1,1-Dimethyl-3-[5-methyl-3-(3-trifluoromethyl-phenyl)-pyrazol-1-yl]-propylamino}-acetyl)-pyrrolidine-2-carbonitrile, methanesulfonic acid salt This compound was obtained in analogy to example 78, steps C] to E] from 5-methyl-3-(3-trifluoromethyl-phenyl)-1H-pyrazole, 4,4-dimethyl-2,2-dioxo-2λ'-[1,2,3] oxathiazinane-3-carboxylic acid tert-butyl ester and IIA as a methanesulfonic acid addition salt.

MS (ISP): 448.2 (MH$^+$, free base).

Example 81

(2S)-1-({1,1-Dimethyl-3-[5-methyl-3-(3-trifluoromethoxy-phenyl)-pyrazol-1-yl]-propylamino}-acetyl)-pyrrolidine-2-carbonitrile, methanesulfonic acid salt The title compound was obtained in analogy to example 80, steps A] to D] from 3-trifluoromethoxyacetophenone, 4,4-dimethyl-2,2-dioxo-2λ'-[1,2,3]oxathiazinane-3-carboxylic acid tert-butyl ester and IIA as a methanesulfonic acid addition salt.

MS (ISP): 464.4 (MH$^+$, free base).

Example 82

(2S)-1-{[3-(5-Ethyl-3-phenyl-pyrazol-1-yl)-1,1-dimethyl-propylamino]-acetyl}-pyrrolidine-2-carbonitrile, methanesulfonic acid salt This compound was made in analogy to example 80, steps A] to D] from acetophenone, ethyl propionate, 4,4-dimethyl-2,2-dioxo-2λ'-[1,2,3]oxathiazinane-3-carboxylic acid tert-butyl ester and IIA as a methanesulfonic acid addition salt.

MS (ISP): 394.4 (MH$^+$, free base).

Example 83

(2S)-1-{[1,1-Dimethyl-3-(5-methyl-3-pyridin-3-yl-pyrazol-1-yl)-propylamino]-acetyl}-pyrrolidine-2-carbonitrile, methanesulfonic acid salt Step A]: 3-(5-Methyl-1H-pyrazol-3-yl)-pyridine This compound known in the literature was prepared via the 1,3-dicarbonyl intermediate according to modified procedures from Ferenczy et al., Monatsh. Chem. 1897, 18, 674 and Gough et al., J. Chem. Soc. 1933, 350: Methyl nicotinic acid (20 g) was dissolved in THF (250 ml) and acetone (39 ml) was added. Solid potassium-tert-butoxide (18 g) was added in portions over 15 min and the resulting yellow suspension was heated to reflux for 60 min. The mixture was then cooled and the solvent was evaporated in vacuo to leave a brown solid. This was dissolved in water/ethanol 1:1, quenched with acetic acid (13 ml) and treated with hydrazine monohydrate (8.9 ml). The resulting solution was heated to reflux for 60 min, cooled, diluted with water and extracted with ethyl acetate. The organic layer was separated, washed with brine, dried and evaporated to leave an orange oil. This material was treated with ethyl acetate/hexanes 1:1 (250 ml) whereupon crystallization occurred.

The suspension was stirred for 30 min and then filtered to give the desired compound as a colorless solid (13.4 g).

$^1$H-NMR (δ, CDCl$_3$): 2.74 (s, 3H), 6.41 (s, 1H), 7.33 (dd, 1H), 8.06 (m, 1H), 8.55 (dd, 1H), 8.99 (d, 1H).

Steps B] to D]: (2S)-1-{[1,1-Dimethyl-3-(5-methyl-3-pyridin-3-yl-pyrazol-1-yl)-propylamino]-acetyl}-pyrrolidine-2-carbonitrile, methanesulfonic acid salt This compound was obtained in analogy to example 78, steps C] to E] from 3-(5-methyl-1H-pyrazol-3-yl)-pyridine, 4,4-dimethyl-2,2-dioxo-2λ'-[1,2,3]oxathiazinane-3-carboxylic acid tert-butyl ester and IIA as a methanesulfonic acid addition salt.

MS (ISP): 381.4 (MH$^+$, free base).

Example 84

(2S)-1-{[1,1-Dimethyl-3-(3-methyl-5-pyridin-3-yl-pyrazol-1-yl)-propylamino}-acetyl}-pyrrolidine-2-carbonitrile, methanesulfonic acid salt Starting material for this synthesis was [1,1-dimethyl-3-(3-methyl-5-pyridin-3-yl-pyrazol-1-yl)-propyl]-carbamic acid tert-butyl ester, that was obtained as the minor regioisomer in the alkylation of 3-(5-methyl-1H-pyrazol-3-yl)-pyridine with 4,4-dimethyl-2,2-dioxo-2λ'-[1,2,3]oxathiazinane-3-carboxylic acid tert-butyl ester (example 83, step B]. The title compound was then obtained in analogy to example 78, steps D] and E] as a methanesulfonic acid addition salt.

MS (ISP): 381.3 (MH$^+$, free base).

Example 85

(2S)-1-({3-[3-(3-Chloro-phenyl)-5-methyl-pyrazol-1-yl]-1,1-dimethyl-propylamino}-acetyl)-pyrrodine-2-carbonitrile, methanesulfonic acid salt This compound was made in analogy to example 80, steps A] to D] from 3-chloro-acetophenone, ethyl acetate, 4,4-dimethyl-2,2-dioxo-2λ'-[1,2,3]oxathiazinane-3-carboxylic acid tert-butyl ester and IIA as a methanesulfonic acid addition salt.

MS (ISP): 414.5 (MH$^+$, free base).

Example 86

(2S)-1-({3-[3-(3,4-Dichloro-phenyl)-5-methyl-pyrazol-1-yl]-1,1-dimethyl-propylamino]-acetyl)-pyrrolidine-2-carbonitrile, methanesulfonic acid salt This compound was made in analogy to example 80, steps A] to D] from 3,4-dichloro-acetophenone, ethyl acetate, 4,4-dimethyl-2,2-dioxo-2λ'-[1,2,3]oxathiazinane-3-carboxylic acid tert-butyl ester and IIA as a methanesulfonic acid addition salt.

MS (ISP): 448.4 (MH$^+$, free base).

Example 87

(2S)-1-{[1,1-Dimethyl-3-(3-phenyl-5-trifluoromethyl-pyrazol-1-yl)-propylamino]-acetyl}-pyrrolidine-2-carbonitrile, methanesulfonic acid salt This compound was made in analogy to example 78, steps C] to E] from commercially available 3-phenyl-5-(trifluoromethyl)-1H-pyrazole, 4,4-dimethyl-2,2-dioxo-2λ'-[1,2,3]oxathiazinane-3-carboxylic acid tert-butyl ester and IIA as a methanesulfonic acid addition salt.

MS (ISP): 434.5 (MH$^+$, free base).

Example 88

(2S)-{[3-(5-Isopropyl-3-phenyl-pyrazol-1-yl)-1,1-dimethyl-propylamino]-acetyl}-pyrrolidine-2-carbonitrile, methanesulfonic acid salt This compound was made in analogy to example 80, steps A] to D] from acetophenone, ethyl 2-methyl-propionic acid, 4,4-dimethyl-2,2-dioxo-2λ'-[1,2,3]oxathiazinane-3-carboxylic acid tert-butyl ester and IIA as a methanesulfonic acid addition salt.

MS (ISP): 408.5 (MH$^+$, free base).

Example 89

(2S)-1-{[1,1-Dimethyl-3-(5-methyl-3-thiophen-2-yl-pyrazol-1-yl)-propylamino]-acetyl}-pyrrolidine-2-carbonitrile, methanesulfonic acid salt This compound was made in analogy to example 83, steps A] to D] from methyl thiophene-2-carboxylic acid, acetone, 4,4-dimethyl-2,2-dioxo-2λ'-[1,2,3]oxathiazinane-3-carboxylic acid tert-butyl ester and IIA as a methanesulfonic acid addition salt.

MS (ISP): 386.4 (MH$^+$, free base).

Example 90

(2S)-1-{[1,1-Dimethyl-3-(5-methyl-3-pyridin-4-yl-pyrazol-1-yl)-propylamino]-acetyl}-pyrrolidine-2-carbonitrile, methanesulfonic acid salt This compound was made in analogy to example 83, steps A] to D] from methyl isonicotinic acid, acetone, 4,4-dimethyl-2,2-dioxo-2λ'-[1,2,3]oxathiazinane-3-carboxylic acid tert-butyl ester and IIA as a methanesulfonic acid addition salt.

MS (ISP): 381.4 (MH$^+$, free base).

Example 91

(2S)-1-({1,1-Dimethyl-3-[5-methyl-3-(6-methyl-pyridin-3-yl)-pyrazol-1-yl]-propylamino}-acetyl)-pyrrolidine-2-carbonitrile methanesulfonic acid salt This compound was made in analogy to example 83, steps A] to D] from methyl 6-methylnicotinic acid, acetone, 4,4-dimethyl-2,2-dioxo-2λ'-[1,2,3]oxathiazinane-3-carboxylic acid tert-butyl ester and IIA as a methanesulfonic acid addition salt.

MS (ISP): 395.3 (MH$^+$, free base).

Example 92

(2S)-1-{[3-(5-Cyclopropyl-3-phenyl-pyrazol-1-yl)-1,1-dimethyl-propylamino]-acetyl}-pyrrolidine-2-carbonitrile, methanesulfonic acid salt This compound was made in analogy to example 80, steps A] to D] from acetophenone, ethyl cyclopropanecarboxylic acid, 4,4-dimethyl-2,2-dioxo-2λ-[1,2,3]oxathiazinane-3-carboxylic acid tert-butyl ester and IIA as a methanesulfonic acid addition salt.

MS (ISP): 406.4 (MH$^+$, free base).

Example 93

(2S)-1-{[1,1-Dimethyl-3-(5-methyl-3-pyrazin-2-yl-pyrazol-1-yl)-propylamino]-acetyl}-pyrrolidine-2-carbonitrile, methanesulfonic acid salt This compound was made in analogy to example 83, steps A] to D] from methyl pyrazinecarboxylic acid, acetone, 4,4-dimethyl-2,2-dioxo-2λ'-[1,2,3]oxathiazinane-3-carboxylic acid tert-butyl ester and IIA as a methanesulfonic acid addition salt.

MS (ISP): 382.3 (MH$^+$, free base).

Example 94

(2S)-1-({3-[3-(5-Chloro-pyridin-3-yl)-5-methyl-pyrazol-1-yl]-1,1-dimethyl-propylamino}-acetyl)-pyrrolidine-2-carbonitrile, methanesulfonic acid salt This compound was made in analogy to example 83, steps A] to D] from methyl 3-chloropyridine-5-carboxylic acid (synthesized from methyl 3-chloropyridine-5-carboxylic acid according to Meyer et al., *Chem. Ber.* 1928, 61, 2211), acetone, 4,4-dimethyl-2,2-dioxo-2λ'-[1,2,3]oxathiazinane-3-carboxylic acid tert-butyl ester and IIA as a methanesulfonic acid addition salt.

MS (ISP): 415.4 (MH+, free base).

Example 95
(2S)-1-{[1,1-Dimethyl-3-(5-methyl-3-pyridin-2-yl-pyrazol-1-yl)-propylamino]-acetyl}-pyrrolidine-2-carbonitrile, methanesulfonic acid salt This compound was made in analogy to example 83, steps A] to D] from methyl pyridine-2-carboxylic acid, acetone, 4,4-dimethyl-2,2-dioxo-2λ'-[1,2,3]oxathiazinane-3-carboxylic acid tert-butyl ester and IIA as a methanesulfonic acid addition salt.

MS (ISP): 381.3 (MH+, free base).

Example 96
(2S)-1-{[1,1-Dimethyl-3-(3-pyridin-3-yl-5-trifluoromethyl-pyrazol-1-yl)-propylamino]-acetyl}-pyrrolidine-2-carbonitrile, methanesulfonic acid salt Step A]: 3-(5-Trifluoromethyl-1H-pyrazol-3-yl)-pyridine This compound known previously in the literature was made in analogy to Katsuyama et al., *Synthesis* 1997, 1321: 3-Acetyl-pyridine (1.21 g) was dissolved in benzene (10 ml) and potassium-tert-butoxide (1.35 g) was added under argon. The suspension was cooled to 0° C. and trifluoroacetic acid ethyl ester (1.43 ml) was added drop by drop. The color and the texture of the suspension changed within 10 min and the resulting mixture was allowed to stir at RT for 60 min. Water (50 ml) was added and the solids were dissolved. Acetic acid (2.5 ml) was added and a yellow precipitate was observed. Ethyl acetate was added and the material was partly soluble in the organic layer. The clear aqueous layer was separated and the suspension in the organic layer was concentrated in vacuo. The residue was suspended in ethanol/water 1:1 (50 ml) and treated with hydrazine monohydrate (0.61 ml). The solution was heated to reflux and gradually cleared to become a clear solution. Acetic acid (2 ml) was added and heating was continued for 5 h. The solution was then cooled, poured into brine and basified with saturated $Na_2CO_3$ solution. The aqueous layer was extracted with ethyl acetate and the organic layer was separated, washed with brine, dried and evaporated to give a crude product. This solid was triturated with ether (5 ml) for 30 min and filtered. The resulting solid was dried in vacuo. (Yield: 1.4 g).

MS (ISP): 214.1 (MH+).

Steps B] to D]: (2S)-1-{[1,1-Dimethyl-3-(3-pyridin-3-yl-5-trifluoromethyl-pyrazol-1yl)-acetyl}-pyrrolidine-2-carbonitrile, methanesulfonic acid salt This compound was made in analogy to example 78, steps C] to E] from 3-(5-trifluoromethyl-1H-pyrazol-3-yl)-pyridine (from step A]), 4,4-dimethyl-2,2-dioxo-2λ'-[1,2,3]oxathiazinane-3-carboxylic acid tert-butyl ester and IIA as a methanesulfonic acid addition salt.

MS (ISP): 435.4 (MH+, free base).

Example 97
(2S)-1-{[1,1-Dimethyl-3-(3-pyridin-3-yl-pyrazol-1-yl)-propylamino]-acetyl}-pyrrolidine-2-carbonitrile, methanesulfonic acid salt This compound was made in analogy to example 78, steps C] to D] from 3-(1H-pyrazol-3-yl)-pyridine (synthesized according to the literature: Plate et al., *Bioorg. Med. Chem.* 1996, 4 (2), 227 and Schunack, *Arch. Pharm.* 1973, 306, 934, 941), 4,4-dimethyl-2,2-dioxo-2λ'-[1,2,3]oxathiazinane-3-carboxylic acid tert-butyl ester and IIA as a methanesulfonic acid addition salt.

MS (ISP): 367.3 (MH+, free base).

Example 98
(2S)-1-{[1,1-Dimethyl-3-(5-methyl-3-pyridin-3-yl-[1,2,4]triazol-1-yl)-propylamino]-acetyl}-pyrrolidine-2-carbonitrile, methanesulfonic acid salt

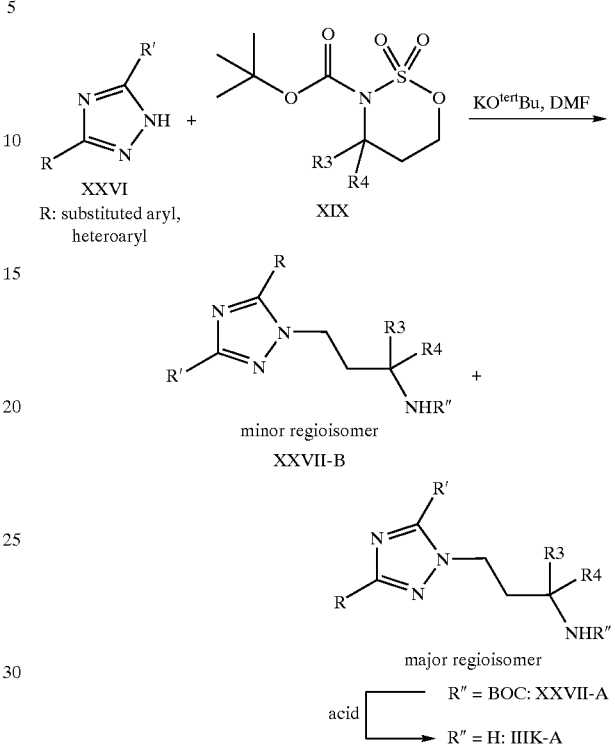

Synthesis of this type of compound required the preparation of the corresponding amine precursor IIIK. This compound is accessible in analogy to the synthesis of the pyrazol type amines IIIH by replacing the pyrazole starting materials XXII with [1,2,4]triazoles XXVI. [1,2,4]triazoles XXVI used in examples 98–100 are commercially available, known in the literature or were prepared in analogy to literature procedures. Similarly, regioisomers (e.g. XXVII-A and XXVII-B) may be formed in the alkylation of XXVI that are isolated individually, deprotected by acid treatment to give amines IIIK. Amines IIIK are subsequently used in the final coupling step with IIA to give cyanopyrrolidine I.

The title compound was obtained in analogy to example 78, steps C] to E] by replacing 5-methyl-3-phenyl-1H-pyrazole with 3-(5-methyl-1H-[1,2,4]triazol-3-yl)-pyridine that was synthesized according to the literature (Francis et al, *Tetrahedron Lett.* 1987, 28 (43), 5133). The compound was obtained as a methanesulfonic acid addition salt.

MS (ISP): 382.3 (MH+, free base).

Example 99
(2S)-1-{[1,1-Dimethyl-3-(3-pyridin-3-yl-5-trifluoromethyl-[1,2,4]triazol-1-yl)-propylamino]-acetyl}-pyrrolidine-2-carbonitrile, methanesulfonic acid salt Step A]: 3-(5-Trifluoromethyl-1H-[1,2,4]triazol-3-yl)-pyridine Hydrazine monohydrate (0.34 ml) was dissolved in ethanol (6 ml). Ethyl trifluoroacetate (0.83 ml) was added dropwise over a period of 15 min at 0° C. and the resulting mixture was allowed to stir for 90 min at 0° C. The solution was concentrated to about 20% of the initial volume in vacuo at 35° C. and the trifluoroacetic acid hydrazide obtained that way was used without further purification.

Nicotinamidine hydrochloride (1.5 g) was suspended in ethanol (8 ml) and a suspension of sodium methoxide (514 mg) in 4 ml ethanol was added slowly. The resulting suspension was allowed to stir for 60 min at RT and then filtered. To the filtrate was added the ethanolic solution of trifluoroacetic acid hydrazide made previously by syringe and the syringe was washed with a small amount of ethanol. The resulting solution is then allowed to stir at RT for 4 days under argon. A 1:1 mixture of ether and hexanes (approx. 25 ml) was added to the solution and the solvent was decanted from an oily precipitate and concentrated in vacuo to leave crude trifluoroacetic acid N'-(imino-pyridin-3-yl-methyl)-hydrazide (759 mg) as a semisolid.

This material was treated in analogy to the literature (Evans et al., U.S. Pat. No. 4,038,405, 1977) with 3 N NaOH solution (12 ml) under reflux for 1.5 h and the resulting mixture was allowed to stir at RT over night. The suspension was filtered and the solid was washed with cold water and dried in vacuo. The residue was triturated with hexanes (10 ml), filtered and dried to give the title compound as a colorless solid (180 mg).

$^1$H-NMR (DMSO-d$_6$): 7.35 (dd, J=7.6, 4.0 Hz, 1H), 8.24 (dt, J=8.0, 2.0 Hz, 1H), 8.41 (dd, J=4.8, 1.6 Hz, 1H), 9.13 (d, J=1.6Hz, 1H); MS (ESI—): 212.9 ([M−H]$^-$).

Steps B] to E]: (2S)-1-{[1,1-Dimethyl-3-(3-pyridin-3-yl-5-trifluoromethyl-[1,2,4]trazol-1-yl)-propylamino]-acetyl}-pyrrolidine-2-carbonitrile, methanesulfonic acid salt The title compound was obtained in analogy to example 78, steps C] to E] by replacing 5-methyl-3-phenyl-1H-pyrazole with 3-(5-trifluoromethyl-1H-[1,2,4]triazol-3-yl)-pyridine from step A]. The desired cyanopyrrolidine was obtained as a methanesulfonic acid addition salt as a light yellow, hygroscopic solid.

MS (ISP): 436.4 (MH$^+$, free base).

Example 100

(2S)-1-{[1,1-Dimethyl-3-(5-methyl-3-pyrazin-2-yl-[1,2,4]triazol-1-yl)-propylamino]-acetyl}-pyrrolidine-2-carbonitrile This compound was made in analogy to example 78, steps C] to E] by replacing 5-methyl-3-phenyl-1H-pyrazole with 2-(5-methyl-1H-[1,2,4]triazol-3-yl)-pyrazine. This compound known in the literature was prepared from pyrazine-2-carboxylic acid hydrazide (Reich et al., *J. Med. Chem.* 1989, 32 (11), 2474) in analogy to Francis et al., *Tetrahedron Lett.* 1987, 28 (43), 5133. The title compound was obtained as the free base as a colorless oil.

MS (ISP): 383.3 (MH$^+$).

Example 101

(2S)-1-{[1,1-Dimethyl-3-(2-methyl-benzoimidazol-1-yl)-propylamino]-acetyl}-pyrrolidine-2-carbonitrile

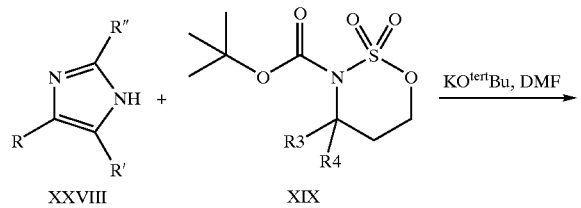

XXVIII  XIX
R = aryl, heteroaryl;
R' = H
R, R' = annelated aryl

-continued

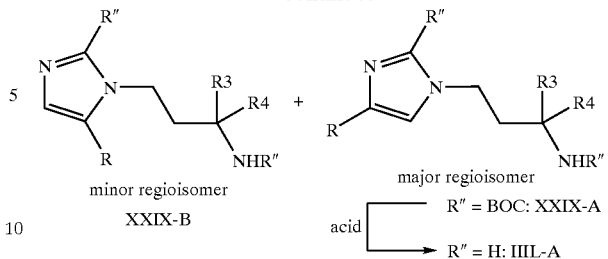

minor regioisomer  major regioisomer
XXIX-B
acid  R" = BOC: XXIX-A
R" = H: IIIL-A Synthesis of this compound required the preparation of the corresponding amine precursor IIIL. This compound is accessible in analogy to the synthesis of the pyrazol type amines IIIH by replacing the pyrazole starting materials XXII with imidazoles XXVIII. Imidazoles XXVIII used in examples 101–105 are commercially available, known in the literature or were prepared in analogy to literature procedures. Similarly, regioisomers (e.g. XXIX-A and XXIX-B) may be formed in the alkylation of XXVIII that are isolated individually, deprotected by acid treatment to give amines IIIL. Amines IIIL are subsequently used in the final coupling step with IIA to furnish cyanopyrrolidines I.

The title compound was obtained in analogy to example 78, steps C] to E] by replacing 5-methyl-3-phenyl-1H-pyrazole with commercially available 2-methylbenzimidazole. The desired compound was obtained as the free amine as a glass.

MS (ISP): 354.3 (MH$^+$).

Example 102

(2S)-1-{[1,1-Dimethyl-3-(2-methyl-4-pyridin-3-yl-imidazol-1-yl)-propylamino]-acetyl}-pyrrolidine-2-carbonitrile Step A]: 3-(2-Methyl-1H-imidazol-4-yl)-pyridine Bromoacetylpyridine hydrobromide (1.0 g) and acetamidine hydrochloride (0.505 g) were suspended in methanol. Potassium tert-butoxide (1.0 g) was added in one portion—the mixture turned slightly yellow. The resulting suspension was heated to reflux for 6 hours and was then cooled and filtered. Solvent was removed in vacuo and the residue was dissolved in CHCl$_3$ and adsorbed onto silica gel that was charged onto a silica gel column. The column was eluted with CH$_2$Cl$_2$/MeOH/NH$_4$OH 90:10:1 and the fractions containing the desired product were combined and evaporated to give an oil (79 mg).

$^1$H-NMR (CDCl$_3$): 2.50 (s, 3H), 7.27 (s, 1H), 7.30 (m, 1H), 8.05 (m, 1H), 8.46 (m, 1H), 8.93 (m, 1H).

Steps B] to D]: (2S)-1-{[1,1-Dimethyl-3-(2-methyl-4-pyridin-3-yl-imidazol-1-yl)-propylamino-acetyl}-pyrrolidine-2-carbonitrile The title compound was obtained in analogy to example 78, steps C] to E] by replacing 5-methyl-3-phenyl-1H-pyrazole with 3-(2-methyl-1H-imidazol-4-yl)-pyridine obtained in Step A]. The desired compound was obtained as the free amine as a glass.

MS (ISP): 381.3 (MH$^+$).

Example 103

(2S)-1-{[1,1-Dimethyl-3-(4-phenyl-imidazol-1-yl)-propylamino]-acetyl}-pyrrolidine-2-carbonitrile, methanesulfonic acid salt The title compound was obtained in analogy to example 78, steps C] to E] by replacing 5-methyl-3-phenyl-1H-pyrazole with commercially available 4-phenyl-1H-imidazole. The desired compound was obtained as the methanesulfonic acid addition salt.

MS (ISP): 366.2 (MH$^+$, free base).

Example 104
(2S)-1-{[1,1-Dimethyl-3-(4-pyridin-2-yl-imidazol-1-yl)-propylamino]-acetyl}-pyrrolidine-2-carbonitrile, methanesulfonic acid salt Step A] 2-(1H-Imidazol-4-yl)-pyridine This compound known in the literature was made by an alternative route in analogy to *Heterocycles* 1994, 39 (1), 139: Tosylmethylisocyanide (TOSMIC) (3.57 g) was suspended in ethanol (50 ml) and 2-picolinealdehyde (2.0 g) was added. Sodium cyanide (92 mg) was added in one portion at 15° C. and the mixture was allowed to stir—the internal temperature rose to 26° C. and a clear solution was obtained. The mixture was cooled again to 15° C. and the intermediate oxazoline derivative precipitated. The suspension was filtered and the solid intermediate was washed with ether/hexanes 1:1 and dried in vacuo (yield: 4.77 g).

This material was dissolved in 7M $NH_3$ in methanol (125 ml) and heated at 100° C. for 24 h in a sealed tube. The mixture was cooled, evaporated in vacuo and the residue was purified by flash chromatography to give the desired compound as an oil (1.56 g).

MS (ISP): 146.2 ($MH^+$).

Steps B] to D]: (2S)-1-{[1,1-Dimethyl-3-(4-pyridin-2-yl-imidazol-1-yl)-propylamino]-acetyl}-pyrrolidine-2-carbonitrile, methanesulfonic acid salt The title compound was obtained in analogy to example 78, steps C] to E] by replacing 5-methyl-3-phenyl-1H-pyrazole with 2-(1H-imidazol-4-yl)-pyridine obtained in step A]. The desired compound was obtained as a methanesulfonic acid addition salt.

MS (ISP): 367.3 ($MH^+$, free base).

Example 105
(2S)-1-{[1,1-Dimethyl-3-(4-pyridin-3-yl-imidazol-1-yl)-propylamino]-acetyl}-pyrrolidine-2-carbonitrile, methanesulfonic acid salt The title compound was obtained in analogy to the previous example 104, steps A] to D] from pyridine-3-carboxaldehyde as an initial starting material. The desired compound was obtained as a methanesulfonic acid addition salt.

MS (ISP): 367.2 ($MH^+$, free base).

Example 106
(2S)-1-[(6R/S)-(2-Methoxy-5,6,7,8-tetrahydro-quinolin-6-ylamino)-acetyl]-pyrrolidine-2-carbonitrile, methanesulfonic acid salt Step A]: 2-Methoxy-7,8-dihydro-5H-quinolin-6-one oxime 2-Methoxy-7,8-dihydro-5H-quinolin-6-one (246 mg, synthesized according to *J. Org. Chem.* 1991, 56 (15), 4636) was dissolved in ethanol/water 1:1 (14 ml) and sodium acetate (600 mg) and hydroxylamine hydrochloride (482 mg) was added. The resulting suspension was heated to reflux for 4 hours until TLC analysis confirmed complete consumption of the starting tetrahydroquinolinone. The reaction mixture was poured into a mixture of ice, water and 1N NaOH (pH>10) and the aqueous layer was extracted with ethyl acetate. The organic layer was separated, washed with brine, dried and evaporated to give a crude product. This was purified by flash chromatography (gradient of ethyl acetate in hexanes, 20% to 50%) to give the desired product as a mixture of (E/Z)-isomers (232 mg) as a yellow solid.

Mp: 124–126° C. MS (ISP): 193.1 ($MH^+$).

Step B] to C]: (2S)-1-[(6R/S)-(2-Methoxy-5,6,7,8-tetrahydro-quinolin-6-ylamino)-acetyl]-pyrrolidine-2-carbonitrile, methanesulfonic acid salt (mixture of 2 diastereomers)

This compound was synthesized as a mixture of 2 diastereomers in analogy to example 2, steps A] to B] from 2-methoxy-7,8-dihydro-5H-quinolin-6-one oxime, 4,4-dimethyl-2,2-dioxo-2λ'-[1,2,3]oxathiazinane-3-carboxylic acid tert-butyl ester and IIA as a methanesulfonic acid addition salt.

MS (ISP): 315.3 ($MH^+$, free base).

Example 107
(2S)-1-{[1,1-Dimethyl-3-(5-cyano-2-methyl-indol-1-yl)-propylamino]-acetyl}-pyrrolidine-2-carbonitrile This compound was obtained in analogy to example 14 and example 78 (steps C] to E]), respectively, from 5-cyano-2-methyl-indole, 4,4-dimethyl-2,2-dioxo-2λ'-[1,2,3]oxathiazinane-3-carboxylic acid tert-butyl ester and IIA.

MS (ISP): 378.4 ($MH^+$).

Example 108
(2S)-1-{[(1S)-1-Methyl-2-(3-phenyl-pyrazol-1-yl)-ethylamino]-acetyl}-pyrrolidine-2-carbonitrile

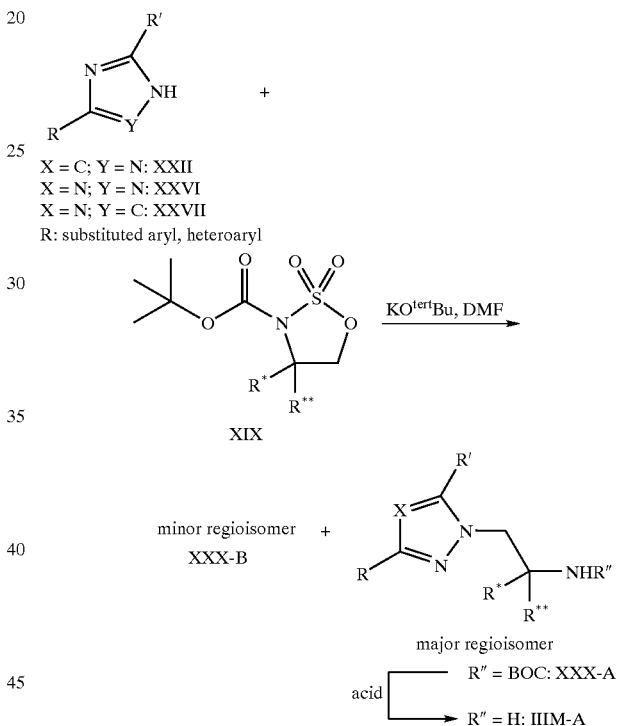

Synthesis of this compound required the preparation of amines IIIM, that can be prepared as described for the pyrazoles IIIH, triazoles IIIK and imidazols IIIL by replacing sulfimidate XIX with sulfimidate IV. Starting pyrazols XXII, [1,2,4]triazoles XXVI and imidazols XXVIII used in examples 108–112 are commercially available, are known or are prepared as described in the previous examples or in the individual examples that follow. Regioisomers (e.g. XXX-A) may be formed that are isolated individually, deprotected by acid treatment to give amines IIIM. Amines IIIM are subsequently used in the final coupling step with IIA to furnish cyanopyrrolidines I.

The above title compound was obtained in analogy to example 78, steps C] to E] by replacing 5-methyl-3-phenyl-1H-pyrazole with commercially available 3-phenyl-1H-pyrazole and by replacing sulfimidate XIX with IV and with the exception, that the final coupling step with IIA was done as described in example 1. The title compound was obtained as the free amine as a glass

MS (ISP): 338.3 ($MH^+$). .

Example 109
(2S)-1-({(1S)-2-[3-(4-Methoxy-phenyl)-pyrazol-1-yl]-1-methyl-ethylamino}-acetyl)-pyrrolidine-2-carbonitrile The title compound was obtained in analogy to example 78, steps C] to E] by replacing 5-methyl-3-phenyl-1H-pyrazole with commercially available 3-(4-methoxy-phenyl)-1H-pyrazole and by replacing sulfimidate XIX with IV and with the exception, that the final coupling step with IIA was done as described in example 1. The title compound was obtained as the free amine as a glass.

MS (ISP): 368.4 (MH$^+$).

Example 110
(2S)-1-({(1S)-2-[3-(4-Methoxy-phenyl)-[1,2,4]triazol-1-yl]-1-methyl-ethylamino}-acetyl)-pyrrolidine-2-carbonitrile The title compound was obtained in analogy to example 78, steps C] to E] from 3-(4-methoxy-phenyl)-1H-[1,2,4]triazole (Hoggarth et al., *J. Chem. Soc.* 1950, 1579-synthesized in analogy to Lin et al., *J. Org. Chem.* 1979, 44 (23), 4160, from 4-methoxy-benzamide) by replacing sulfimidate XIX with IV and with the exception, that the final coupling step with IIA was done as described in example 1. The title compound was obtained as the free amine as a glass.

MS (ISP): 369.4 (MH$^+$).

Example 111
(2S)-1-{[(1S)-1-Methyl-2-(5-methyl-3-phenyl-1,2,4]triazol-1-yl)-ethylamino]-acetyl}-pyrrolidine-2-carbonitrile The title compound was obtained in analogy to example 78, steps C] to E] from 5-methyl-3-phenyl-1H-[1,2,4]triazole (Francis et al., *Tetrahedron Lett.* 1987, 28; (43), 5133) by replacing sulfimidate XIX with IV and with the exception, that the final coupling step with IIA was done as described in example 1. The title compound was obtained as the free amine as a glass.

MS (ISP): 353.4 (MH$^+$).

Example 112
(2S)-1-{[(1S)-1-Methyl-2-(5-methyl-3-phenyl-pyrazol-1-yl)-ethylamino]-acetyl}-pyrrolidine-2-carbonitrile The title compound was obtained in analogy to example 78, steps C] to E] from 5-methyl-3-phenyl-1H-pyrazole by replacing sulfimidate XIX with IV and with the exception, that the final coupling step with IIA was done as described in example 1. The title compound was obtained as the free amine as a glass.

MS (ISP): 352.4 (MH$^+$).

Example 113
(2S)-1-{[1,1-Dimethyl-2-(5-phenyl-pyridin-2-ylamino)-ethylamino]-acetyl}-pyrrolidine-2-carbonitrile, hydrochloride salt This compound was obtained in analogy to example 36, steps A] to C] starting from 2,5-dibromopyridine, 1,2-diamino-2-methlypropane, phenylboronic acid and IIA. The residue obtained by flash chromatography was dissolved in dioxane and precipitated by treatment with HCl in dioxane yielding a white powder.

MS (ISP): 378.4 (MH+).

Example 114
(2S)-1-({2-[5-(3-Methoxy-phenyl)-pyridin-2-ylamino]-1,1-dimethyl-ethylamino}-acetyl)-pyrrolidine-2-carbonitrile, hydrochloride salt This compound was obtained in analogy to example 36, steps A] to C] starting from 2,5-dibromopyridine, 1,2-diamino-2-methlypropane, 3-methoxyphenylboronic acid and IIA. The residue obtained by flash chromatography was dissolved in THF and precipitated by treatment with HCl in ether yielding a white powder.

MS (ISP): 408.5 (MH+).

Example 115
(2S)-1-({2-[5-(4-Cyano-phenyl)-pyridin-2-ylamino]-1,1-dimethyl-ethylamino}-acetyl)-pyrrolidine-2-carbonitrile, hydrochloride salt This compound was obtained in analogy to example 36, steps A] to C] starting from 2,5-dibromopyridine, 1,2-diamino-2-methlypropane, 4-cyanophenylboronic acid and IIA. The residue obtained by flash chromatography was dissolved in THF and precipitated by treatment with HCl in ether yielding a white powder.

MS (ISP): 403.6 (MH+).

Example 116
(2S)-1-({2-[5-(2-Methoxy-phenyl)-pyridin-2-ylamino]-1,1-dimethyl-ethylamino}-acetyl)-pyrrolidine-2-carbonitrile, hydrochloride salt This compound was obtained in analogy to example 36, steps A] to C] starting from 2,5-dibromopyridine, 1,2-diamino-2-methlypropane, 2-methoxyphenylboronic acid and IIA. The residue obtained by flash chromatography was dissolved in THF and precipitated by treatment with HCl in ether yielding a white powder.

MS (ISP): 408.5 (MH+).

Example 117
(2S)-1-({2-[5-(3-Cyano-phenyl)-pyridin-2-ylamino]-1,1-dimethyl-ethylamino}-acetyl)-pyrrolidine-2-carbonitrile, hydrochloride salt This compound was obtained in analogy to example 36, steps A] to C] starting from 2,5-dibromopyridine, 1,2-diamino-2-methlypropane, 3-cyanophenylboronic acid and IIA. The residue obtained by flash chromatography was dissolved in THF and precipitated by treatment with HCl in ether yielding a white powder.

MS (ISP): 403.6 (MH+).

Example 118
(2S)-1-({2-[5-(3-Cyano-phenyl)-pyridin-2-ylamino]-ethylamino}-acetyl)-pyrrolidine-2-carbonitrile, hydrochloride salt This compound was obtained in analogy to example 36, steps A] to C] starting from 2,5-dibromopyridine, 1,2-diaminoethane, 3-cyanophenylboronic acid and IIA. The residue obtained by flash chromatography was dissolved in THF and precipitated by treatment with HCl in ether yielding a white powder.

MS (ISP): 375.5 (MH+).

Example 119
(2S)-1-({1,1-Dimethyl-2-[5-(3-trifluoromethyl-phenyl)-pyridin-2-ylamino]-ethylamino}-acetyl)-pyrrolidine-2-carbonitrile, methansolfonic acid salt This compound was obtained in analogy to example 36, steps A] to C] starting from 2,5-dibromopyridine, 1,2-diamino-2-methlypropane, 3-(trifluoromethyl)-phenylboronic acid and IIA. The residue obtained by flash chromatography was dissolved in tert-butyl methyl ether and precipitated by treatment with methanesulfonic acid yielding a white powder.

MS (ISP): 446.4 (MH+).

Example 120

(2S)-1-({1,1-Dimethyl-2-[5-(4-trifluoromethyl-phenyl)-pyridin-2-ylamino]-ethylamino}-acetyl)-pyrrolidine-2-carbonitrile, methansolfonic acid salt This compound was obtained in analogy to example 36, steps A] to C] starting from 2,5-dibromopyridine, 1,2-diamino-2-methlypropane, 4-(trifluoromethyl)-phenylboronic acid and IIA. The residue obtained by flash chromatography was dissolved in tert-butyl methyl ether and precipitated by treatment with methanesulfonic acid yielding a white powder.

MS (ISP): 446.3 (MH+).

Example 121

(2S)-1-({1,1-Dimethyl-2-[5-(2-trifluoromethyl-phenyl)-pyridin-2-ylamino]-ethylamino}-acetyl)-pyrrolidine-2-carbonitrile, methansolfonic acid salt This compound was obtained in analogy to example 36, steps A] to C] starting from 2,5-dibromopyridine, 1,2-diamino-2-methlypropane, 2-(trifluoromethyl)-phenylboronic acid and IIA. The residue obtained by flash chromatography was dissolved in tert-butyl methyl ether and precipitated by treatment with methanesulfonic acid yielding a white powder.

MS (ISP): 446.3 (MH+).

Example 122

(2S)-1-({2-[5-(3,5-Bis-trifluoromethyl-phenyl)-pyridin-2-ylamino]-1,1-dimethyl-ethylamino}-acetyl)-pyrrolidine-2-carbonitrile, methansolfonic acid salt This compound was obtained in analogy to example 36, steps A] to C] starting from 2,5-dibromopyridine, 1,2-diamino-2-methlypropane, 3,5-bis(trifluoromethyl)-phenylboronic acid and IIA. The residue obtained by flash chromatography was dissolved in tert-butyl methyl ether and precipitated by treatment with methanesulfonic acid yielding a white powder.

MS (ISP): 514.3 (MH+).

Example 123

(2S)-1-{[2-([3,3']Bipyridinyl-6-ylamino)-1,1-dimethyl-ethylamino]-acetyl}-pyrrolidine-2-carbonitrile, methansolfonic acid salt This compound was obtained in analogy to example 36, steps A] to C] starting from 2,5-dibromopyridine, 1,2-diamino-2-methlypropane, pyridine-3-boronic acid and IIA. The residue obtained by flash chromatography was dissolved in tert-butyl methyl ether and ethyl acetate and precipitated by treatment with methanesulfonic acid yielding a slightly yellow powder.

MS (ISP): 377.3 (MH+).

Example 124

(2S)-1-({2-[5-(2,4-Dimethoxy-phenyl)-pyridin-2-ylamino]-1,1-dimethyl-ethylamino}-acetyl)-pyrrolidine-2-carbonitrile, methansolfonic acid salt This compound was obtained in analogy to example 36, steps A] to C] starting from 2,5-dibromopyridine, 1,2-diamino-2-methlypropane, 2,4-dimethoxyphenylboronic acid and IIA. The residue obtained by flash chromatography was dissolved in tert-butyl methyl ether and ethyl acetate and precipitated by treatment with methanesulfonic acid yielding a slightly yellow powder.

MS (ISP): 438.5 (MH+).

Example 125

(2S)-1-({2-[6-(4-Methoxy-phenyl)-pyridin-2-ylamino]-ethylamino}-acetyl)-pyrrolidine-2-carbonitrile, hydrochloride salt This compound was obtained in analogy to example 36, steps A] to C] starting from 2,6-dibromopyridine, 1,2-diaminoethane, 4-methoxyphenylboronic acid and IIA. The residue obtained by flash chromatography was dissolved in THF and precipitated by treatment with HCl in ether yielding a white powder.

MS (ISP): 380.5 (MH+).

Example 126

(2S)-1-({2-[6-(4-Cyano-phenyl)-pyridin-2-ylamino]-ethylamino}-acetyl)-pyrrolidine-2-carbonitrile, hydrochloride salt This compound was obtained in analogy to example 36, steps A] to C] starting from 2,6-dibromopyridine, 1,2-diaminoethane, 4-cyanophenylboronic acid and IIA. The residue obtained by flash chromatography was dissolved in THF and precipitated by treatment with HCl in ether yielding a white powder.

MS (ISP): 375.5 (MH+).

Example 127

(2S)-1-({2-[6-(3-Methoxy-phenyl)-pyridin-2-ylamino]-ethylamino}-acetyl)-pyrrolidine-2-carbonitrile, hydrochloride salt This compound was obtained in analogy to example 36, steps A] to C] starting from 2,6-dibromopyridine, 1,2-diaminoethane, 3-methoxyphenylboronic acid and IIA. The residue obtained by flash chromatography was dissolved in THF and precipitated by treatment with HCl in ether yielding a white powder.

MS (ISP): 380.5 (MH+).

Example 128

(2S)-1-({2-[6-(4-Cyano-phenyl)-pyridin-2-ylamino]-1,1-dimethyl-ethylamino}-acetyl)-pyrrolidine-2-carbonitrile, hydrochloride salt This compound was obtained in analogy to example 36, steps A] to C] starting from 2,6-dibromopyridine, 1,2-diamino-2-methylpropane, 4-cyanophenylboronic acid and IIA. The residue obtained by flash chromatography was dissolved in THF and precipitated by treatment with HCl in ether yielding a white powder.

MS (ISP): 403.6 (MH+).

Example 129

(2S)-1-{[1,1-Dimethyl-2-(6-phenyl-pyridin-2-ylamino)-ethylamino]-acetyl}-pyrrolidine-2-carbonitrile, hydrochloride salt This compound was obtained in analogy to example 36, steps A] to C] starting from 2,6-dibromopyridine, 1,2-diamino-2-methylpropane, phenylboronic acid and IIA. The residue obtained by flash chromatography was dissolved in THF and precipitated by treatment with HCl in ether yielding a white powder.

MS (ISP): 378.4 (MH+).

Example 130

(2S)-1-({2-[6-(3-Cyano-phenyl)-pyridin-2-ylamino]-ethylamino}-acetyl)-pyrrolidine-2-carbonitrile, hydrochloride salt This compound was obtained in analogy to example 36, steps A] to C] starting from 2,6-dibromopyridine, 1,2-diaminoethane, 3-cyanophenylboronic acid and IIA. The residue obtained by flash chromatography was dissolved in

Example 131
(2S)-1-({2-[6-(3-Methoxy-phenyl)-pyridin-2-ylamino]-1,1-dimethyl-ethylamino}-acetyl)-pyrrolidine-2-carbonitrile, methansolfonic acid salt This compound was obtained in analogy to example 36, steps A] to C] starting from 2,6-dibromopyridine, 1,2-diamino-2-methlypropane, 3-methoxyphenylboronic acid and IIA. The residue obtained by flash chromatography was dissolved in THF and precipitated by treatment with methanesulfonic acid in ethyl acetate yielding a white powder.
MS (ISP): 408.5 (MH+).

Example 132
(2S)-1-({2-[6-(4-Methoxy-phenyl)-pyridin-2-ylamino]-1,1-dimethyl-ethylamino}-acetyl)-pyrrolidine-2-carbonitrile, methansolfonic acid salt This compound was obtained in analogy to example 36, steps A] to C] starting from 2,6-dibromopyridine, 1,2-diamino-2-methlypropane, 4-methoxyphenylboronic acid and IIA. The residue obtained by flash chromatography was dissolved in THF and precipitated by treatment with methanesulfonic acid in ethyl acetate yielding a white powder.
MS (ISP): 408.4 (MH+).

Example 133
(2S)-1-({2-[6-(2-Methoxy-phenyl)-pyridin-2-ylamino]-1,1-dimethyl-ethylamino}-acetyl)-pyrrolidine-2-carbonitrile, methansolfonic acid salt This compound was obtained in analogy to example 36, steps A] to C] starting from 2,6-dibromopyridine, 1,2-diamino-2-methlypropane, 2-methoxyphenylboronic acid and IIA. The residue obtained by flash chromatography was dissolved in THF and precipitated by treatment with methanesulfonic acid in ethyl acetate yielding a white powder.
MS (ISP): 408.4 (MH+).

Example 134
(2S)-1-({2-[6-(2-Methoxy-phenyl)-pyridin-2-ylamino]-ethylamino}-acetyl)-pyrrolidine-2-carbonitrile, methansolfonic acid salt This compound was obtained in analogy to example 36, steps A] to C] starting from 2,6-dibromopyridine, 1,2-diaminoethane, 2-methoxyphenylboronic acid and IIA. The residue obtained by flash chromatography was dissolved in THF and precipitated by treatment with methanesulfonic acid in tert-butyl methyl ether and ethyl acetate yielding a white powder.
MS (ISP): 380.5 (MH+).

Example 135
(2S)-1-({2-[6-(3-Cyano-phenyl)-pyridin-2-ylamino]-1,1-dimethyl-ethylamino}-acetyl)-pyrrolidine-2-carbonitrile, methansolfonic acid salt This compound was obtained in analogy to example 36, steps A] to C] starting from 2,6-dibromopyridine, 1,2-diamino-2-methlypropane, 3-cyanophenylboronic acid and IIA. The residue obtained by flash chromatography was dissolved in THF and precipitated by treatment with methanesulfonic acid in tert-butyl methyl ether and ethyl acetate yielding a white powder.
MS (ISP): 403.5 (MH+).

Example 136
(2S)-1-({2-[6-(3,5-Bis-trifluoromethyl-phenyl)-pyridin-2-ylamino]-1,1-dimethyl-ethylamino}-acetyl)-pyrrolidine-2-carbonitrile, methansolfonic acid salt This compound was obtained in analogy to example 36, steps A] to C] starting from 2,6-dibromopyridine, 1,2-diamino-2-methlypropane, 3,5-bis(trifluoromethyl)-phenylboronic acid and IIA. The residue obtained by flash chromatography was dissolved in THF and precipitated by treatment with methanesulfonic acid in ethyl acetate yielding a white powder.
MS (ISP): 514.3 (MH+).

Example 137
(2S)-1-(1,1-Dimethyl-2-[6-(4-trifluoromethyl-phenyl)-pyridin-2-ylamino]-ethylamino}-acetyl)-pyrrolidine-2-carbonitrile, methansolfonic acid salt This compound was obtained in analogy to example 36, steps A] to C] starting from 2,6-dibromopyridine, 1,2-diamino-2-methlypropane, 4-trifluoromethyl-phenylboronic acid and IIA. The residue obtained by flash chromatography was dissolved in THF and precipitated by treatment with methanesulfonic acid in ethyl acetate yielding a white powder.
MS (ISP): 446.4 (MH+).

Example 138
(2S)-1-({1,1-Dimethyl-2-[6-(2-trifluoromethyl-phenyl)-pyridin-2-ylamino]-ethylamino}-acetyl)-pyrrolidine-2-carbonitrile, methansolfonic acid salt This compound was obtained in analogy to example 36, steps A] to C] starting from 2,6-dibromopyridine, 1,2-diamino-2-methlypropane, 2-trifluoromethyl-phenylboronic acid and IIA. The residue obtained by flash chromatography was dissolved in tert-butyl methyl ether and precipitated by treatment with methanesulfonic acid yielding a white powder.
MS (ISP): 446.4 (MH+).

Example 139
(2S)-1-({1,1-Dimethyl-2-[6-(3-trifluoromethyl-phenyl)-pyridin-2-ylamino]-ethylamino}-acetyl)-pyrrolidine-2-carbonitrile, methansolfonic acid salt This compound was obtained in analogy to example 36, steps A] to C] starting from 2,6-dibromopyridine, 1,2-diamino-2-methlypropane, 3-trifluoromethyl-phenylboronic acid and IIA. The residue obtained by flash chromatography was dissolved in tert-butyl methyl ether and precipitated by treatment with methanesulfonic acid yielding a white powder.
MS (ISP): 446.4 (MH+).

Example 140
(2S)-1-{[2-([2,3']Bipyridinyl-6-ylamino)-1,1-dimethyl-ethylamino]-acetyl}-pyrrolidine-2-carbonitrile, methansolfonic acid salt This compound was obtained in analogy to example 36, steps A] to C] starting from 2,6-dibromopyridine, 1,2-diamino-2-methlypropane, pyridine-3-boronic acid and IIA. The residue obtained by flash chromatography was dissolved in tert-butyl methyl ether and precipitated by treatment with methanesulfonic acid yielding a white powder.
MS (ISP): 379.5 (MH+).

Example 141
(2S)-1-({2-[6-(2,4-Dimethoxy-phenyl)-pyridin-2-ylamino]-1,1-dimethyl-ethylamino}-acetyl)-pyrrolidine-2-carbonitrile, methansolfonic acid salt This compound was obtained in analogy to example 36, steps A] to C] starting from 2,6-dibromopyridine, 1,2-diamino-2-methlypropane, 2,4-dimethoxyphenylboronic acid and IIA. The residue obtained by flash chromatography was dissolved in ethyl acetate and tert-butyl methyl ether and precipitated by treatment with methanesulfonic acid yielding a white powder.

MS (ISP): 438.5 (MH+).

Example 142

(2S)-1-{[1,1-Dimethyl-2-(6-m-tolyl-pyridin-2-ylamino)-ethylamino]-acetyl}-pyrrolidine-2-carbonitrile, methanesulfonic acid salt This compound was obtained in analogy to example 36, steps A] to C] starting from 2,6-dibromopyridine, 1,2-diamino-2-methlypropane, 3-methylphenylboronic acid and IIA. The residue obtained by flash chromatography was dissolved in ethyl acetate and tert-butyl methyl ether and precipitated by treatment with methanesulfonic acid yielding a white powder.

MS (ISP): 392.3 (MH+).

Example 143

(2S)-1-{[1,1-Dimethyl-2-(5-phenyl-pyrimidin-2-ylamino)-ethylamino]-acetyl}-pyrrolidine-2-carbonitrile This compound was obtained in analogy to example 36, steps A] to C] starting from 5-bromo-2-iodopyrimidine, 1,2-diamino-2-methlypropane, phenylboronic acid and IIA. It was isolated as its free amine, as a slightly brown glass.

MS (ISP): 379.5 (MH+).

Example 144

(2S)-1-({2-[5-(3-Methoxy-phenyl)-pyrimidin-2-ylamino]-1,1-dimethyl-ethylamino}-acetyl)-2-carbonitrile This compound was obtained in analogy to example 36, steps A] to C] starting from 5-bromo-2-iodopyrimidine, 1,2-diamino-2-methlypropane, 3-methoxyphenylboronic acid and IIA. It was isolated as its free amine, as a slightly yellow foam.

MS (ISP): 409.5 (MH+).

Example 145

(2S)-1-({2-[5-(3-Cyano-phenyl)-pyrimidin-2-ylamino]-1,1-dimethyl-ethylamino}-acetyl)-pyrrolidine-2-carbonitrile This compound was obtained in analogy to example 36, steps A] to C] starting from 5-bromo-2-iodopyrimidine, 1,2-diamino-2-methlypropane, 3-cyanophenylboronic acid and IIA. It was isolated as its free amine, as a slightly brown foam.

MS (ISP): 404.5 (MH+).

Example 146

(2S)-1-({2-[5-(4-Cyano-phenyl)-pyrimidin-2-ylamino]-1,1-dimethyl-ethylamino}-acetyl)-pyrrolidine-2-carbonitrile This compound was obtained in analogy to example 36, steps A] to C] starting from 5-bromo-2-iodopyrimidine, 1,2-diamino-2-methlypropane, 4-cyanophenylboronic acid and IIA. It was isolated as its free amine, as a slightly yellow foam.

MS (ISP): 404.5 (MH+).

Example 147

(2S)-1-({2-[4-(2,4-Dimethoxy-phenyl)-thiazol-2-ylamino]-ethylamino}-acetyl)-pyrrolidine-2-carbonitrile This compound was prepared in analogy to example 47, steps A] to C] starting from (2-thioureido-ethyl)-carbamic acid tert-butyl ester [CAS 331779-96-5], 2-bromo-2',4'-dimethoxyacethophenone and IIA. It was isolated as its free amine, as a light yellow glass.

MS (ISP): 416.4 (MH+).

Example 148

(2S)-1-({2-[4-(2-Methoxy-phenyl)-thiazol-2-ylamino]-ethylamino}-acetyl)-pyrrolidine-2-carbonitrile This compound was prepared in analogy to example 47, steps A] to C] starting from (2-thioureido-ethyl)-carbamic acid tert-butyl ester [CAS 331779-96-5], 2-methoxyphenacyl bromide and IIA. It was isolated as its free amine, as a light yellow glass.

MS (ISP): 386.4 (MH+).

Example 149

(2S)-1-{[2-(4-Phenyl-thiazol-2-ylamino)-ethylamino]-acetyl}-pyrrolidine-2-carbonitrile This compound was prepared in analogy to example 47, steps A] to C] starting from (2-thioureido-ethyl)-carbamic acid tert-butyl ester [CAS 331779-96-5], 2-bromoacetophenone and IIA. It was isolated as its free amine, as a light yellow glass.

MS (ISP): 356.4 (MH+).

Example 150

(2S)-1-({2-[4-(3-Methoxy-phenyl)-thiazol-2-ylamino]-ethylamino}-acetyl)-pyrrolidine-2-carbonitrile This compound was prepared in analogy to example 47, steps A] to C] starting from (2-thioureido-ethyl)-carbamic acid tert-butyl ester [CAS 331779-96-5], 2-bromo-3'-methoxyacethophenone and IIA. It was isolated as its free amine, as a light yellow glass.

MS (ISP): 386.4 (MH+).

Example 151

(2S)-1-{[2-(8H-Indeno[1,2-d]thiazol-2-ylamino)-ethylamino]-acetyl}-pyrrolidine-2-carbonitrile, hydrochloride salt This compound was prepared in analogy to example 47, steps A] to C] starting from (2-thioureido-ethyl)-carbamic acid tert-butyl ester [CAS 331779-96-5], 2-bromoindanone and IIA. The residue obtained by flash chromatography was dissolved in dioxane and precipitated by treatment with HCl in dioxane yielding a light yellow powder.

MS (ISP): 368.3 (MH+).

Example 152

(2S)-1-[2-(5-Methyl-4-phenyl-thiazol-2-ylamino)-ethylamino]-acetyl}-pyrrolidine-2-carbonitrile, hydrochloride salt This compound was prepared in analogy to example 47, steps A] to C] starting from (2-thioureido-ethyl)-carbamic acid tert-butyl ester [CAS 331779-96-5], 2-bromopropiophenone and IIA. The residue obtained by flash chromatography was dissolved in dioxane and precipitated by treatment with HCl in dioxane yielding a white powder.

MS (ISP): 370.4 (MH+).

Example 153

(2S)-1-{[2-(4,5-Diphenyl-thiazol-2-ylamino)-ethylamino]-acetyl}-pyrrolidine-2-carbonitrile, hydrochloride salt This compound was prepared in analogy to example 47, steps A] to C] starting from (2-thioureido-ethyl)-carbamic acid tert-butyl ester [CAS 331779-96-5], 2-bromo-2-phenylacethophenone and IIA. The residue obtained by flash chromatography was dissolved in dioxane and precipitated by treatment with HCl in dioxane yielding a white powder.

MS (ISP): 432.4 (MH+).

Example 154
(2S)-1-{[2-(4-Benzoyl-thiazol-2-ylamino)-ethylamino]-acetyl}-pyrrolidine-2-carbonitrile, methanesulfonic acid salt This compound was prepared in analogy to example 47, steps A] to C] starting from (2-thioureido-ethyl)-carbamic acid tert-butyl ester [CAS 331779-96-5], 3-bromo-1-phenyl-propane-1,2-dione and IIA. The residue obtained by flash chromatography was dissolved in ethyl acetate and precipitated by treatment with methanesulfonic acid yielding a white powder.

MS (ISP): 384.3 (MH+).

Example 155
(2S)-1-({2-[4-(4-Fluoro-phenyl)-thiazol-2-ylamino]-ethylamino}-acetyl)-pyrrolidine-2-carbonitrile This compound was prepared in analogy to example 47, steps A] to C] starting from (2-thioureido-ethyl)-carbamic acid tert-butyl ester [CAS 331779-96-5], 4-fluorophenacyl bromide and IIA. It was isolated as its free amine, as a white glass.

MS (ISP): 374.4 (MH+).

Example 156
(2S)-1-({2-[4-(4-Trifluoromethyl-phenyl)-thiazol-2-ylamino]-ethylamino}-acetyl)-pyrrolidine-2-carbonitrile This compound was prepared in analogy to example 47, steps A] to C] starting from (2-thioureido-ethyl)-carbamic acid tert-butyl ester [CAS 331779-96-5], 4-(trifluoromethyl)phenacyl bromide and IIA. It was isolated as its free amine, as a white foam.

MS (ISP): 424.4 (MH+).

Example 157
(2S)-1-{[2-(4-Pyridin-2-yl-thiazol-2-ylamino)-ethylamino]-acetyl}-pyrrolidine-2-carboninitrile This compound was prepared in analogy to example 47, steps A] to C] starting from (2-thioureido-ethyl)-carbamic acid tert-butyl ester [CAS 331779-96-5], 2-(bromoacetyl)-pyridine and IIA. It was isolated as its free amine, as a colorless oil.

MS (ISP): 357.3 (MH+).

Example 158
(2S)-1-{[2-(4-Pyridin-4-yl-thiazol-2-ylamino)-ethylamino]-acetyl}-pyrrolidine-2-carbonitrile This compound was prepared in analogy to example 47, steps A] to C] starting from (2-thioureido-ethyl)-carbamic acid tert-butyl ester [CAS 331779-96-5], 4-(bromoacetyl) pyridine and IIA. It was isolated as its free amine, as a slightly yellow foam.

MS (ISP): 357.3 (MH+).

Example 159
(2S)-1-({2-[5-Methyl-4-(4-trifluoromethyl-phenyl)-thiazol-2-ylamino]-ethylamino}-acetyl)-pyrrolidine-2-carbonitrile This compound was prepared in analogy to example 47, steps A] to C] starting from (2-thioureido-ethyl)-carbamic acid tert-butyl ester [CAS 331779-96-5], 2-bromo-1-(4-trifluoromethylphenyl)propan-1-one and IIA. It was isolated as its free amine, as a slightly yellow foam.

MS (ISP): 460.4 (MNa+), 438.4 (MH+).

Example 160
(2S)-1-({2-[4-(4-Cyano-phenyl)-5-methyl-thiazol-2-ylamino]-ethylamino}-acetyl)-pyrrolidine-2-carbonitrile This compound was prepared in analogy to example 47, steps A] to C] starting from (2-thioureido-ethyl)-carbamic acid tert-butyl ester [CAS 331779-96-5], 4-(2-bromo-propionyl)-benzonitril and IIA. It was isolated as its free amine, as a slightly yellow foam.

MS (ISP): 395.3 (MH+).

Example 161
(2S)-1-{[2-(4-Pyridin-3-yl-thiazol-2-ylamino)-ethylamino]-acetyl}-pyrrolidine-2-carbonitrile This compound was prepared in analogy to example 47, steps A] to C] starting from (2-thioureido-ethyl)-carbamic acid tert-butyl ester [CAS 331779-96-5], 3-(bromoacetyl)-pyridine and IIA. It was isolated as its free amine, as a slightly yellow oil.

MS (ISP): 357.3 (MH+).

Example 162
(2S)-1-({2-[4-(4-Cyano-phenyl)-thiazol-2-ylamino]-1,1-dimethyl-ethylamino}-acetyl)-pyrrolidine-2-carbonitrile, methanesulfonic acid salt This compound was prepared in analogy to example 47, steps A] to C] starting from (1,1-dimethyl-2-thioureido-ethyl)-carbamic acid tert-butyl ester, which was prepared as described below, 4-cyanophenacyl bromide and IIA. The residue obtained by flash chromatography was dissolved in ethyl acetate and precipitated by treatment with methanesulfonic acid yielding a white powder.

MS (ISP): 409.3 (MH+).

(1,1-Dimethyl-2-thioureido-ethyl)-carbamic acid tert-butyl ester

Step A]: [2-(3-Benzoyl-thioureido)-1,1-dimethyl-ethyl]-carbamic acid tert-butyl ester A solution of (2-amino-1,1-dimethyl-ethyl)-carbamic acid tert-butyl ester [CAS 320581-09-7] (43.9 g) and benzoyl isothiocyanate (31.8 ml) in THF (400 ml) was stirred at 60° C. overnight. The mixture was concentrated. Small amounts of toluene were added. Insoluble parts were filtered off and the remaining solution was concentrated. The residue was disolved in ethyl acetate and extracted with brine. The organic layer was dried (MgSO$_4$) and evaporated. Crystallisation of the obtained residue in toluene and hexane provided 53.0 g of white crystals.

MS (ISP): 352.3 (MH+).

Step B]: (1,1-Dimethyl-2-thioureido-ethyl)-carbamic acid tert-butyl ester

A solution of [2-(3-benzoyl-thioureido)-1,1-dimethyl-ethyl]-carbamic acid tert-butyl ester (53.0 g) and potassium carbonate (25.8 g) in MeOH (500 ml) and H$_2$O (300 ml) was refluxed 3 h. The mixture was concentrated. The residue was disolved in ethyl acetate and extracted with brine. The organic layer was dried (MgSO$_4$) and evaporated. Flash chromatography (toluene/ethyl acetate 1:1) provided 10.4 g of a white powder.

MS (ISP): 248.2 (MH+).
$^1$H-NMR (DMSO-d$_6$): 1.17 (s, 6H), 1.38 (s, 9H), 3.57 (d, 2H), 6.57 (broad s, 1H), 7.11 (board s, 2H).

Example 163
(2S)-1-{[2-(4,5,6,7-Tetrahydro-benzothiazol-2-ylamino)-ethylamino]-acetyl}-pyrrolidine-2-carbonitrile This compound was prepared in analogy to example 47, steps A] to C] starting from (2-thioureido-ethyl)-carbamic acid tert-butyl ester [CAS 331779-96-5], 2-bromo-cyclohexanone and IIA. It was isolated as its free amine, as a yellow foam.

MS (ISP): 334.2 (MH+).

Example 164
(2S)-1-{[1,1-dimethyl-2-(6-ethoxycarbonyl-4,5,6,7-tetrahydro-thiazolo[5,4-c]pyridine-2-ylamino)-ethylamino]-acetyl}-pyrrolidine-2-carbonitrile, methanesulfonic acid salt This compound was prepared in analogy to example 47, steps A] to C] starting from (1,1-dimethyl-2-thioureido-ethyl)-carbamic acid tert-butyl ester (cf example 162), ethyl 3-bromo-4-oxo-1-piperidinecarboxylate [95629-02-0] and IIA. The residue obtained by flash chromatography was dissolved in ethyl acetate and precipitated by treatment with methanesulfonic acid and tert-butyl methyl ether yielding a white powder.

MS (ISP): 435.5 (MH+).

$^1$H-NMR (DMSO-$d_6$): 1.19 (t, 3H), 1.30 (s, 6H), 2.06 (m, 2H), 2.21 (m, 2H), 2.33 (s, 3H), 3.52 (m, 3H), 3.62 (m, 3H), 4.10 (q, 2H) and (m, 2H), 4.38 (s, 2H), 4.85 (dd, 1H), 8.18 (broad s, 1H), 9.09 (broad s, 2H). (+Rotamer)

Example 165

(2S)-1-{[1,1-dimethyl-2-(6-acetyl-4,5,6,7-tetrahydro-thiazolo[5,4-cl pyridine-2-ylamino)-ethylamino-acetyl}-pyrrolidine-2-carbonitrile, methanesulfonic acid salt This compound was prepared in analogy to example 47, steps A] to C] starting from (1,1-dimethyl-2-thioureido-ethyl)-carbamic acid tert-butyl ester (cf example 162), 1-piperidinecarboxylic acid, 3-bromo-4-oxo-, 1,1-dimethylethyl ester [188869-05-8] and IIA, whereas after step B] the obtained 2-methyl-N'-(4,5,6,7-tetrahydro-thiazolo[5,4-c]pyridin-2-yl)-propane-1,2-diamine was converted to 1-[2-(2-amino-2-methyl-propylamino)-6,7-dihydro-4H-thiazolo [5,4-c]pyridin-5-yl]-ethanone as described below. This compound was used in step C]. The residue obtained by flash chromatography in step C] was dissolved in tert-butyl methyl ether and precipitated by treatment with methanesulfonic acid yielding a slightly yellow powder.

MS (ISP): 405.4 (MH+).

$^1$H-NMR (DMSO-$d_6$): 1.29 (s, 6H), 2.05 (m, 2H), 2.08 (s, 3H), 2.20 (m, 2H), 2.31 (s, 3H), 2.67 (m, 2H), 3.51 (m, 3H), 3.66 (m, 3H), 4.05 (m, 1H), 4.16 (m, 1H), 4.45 (d, 2H), 4.86 (dd, 1H), 8.0 (broad s, 1H), 9.10 (broad s, 2H). (+Rotamer)

1-[2-(2-Amino-2-methyl-propylamino)-6,7-dihydro-4H-thiazolo [5,4-c]pyridin-5-yl]-ethanone A solution of 2-methyl-N'-(4,5,6,7-tetrahydro-thiazolo [5,4-c]pyridin-2-yl)-propane-1,2-diamine (125 mg, obtained after step B]), acetylchloride (39 μl) and 4-dimethylamino-pyridine (3.4 mg) in methylene chloride (2 ml) was stirred 1 h at RT. A cold solution of 1 N sodium hydroxide was added and the mixture extracted with methylene chloride. The organic layer was dried (MgSO$_4$) and evaporated. Flash chromatography (methylene chloride/MeOH/NH$_4$OH) provided 58 mg of a colorless glass.

MS (ISP): 269.3 (MH+).

$^1$H-NMR (CDCl$_3$): 1.20 (s, 6H), 2.15 and 2.18 (2s, 3H), 2.64 and 2.70 (2t, 2H), 3.01 and 3.16 (2s, 2H), 3.71 and 3.86 (2t, 2H), 4.45 and 4.53 (2s, 2H).

Example 166

(2S)-1-{[2-(Benzothiazol-2-ylamino)-1,1-dimethyl-ethylamino]-acetyl}-pyrrolidine-2-carbonitrile

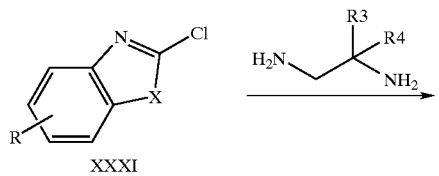

XXXI

-continued

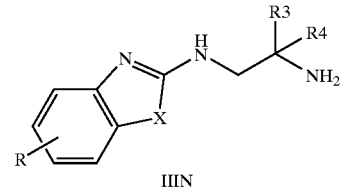

IIIN

X: S, O, NR

Synthesis of this compound requires the preparation of the corresponding amine precursor IIIN. A possible way for the preparation of IIIN is described in the general scheme above. According to this scheme a chloro-benzthiazole, -benzoxazole, or -imidazole XXXI is treated with the appropriate 1,2-diaminoethane.

Step A]: N1-Benzothiazol-2-yl-2-methyl-propane-1,2-diamine

A solution of 2-chlorobenzothiazole (5.0 g) in 1,2-diamino-2-methlypropane (20 ml) and pyridine (2.3 ml) was stirred 2 h at RT. The solvent was evaporated. Flash chromatography (silica gel; CH$_2$Cl$_2$/MeOH) provided 6.2 g of a colorless oil, which crystallized upon standing.

MS (ISP): 222.3 (MH$^+$).

$^1$H-NMR (CDCl$_3$): 1.21 (s, 6H), 3.32 (s, 2H), 5.90 (broad s, 1H), 7.07 (t, 1H), 7.53 (d, 1H), 7.57 (d, 1H).

Step B]: (2S)-1-{[2-(Benzothiazol-2-ylamino)-1,1-dimethyl-ethylamino]-acetyl}-pyrrolidine-2-carbonitrile The title compound was obtained from N1-benzothiazol-2-yl-2-methyl-propane-1,2-diamine (0.98 g) and IIA (0.24 g) following the procedure outlined in example 1, whereas DMF was added as solvent. The residue obtained by flash chromatography crystallized upon standing yielding 0.52 g of a white crystals.

MS (ISP): 358.3 (MH$^+$).

$^1$H-NMR (DMSO-$d_6$): 1.07 (s, 6H), 1.95–2.13 (m, 2H), 2.13–2.30 (m, 2H), 3.31–3.42 (m, 5H), 3.59 (m, 1H), 4.65 (dd, 1H), 6.99 (t, 1H), 7.19 (t, 1H), 7.33 (d, 1H), 7.63 (d, 1H), 7.88 (t,1H). (+Rotamer)

Example 167

(2S)-1-{[2-(Benzothiazol-2-ylamino)-ethylamino]-acetyl}-pyrrolidine-2-carbonitrile This compound was prepared in analogy to example 166, steps A] to B] starting from 2-chlorobenzothiazole, 1,2-diaminoethane and IIA. It was isolated as its free amine, as a white foam.

MS (ISP): 330.4 (MH$^+$).

Example 168

(2S)-1-{[2-(Benzooxazol-2-ylamino)-ethylamino]-acetyl}-pyrrolidine-2-carbonitrile This compound was prepared in analogy to example 166, steps A] to B] starting from 2-chlorobenzoxazole, 1,2-diaminoethane and IIA. It was isolated as its free amine, as a white foam.

MS (ISP): 314.3 (MH$^+$).

Example 169

(2S)-1-{[2-(Benzooxazol-2-ylamino)-1,1-dimethyl-ethylamino]-acetyl}-pyrrolidine-2-carbonitrile This compound was prepared in analogy to example 166, steps A] to B] starting from 2-chlorobenzoxazole, 1,2-diamino-2-methlypropane and IIA. It was isolated as its free amine, as a slightly brown foam.

MS (ISP): 342.3 (MH$^+$).

Example 170

(2S)-1-{[1,1-Dimethyl-2-(1-methyl-1H-benzoimidazol-2-ylamino)-ethylamino]-acetyl}-pyrrolidine-2-carbonitrile This compound was prepared in analogy to example 166, steps A] to B] starting from 2-chloro-1-methylbenzimidazole [CAS 1849-02-1], 1,2-diamino-2-methylpropane and IIA. It was isolated as its free amine, as a white foam.

MS (ISP): 355.3.3 (MH$^+$).

Example 171

(2S)-1-{[1,1-Dimethyl-2-(5-phenyl-[1,3,4]oxadiazol-2-ylamino)-ethylamino]-acetyl}-pyrrolidine-2-carbonitrile, methanesulfonic acid salt

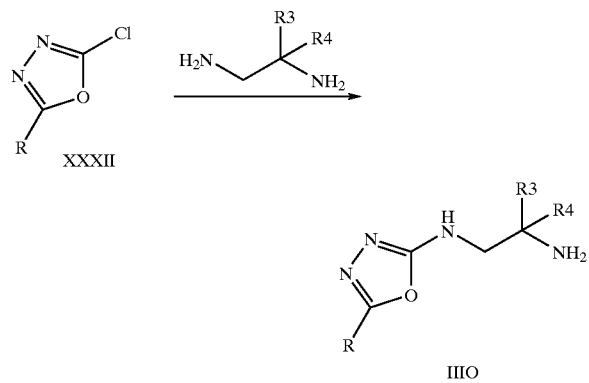

Synthesis of this compound requires the preparation of the corresponding amine precursor IIIO. A possible way for the preparation of IIIO is described in the general scheme above. According to this scheme a 2-chloro-[1,3,4] oxadiazole XXXII is treated with the appropriate 1,2-diaminoethane.

Step A]: 2-Methyl-N$^2$-(5-phenyl-[1,3,4]oxadiazol-2-yl)-propane-1,2-diamine

A solution of 2-chloro-5-phenyl-[1,3,4]oxadiazole (0.5 g; [CAS 1483-31-4]) and 1,2-diamino-2-methylpropane (0.88 ml) in 1-methyl-2-pyrrolidinone (5 ml) was stirred 1 h at RT. The solvent was evaporated. Flash chromatography (silica gel; CH$_2$Cl$_2$/MeOH/NH$_4$OH 90:9.5:0.5) provided 513 mg of a dark red foam.

MS (ISP): 233.2 (MH$^+$).

$^1$H-NMR (CDCl$_3$): 1.25 (s, 6H), 3.35 (s, 2H), 7.43 (m, 3H), 7.88 (m, 2H).

Step B]: (2S)-1-{[1,1-Dimethyl-2-(5-phenyl-[1,3,4] oxadiazol-2-ylamino)-ethylamino]-acetyl}-pyrrolidine-2-carbonitrile, methanesulfonic acid salt The title compound was obtained from 2-methyl-N$^2$-(5-phenyl-[1,3,4]oxadiazole-2-yl)-propane-1,2-diamine (403 mg) and IIA (200 mg), following the procedure outlined in example 1, whereas calcium hydroxide (86 mg) was added and DMF used as solvent. The residue obtained by flash chromatography was dissolved in ethyl acetate and precipitated by treatment with methanesulfonic acid yielding 229 mg of a white powder.

MS (ISP): 369.4 (MH$^+$).

$^1$H-NMR (DMSO-d$_6$): 1.18 (s, 6H), 1.99–2.13 (m, 2H), 2.15–2.23 (m, 2H), 2.31 (s, 3H), 3.54–3.58 (m, 3H), 3.68–3.75 (m, 1H), 4.06–4.18 (m, 2H), 4.85 (dd, 1H), 7.55 (m, 3H), 7.84 (m, 2H), 8.12 (t, 1H), 8.83 (broad s, 1H), 8.95 (broad s, 1H). (+Rotamer)

Example 172

(2S)-1-{[1,1-Dimethyl-2-(3-pyridin-3-yl-[1,2,4]oxadiazol-5-ylamino)-ethylamino]-acetyl}-pyrrolidine-2-carbonitrile, methanesulfonic acid salt

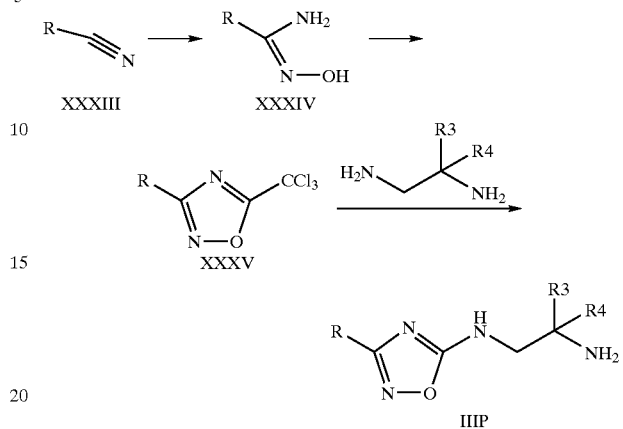

Synthesis of this compound requires the preparation of the corresponding amine precursor IIIP. A possible way for the preparation of IIIP is described in the general scheme above. According to this scheme a carboxylic acid nitril XXXIII is converted to the corresponding hydroxy-amidine XXXIV. Cyclisation in the presence of trichloracetic anhydride and trichloracetic acid provides the [1,2,4]oxadiazole XXXV which is treated with the appropriate 1,2-diaminoethane.

Step A]: N-Hydroxy-nicotinamidine

3-Cyanopyridine (4.0 g) and hydroxylamine hydrochloride (3.2 g) were added to a solution of sodium (1.8 g) in MeOH (60 ml). The mixture was stirred 2.5 h at RT and refluxed 30 min. After cooling to RT, solids were filtered off. The solution was evaporated. White crystals (4.7 g) were obtained upon flash chromatography (125 g silica gel; CH$_2$Cl$_2$/MeOH 9:1) followed by a precipitation from heptan and ethyl acetate.

MS (ISP): 138.2 (MH$^+$).

$^1$H-NMR (DMSO-d$_6$): 5.98 (broad s, 2H), 7.41 (dd, 1H), 8.01 (ddd, 1H), 8.56 (dd, 1H), 8.86 (dd, 1H), 9.84 (s, 1H).

Step B]: 3-(5-Trichloromethyl-[1,2,4]oxadiazol-3-yl)-pyridine, trichloroacetic acid salt A mixture of N-hydroxy-nicotinamidine (3.2 g) trichloroacetic acid (15.2 g) and trichloroacetic anhydride (8.5 ml) was stirred 30 min at 115° C. After cooling to RT, H$_2$O was added. The mixture extracted with ethyl acetate. The organic layers were combined, dried (MgSO$_4$) and evaporated. Flash chromatography (150 g silica gel; cyclohexane/ethyl acetate 4:1) followed by crystallization from heptane provided 8.7 g of white crystals. MS(EI): 264.9 (M$^+$).

$^1$H-NMR (DMSO-d$_6$): 7.66 (dd, 1H), 8.40 (m, 1H), 8.83 (dd, 1H), 9.19 (dd, 1H), 1.19 (dd, 1H).

Step C]: 2-Methyl-N'-(3-pyridin-3-yl-[1,2,4]oxadiazol-5-yl)-propane-1,2-diamine

A solution of 3-(5-trichloromethyl-[1,2,4]oxadiazol-3-yl)-pyridine, trichloroacetic acid salt (2.0 g) and 1,2-diamino-2-methlypropane (2.4 ml) in THF (20 ml) was refluxed 2 h. After cooling to RT, 1 N NaOH was added. The mixture was extracted with ethyl acetate. The organic layers were combined, dried (MgSO$_4$) and evaporated. Crystallisation from diethyl ether provided 0.86 g of white crystals.

MS (ISP): 234.2 (MH$^+$).

$^1$H-NMR (DMSO-d$_6$): 1.04 (s, 6H), 3.22 (s, 2H), 3.3 (broad s, 1H), 7.55 (dd, 1H), 8.23 (ddd, 1H), 8.72 (dd, 1H), 9.05 (d, 1H).

Step D]: (2S)-1-{[1,1-Dimethyl-2-(3-pyridin-3-yl-[1,2,4]oxadiazol-5-ylamino)-ethylamino]-acetyl}-pyrrolidine-2-carbonitrile, methanesulfonic acid salt The title compound was obtained from 2-methyl-N$^1$-(3-pyridin-3-yl-[1,2,4]oxadiazol-5-yl)-propane-1,2-diamine (304 mg) and IIA (105 mg), following the procedure outlined in example 1, whereas calcium hydroxide (64 mg) was added and DMF used as solvent. The residue obtained by flash chromatography was dissolved in ethyl acetate and precipitated by treatment with methanesulfonic acid yielding 240 mg of a white powder.

MS (ISP): 370.3 (MH$^+$).

$^1$H-NMR (DMSO-d$_6$): 1.35 (s, 6H), 1.99–2.10 (m, 2H), 2.12–2.25 (m, 2H), 2.32 (m, 1H), 3.65 (m, 2H), 3.72 (m, 1H), 4.16 (m, 2H), 4.78 (dd, 1H), 7.61 (dd, 1), 8.28 (ddd, 1H), 8.77 (dd, 1H), 8.83 (m, 1H), 8.87 (t, 1H), 8.98 (m, 1H), 9.05 (d, 1H). (+Rotamer)

Example 173

(2S)-1-{[1,1-Dimethyl-2-(3-phenyl-[1,2,4]oxadiazol-5-ylamino)-ethylamino]-acetyl}-pyrrolidine-2-carbonitrile, methanesulfonic acid salt This compound was obtained in analogy to example 172, steps B] to D] starting from N-hydroxy-benzamidine, 1,2-diamino-2-methlypropane and IIA. The residue obtained by flash chromatography was dissolved in ethyl acetate and precipitated by treatment with methanesulfonic acid yielding a white powder.

MS (ISP): 369.4 (MH+).

Example 174

(2S)-1-{[1,1-Dimethyl-2-(3-pyridin-2-yl-[1,2,4]oxadiazol-5-ylamino)-ethylamino]-acetyl}-pyrrolidine-2-carbonitrile, methanesulfonic acid salt This compound was obtained in analogy to example 172, steps A] to D] starting from 2-cyanopyrdine, 1,2-diamino-2-methlypropane and IIA. The residue obtained by flash chromatography was dissolved in ethyl acetate and precipitated by treatment with methanesulfonic acid yielding a white powder.

MS (ISP): 370.4 (MH$^+$).

Example 175

(2S)-1-{[1,1-Dimethyl-2-(3-pyridin-4-yl-1,2,4]oxadiazol-5-ylamino)-ethylamino]-pyrrolidine-2-carbonitrile, methanesulfonic acid salt This compound was obtained in analogy to example 172, steps A] to D] starting from 4-cyanopyrdine, 1,2-diamino-2-methlypropane and IIA. The residue obtained by flash chromatography was dissolved in ethyl acetate and precipitated by treatment with methanesulfonic acid yielding a white powder.

MS (ISP): 370.4 (MH$^+$).

Example 176

(2S)-1-({1,1-Dimethyl-2-[3-(6-methyl-pyridin-3-yl)-[1,2,4]oxadiazol-5-ylamino)-ethylamino}-acetyl)-pyrrolidine-2-carbonitrile, methanesulfonic acid salt This compound was obtained in analogy to example 172, steps A] to D] starting from 5-cyano-2-picoline, 1,2-diamino-2-methlypropane and IIA. The residue obtained by flash chromatography was dissolved in ethyl acetate and precipitated by treatment with methanesulfonic acid yielding a white powder.

MS (ISP): 384.4 (MH$^+$).

Example 177

(2S)-1-({2-[3-(2-Chloro-pyridin-4-yl)-[1,2,4]oxadiazol-5-ylamino]-1,1-dimethyl-ethylamino}-acetyl)-pyrrolidine-2-carbonitrile, methanesulfonic acid salt This compound was obtained in analogy to example 172, steps A] to D] starting from 2-chloro-4-cyanopyridine, 1,2-diamino-2-methlypropane and IIA. The residue obtained by flash chromatography was dissolved in ethyl acetate and precipitated by treatment with methanesulfonic acid yielding a white powder.

MS (ISP): 404.5 (MH$^+$).

Example 178

(2S)-1-({2-[3-(3,5-Dichloro-phenyl)-[1,2,4]oxadiazol-5-ylamino]-1,1-dimethyl-ethylamino}-acetyl)-pyrrolidine-2-carbonitrile, methanesulfonic acid salt This compound was obtained in analogy to example 172, steps A] to D] starting from 3,5-dichlorobenzonitrile, 1,2-diamino-2-methlypropane and IIA. The residue obtained by flash chromatography was dissolved in ethyl acetate and precipitated by treatment with methanesulfonic acid yielding a yellow powder.

MS (ISP): 437.3 (MH$^+$).

Example 179

(2S)-1-{[3-(2-Phenyl-1H-imidazol-4-yl)-propylamino]-acetyl}-pyrrolidine-2-carbonitrile

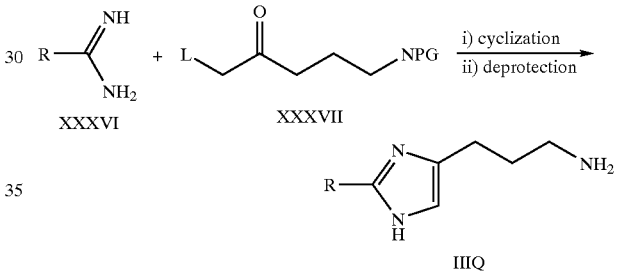

L = leaving group
PG = Protecting group

Synthesis of this compound required the preparation of an amine derivative IIIQ as outlined in the scheme above. Amines IIIQ are synthetically accessible by cyclization of an amidine derivative XXXVI with an N-protected 4-oxo-pentylamine derivative XXXVI activated at the primary 5-position. A suitable N-protecting group is for example the phthalimido group that can be cleaved by treatment with hydrazine. Amidines XXXVI are known in the literature or can be readily prepared from the corresponding nitrile derivatives employing standard methodologies as e.g. the Pinner reaction. Preparations of N-protected 4-oxo-pentylamines XXXVII are described for example in Schunack, W. et al. Z. Naturforschung 1987, 42B, 238–242.

Step A]: 2-[3-(2-Phenyl-1H-imidazol-4-yl)-propyl]-isoindole-1,3-dione

To a solution of 2-(5-bromo-4-oxo-pentyl)-isoindole-1,3-dione [CAS 41306-64-3](12.4 g) in abs. DMF (50 ml) was added benzamidine 85% (5.65 g) and potassium carbonate (11.05 g). The reaction mixture was stirred at 80° C. for 4 h, concentrated under high vacuum, quenched with water and extracted with ethyl acetate. The organic phase was washed with ice/water and brine, dried over magnesium sulphate and concentrated. The residue was purified by chromatography on silica gel using methylene chloride/methanol 2 and 5% as eluent. The product fractions were combined and evaporated to dryness to obtain 2-[3-(2-phenyl-1H- imidazol-4-yl)-propyl]-isoindole-1,3-dione (8.95 g) as a light yellow foam.

MS (ISP): 332.0 (MH$^+$).

Step B]: 3-(2-Phenyl-1H-imidazol-4-yl)-propylamine

To a solution of 2-[3-(2-phenyl-1H-imidazol-4-yl)-propyl]-isoindole-1,3-dione (4.16 g) in ethanol (50 ml) was added hydrazine hydrate (3.18 g). The reaction mixture was stirred under reflux for 4 h, cooled down to 0–5° C., and the precipitate was filtered off. The filtrate was concentrated, and the oily residue was quenched with cooled 1 N NaOH solution (20 ml) and extracted with ethyl acetate. The organic phase was washed with brine, dried over magnesium sulphate and concentrated to dryness to obtain 3-(2-phenyl-1H-imidazol-4-yl)-propylamine (1.95 g) as a yellow foam, which was sufficiently pure to be used directly in the next step.

MS (ISP): 202.2 (MH$^+$).

Step C]: (2S)-1-{[3-(2-Phenyl-1H-imidazol-4-yl)-propylamino]-acetyl}-pyrrolidine-2-carbonitrile To a solution of 3-(2-phenyl-1H-imidazol-4-yl)-propylamine (0.603 g) in abs. THF (40 ml) was added IIA (0.172 g) in analogy to example 1. The reaction mixture was stirred at RT for 20 h, concentrated under vacuum. The residue was purified by chromatography on silica gel using methylene chloride/methanol 10, 20 and 30% as eluent. The compound containing fractions were combined and evaporated to dryness to obtain the title compound (0.175 g) as a light yellow foam.

MS (ISP): 338.2 (MH$^+$).

Example 180

(2S)-1-{[(5-Methyl-2-phenyl-1H-imidazol-4-ylmethyl)-amino]-acetyl}-pyrrolidine-2-carbonitrile

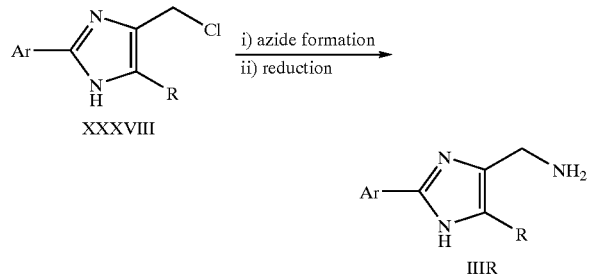

Synthesis of this compound required the preparation of an amine of type IIIR which is accessible from imidazoles XXXVIII via azide formation and reduction. Azide derivatives can be obtained by substitution reactions of XXXVIII with azides using e.g. metal azides or a Mitsunobu protocol. Reduction of azides is well known in literature to be accomplished by e.g. hydrogenation or Staudinger reaction. Imidazoles XXXVIII are commercially available or can be prepared in analogy to the procedures described in WO 96/10018.

Step A]: 4-Azidomethyl-5-methyl-2-phenyl-1H-imidazole

To a solution of 4-chloromethyl-5-methyl-2-phenyl-1H-imidazole hydrochloride (4.86 g) [CAS 58731-95-6] in DMF (50 ml) was added sodium azide (7.79 g). The reaction mixture was stirred at room temperature for 18 h under argon and concentrated without heating under high vacuum. To the residue was added ice/1 molar K$_2$CO$_3$ solution, and the mixture was extracted with ethyl acetate. The organic phase was washed with brine, dried over magnesium sulphate and concentrated. The residue was purified by chromatography on silica gel using methylene chloride/methanol 2% as eluent to obtain 4-azidomethyl-5-methyl-2-phenyl-1H-imidazole (3.70 g) as a light yellow amorphous powder.

MS (ISP): 214.3 (MH$^+$). Step B]: C-(5-Methyl-2-phenyl-1H-imidazol-4-yl)-methylamine To solution of 4-azidomethyl-5-methyl-2-phenyl-1H-imidazole (1.22 g) in ethanol (50 ml) was added 10% Pd/C (0.10 g). The reaction mixture was hydrogenated at room temperature and 1.1 bar for 30 minutes, the catalyst was filtered off over a pad of celite. The filtrate was evaporated to dryness under high vacuum to obtain C-(5-methyl-2-phenyl-1H-imidazol-4-yl)-methylamine (1.06 g) as a light yellow foam which was sufficiently pure to be used directly in the next step.

MS (ISP): 188.4 (MH$^+$).

Step C]:(2S)-1-{[(5-Methyl-2-phenyl-1H-imidazol-4-ylmethyl)-amino]-acetyl}-pyrrolidine-2-carbonitrile To a solution of C-(5-methyl-2-phenyl-1H-imidazol-4-yl)-methylamine (1.12 g) in abs. THF (60 ml) was added IIA (0.345 g) in analogy to example 1. The reaction mixture was stirred at room temperature for 20 h, concentrated under vacuum. The residue was quenched with brine and conc. NaOH solution/ice and extracted with ethyl acetate. The organic phase was washed with brine, dried over magnesium sulphate and concentrated, the residue was purified by chromatography on silica gel using methylene chloride/methanol 5% and 10% as eluent to obtain the title compound (0.32 g) as a light yellow foam.

MS (ISP): 324.3 (MH$^+$).

Example 181

(2S)-1-{[2-(5-Methyl-2-phenyl-1H-imidazol-4-yl)-ethylamino]-acetyl}-pyrrolidine-2-carbonitrile

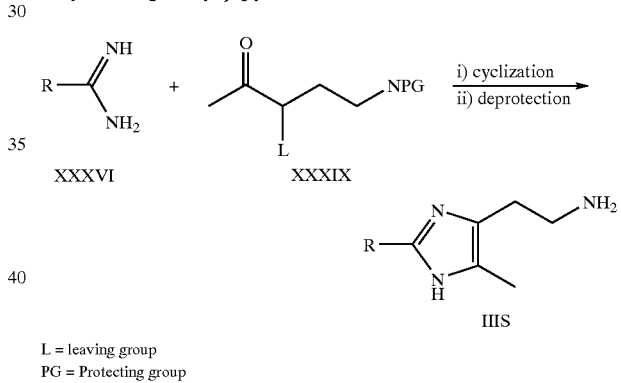

L = leaving group
PG = Protecting group

Synthesis of this compound required the preparation of an amine derivative IIIS. This could be achieved as outlined in the scheme above by cyclization of an amidine derivative XXXVI with an N-protected 4-oxo-pentylamine XXXIX activated at the 3-position. A suitable N-protecting group is for example the phthalimido group that can be cleaved by treatment with hydrazine. Aryl amidines XXXVI are known in the literature or can be readily prepared from the corresponding nitrile derivatives employing standard methodologies as e.g. the Pinner reaction. Preparations of N-protected 4-oxo-pentylamines XXXIX are described in Schunack, W. et al. Z. Naturforschung 1987, 42B, 238–242.

Step A]: 2-[2-(5-Methyl-2-phenyl-1H-imidazol-4-yl)-ethyl]-isoindole-1,3-dione

To a solution of 2-(3-bromo-4-oxo-pentyl)-isoindole-1,3-dione (12.4 g) [CAS 112357-34-3] in abs. DMF (50 ml) was added benzamidine 85% (5.65 g) and potassium carbonate (11.03 g). The reaction mixture was stirred at 80° C. for 4 h, concentrated under vacuum. To the residue was added ice/water, and the mixture was extracted with ethyl acetate. The organic phase was washed with water and brine, dried over magnesium sulphate and concentrated. The crude product was purified by chromatography on silica gel using methylene chloride/methanol 5% and 10% as eluent to obtain 2-[2-(5-methyl-2-phenyl-1H-imidazol-4-yl)-ethyl]-isoindole-1,3-dione (5.5 g) as a yellow foam.

MS (ISP): 332.3 (MH+).

Step B]: 2-(5-Methyl-2-phenyl-1H-imidazol-4-yl)-ethylamine

To a solution of 2-[2-(5-methyl-2-phenyl-1H-imidazol-4-yl)-ethyl]-isoindole-1,3-dione (5.3 g) in ethanol (80 ml) was added hydrazine hydrate (4.0 g). The reaction mixture was stirred under reflux for 4 h, cooled to 0° C., and the precipitate was filtered off. To the filtrate was added brine and cold 2 N NaOH (20 ml), and the mixture was extracted with ethyl acetate. The organic phase was washed with brine, dried over magnesium sulphate and evaporated to dryness in high vacuum to obtain 2-(5-methyl-2-phenyl-1H-imidazol-4-yl)-ethylamine (3.8 g) as an off-white solid, which was sufficiently pure to be used directly in the next step.

MS (ISP): 202.2 (MH+).

Step C]:(2S)-1-{[2-(5-Methyl-2-phenyl-1H-imidazol-4-yl)-ethylamino]-acetyl}-pyrrolidine-2-carbonitrile To a solution of 2-(5-methyl-2-phenyl-1H-imidazol-4-yl)-ethylamine (1.21 g) in abs THF (60 ml) was added IIA (0.345 g) in analogy to example 1. The reaction mixture was stirred at room temperature for 20 h and concentrated under vacuum. The residue was taken up in a small amount of methylene chloride/methanol and purified by chromatography on silica gel using methylene chloride/methanol 10%, 20% and 30% as eluent to obtain the title compound (0.465 g) as a light yellow foam.

MS (ISP): 338.2 (MH+).

Example 182
(2S)-1-{[2-(5-Methyl-2-pyridin-4-yl-1H-imidazol-4-yl)-ethylamino]-acetyl}-pyrrolidine-2-carbonitrile The title compound was obtained as described in example 181, steps A] to C], starting from 2-(3-bromo-4-oxo-pentyl)-isoindole-1,3-dione [CAS 112357-34-3] and 4-amidinopyridine hydrochloride [CAS 6345-27-3] After chromatography, the product was obtained as a light yellow semisolid

MS (ISP): 339.2 (MH+).

Example 183
(2S)-1-{[2-(5-Methyl-2-pyridin-3-yl-1H-imidazol-4-yl)-ethylamino]-acetyl}-pyrrolidine-2-carbonitrile The title compound was obtained as described in example 181, steps A] to C], starting from 2-(3-bromo-4-oxo-pentyl)-isoindole-1,3-dione [CAS 112357-34-3] and 3-amidinopyridine hydrochloride [CAS 7356-60-7]. After chromatography, the desired product was obtained as a yellow semisolid

MS (ISP): 339.3 (MH+).

Example 184
(2S)-1-{[2-(5-Methyl-2-pyridin-2-yl-1H-imidazol-4-yl)-ethylamino]-acetyl}-pyrrolidine-2-carbonitrile The title compound was obtained as described in example 181, steps A] to C], starting from 2-(3-bromo-4-oxo-pentyl)-isoindole-1,3-dione [CAS 112357-34-3] and 2-amidinopyridine hydrochloride [CAS 51285-26-8]. After chromatography, the desired product was obtained as a yellow foam

MS (ISP): 339.2 (MH+).

Example 185
(2S)-1-{[2-(2-Phenyl-1H-imidazol-4-yl)-ethylamino]-acetyl}-pyrrolidine-2-carbonitrile To a solution of 2-(2-phenyl-1H-imidazol-4-yl)-ethylamine (1.12 g) [CAS 57118-68-0] in DMF (10 ml) was added IIA (0.518 g) and calcium hydroxide (0.223 g) in analogy to example 1. The reaction mixture was stirred at room temperature for 18 h and concentrated under high vacuum. The residue was quenched with ice/conc. NaOH solution/brine and extracted with ethyl acetate. The organic phase was washed with brine, dried over magnesium sulphate and concentrated. The residue was purified by chromatography on silica gel using methylene chloride/methanol 5 and 10% as eluent to obtain the title compound (0.50 g) as a light yellow foam.

MS (ISP): 324.3 (MH+).

Example 186
(2S)-1-({2-[2-(3-Fluoro-4-methyl-phenyl)-5-methyl-1H-imidazol-4-yl]-1,1-dimethyl-ethylamino-}-acetyl)-pyrrolidine-2-carbonitrile

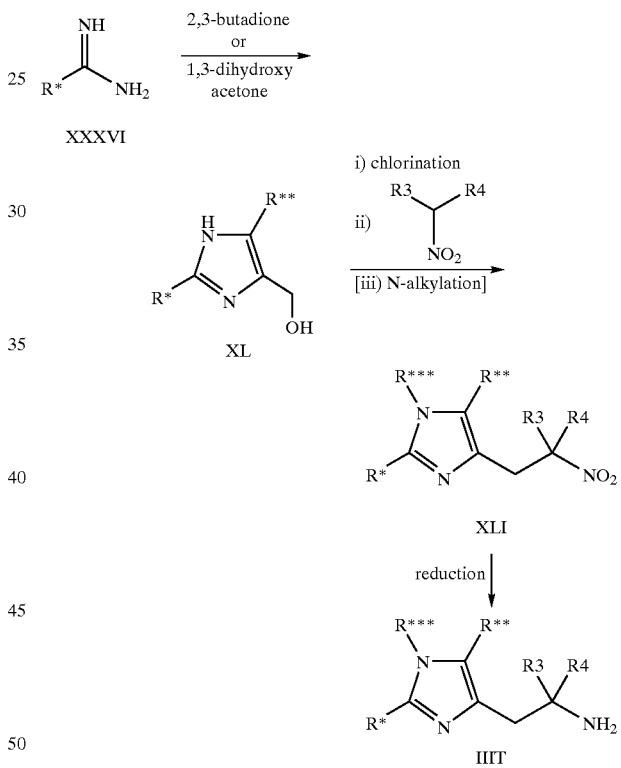

Synthesis of the title compound required the preparation of the corresponding amine precursor IIIT. A possible synthetic sequence is described in the general scheme above. Imidazoles XL could be prepared from amidines XXXVI by reaction with 2,3-butadione or 1,3-dihydroxyacetone as described in WO 96/10018 or in DE2528640. Chlorination and reaction with aliphatic nitro compounds under basic conditions (as for example described in *Eur. J. Med. Chem.* 1995, 30, 219–225) yielded the nitro derivatives XLI. Prior to the final reduction to the amine derivatives IIIT an N-alkylation step is optionally.

Step A]: [2-(3-Fluoro-4-methyl-phenyl)-5-methyl-1H-imidazol-4-yl]-methanol, hydrochloride To a solution of 3-fluoro-4-methylbenzamidine hydrochloride (5.65 g) [CAS 175277-88-0] in isopropanol (75 ml)

was added at 80° C. 2,3-butanedione (3.22 g) [CAS 431-03-8, commercially available]. After the reaction mixture had been stirred under reflux for 48 h, it was concentrated and the resulting residue was taken up in 3 molar HCl (80 ml) and refluxed again for 3 h. Then the reaction mixture was concentrated almost to dryness. To the remaining residue acetone (100 ml) was added and the mixture was cooled to 0° C. The precipitate formed was filtered, washed with a small amount of cold acetone and ether and dried under high vacuum to obtain 2-(3-fluoro-4-methyl-phenyl)-5-methyl-1H-imidazol-4-yl]-methanol hydrochloride (6.7 g) as an off-white solid.

MS (ISP): 221.2 (MH$^+$).

Step B]:2-(3-Fluoro-4-methyl-phenyl)-5-methyl-4-(2-methyl-2-nitro-propyl)-1H-imidazole To a suspension of 2-(3-fluoro-4-methyl-phenyl)-5-methyl-1H-imidazol-4-yl]-methanol hydrochloride (4.87 g) in toluene (45 ml) was added dropwise in 15 minutes at 45° C. thionyl chloride (14.1 g) dissolved in toluene (5 ml). The reaction mixture was stirred half an hour at 65° C. and 2 h at RT, ether (200 ml) was added, the precipitate filtered off and dried. The crude dry residue (5.12 g) was dissolved in methanol (25 ml) and added dropwise within 15 minutes at 20–25° C. to a mixture of 2-nitropropane (5.4 g) and 1 molar sodium methylate/methanol (46 ml). The reaction mixture was stirred at RT for 3 h, concentrated under vacuum without heating, the residue quenched with ice/brine and extracted with ethyl acetate. The organic phase was washed with brine, dried over magnesium sulphate and concentrated. The residue was triturated with methylene chloride/ether, cooled down and the solid filtrated. The filter cake was washed with ether and dried to obtain 2-(3-fluoro-4-methyl-phenyl)-5-methyl-4-(2-methyl-2-nitro-propyl)-1H-imidazole (4.2 g) as a off-white solid.

MS (ISP): 292.3 (MH$^+$).

Step C]:2-[2-(3-Fluoro-4-methyl-phenyl)-5-methyl-1H-imidazol-4-yl]-1,1-dimethyl-ethylamine To a solution of 2-(3-fluoro-4-methyl-phenyl)-5-methyl-4-(2-methyl-2-nitro-propyl)-1H-imidazole (1.6 g) in acetic acid (32 ml) was added in 2 equal portions of Zn dust (5.2 g) in 15 minutes at 20–25° C. The slightly exothermic reaction was stirred at RT for 1.5 h, the inorganic salts filtered off, and washed with acetic acid. The filtrate was concentrated almost to dryness, the residue quenched with cold conc. NaOH and brine, and extracted with ethyl acetate. The organic phase was washed with brine, dried over magnesium sulphate and evaporated to dryness to obtain 2-[2-(3-fluoro-4-methyl-phenyl)-5-methyl-1H-imidazol-4-yl]-1,1-dimethyl-ethylamine (1.16 g) as a light yellow foam, pure enough to be used in the next step.

MS (ISP): 262.3 (MH$^+$).

Step D]:(2S)-1-({2-[2-(3-Fluoro-4-methyl-phenyl)-5-methyl-1H-imidazol-4-yl]-1,1-dimethyl-ethylamino}-acetyl)-pyrrolidine-2-carbonitrile To a solution of 2-[2-(3-fluoro-4-methyl-phenyl)-5-methyl-1H-imidazol-4-yl]-1,1-dimethyl-ethylamine (0.522 g) in DMF (15 ml) was added IIA (0.172 g) in analogy to example 1. The reaction mixture was stirred at RT for 20 h, concentrated under vacuum. The residue was purified by chromatography on silica gel using methylene chloride/methanol 5 and 10% as eluent. The compound containing fractions were evaporated to dryness to obtain the title compound as light yellow foam (0.331 g)

MS (ISP): (MH$^+$).

Example 187

(2S)-1-({1,1-Dimethyl-2-[5-methyl-2-(4-trifluoromethyl-phenyl)-1H-imidazol-4-yl]-ethylamino}-acetyl)-pyrrolidine-2-carbonitrile The title compound was obtained in analogy to example 186, Steps A] to D] starting from 4-(trifluoromethyl) benzamidine hydrochloride dihydrate [CAS 175278-62-3] and 2,3-diketobutane [CAS 431-03-8]. After chromatography on silica gel using methylene chloride/methanol as eluent, the desired product was obtained as a colorless foam.

MS (ISP): 434.3 (MH$^+$).

Example 188

(2S)-1-{[1,1-Dimethyl-2-(5-methyl-2-m-tolyl-1H-imidazol-4-yl)-ethylamino]-acetyl}-pyrrolidine-2-carbonitrile.

The title compound was obtained in analogy to example 186, Steps A] to D] starting from 3-methylbenzenecarboximidamide hydrochloride [CAS 20680-59-5] and 2,3-butanedione [CAS 431.03-8]. After chromatography on silica gel using methylene chloride/methanol as eluent, the desired product was obtained as a colorless foam.

MS (ISP): 380.3 (MH$^+$).

Example 189

(2S)-1-({1,1-Dimethyl-2-[5-methyl-2-(3-chlorophenyl)-1H-imidazol-4-yl]-ethylamino-}-acetyl)-pyrrolidine-2-carbonitrile.

The title compound was obtained in analogy to example 186, Steps A] to D] starting from 3-chlorobenzenecarboximidamide hydrochloride [CAS 24095-60-1] and 2,3-butanedione [CAS 431.03-8]. After chromatography on silica gel using methylene chloride/methanol as eluent, the desired product was obtained as a colorless foam.

MS (ISP): 400.4 (MH$^+$).

Example 190

(2S)-1-({2-[2-(3,5-Bis-trifluoromethyl-phenyl)-5-methyl-1H-imidazol-4-yl]-1,1-dimethyl-ethylamino}-acetyl)-pyrrolidine-2-carbonitrile The title compound was obtained in analogy to example 186, Steps A] to D] starting from 3,5-bis-(trifluoromethyl) benzamidine hydrochloride [CAS 97603-94-6] and 2,3-butanedione [CAS 431.03-8]. After chromatography on silica gel using methylene chloride/methanol as eluent, the desired product was obtained as a colorless foam.

MS (ISP): 502.3 (MH$^+$).

Example 191

(2S)-1-({2-[2-(3,5-Dichloro-phenyl)-5-methyl-1H-imidazol-4-yl]-1,1-dimethyl-ethylamino}-acetyl)-pyrrolidine-2-carbonitrile The title compound was obtained in analogy to example 186, Steps A] to D] starting from 3,5-dichlorobenzamidine hydrochloride [CAS 22978-61-6] and 2,3-butanedione [CAS 431.03-8]. After chromatography on silica gel using methylene chloride/methanol as eluent, the desired product was obtained as a colorless foam.

MS (ISP): 434.2, 436.2 (MH$^+$).

Example 192

(2S)-1-{[1,1-Dimethyl-2-(2-phenyl-1H-imidazol-4-yl)-ethylamino]-acetyl}-pyrrolidine-2-carbonitrile The title compound was obtained in analogy to example 186, Steps B] to D] starting from (2-phenyl-1H-imidazol-4-yl)-methanol [CAS 43002-54-6]]. After chromatography on silica gel using methylene chloride/methanol as eluent, the desired product was obtained as a light yellow foam.

MS (ISP): 352.3 (MH$^+$).

Example 193

(2S)-1-{[1,1-Dimethyl-2-(1-methyl-2-phenyl-1H-imidazol-4-yl)-ethylamino]-acetyl}-pyrrolidine-2-carbonitrile The title compound was obtained in analogy to example 186, steps B] to D] starting from (2-phenyl-1H-imidazol-4-yl)-methanol [CAS 43002-54-6]. Additionally an N-alkylation step B-1] was performed after step B]. This alkylation could be done in analogy to the method described in *J. Med. Chem.* 1986, 29, 261–267. After chromatography on silica gel using methylene chloride/methanol as eluent, the title compound was obtained as a light yellow foam.

MS (ISP): 366.3 (MH$^+$).

Step B-1]: 1-Methyl-4-(2-methyl-2-nitro-propyl)-2-phenyl-1H-imidazole

Methyliodide (1.4 g) was added dropwise to a mixture of 4-(2-methyl-2-nitro-propyl)-2-phenyl-1H-imidazole (1.6 g) and fine powdered potassium hydroxide (2.19 g) in DMF (20 ml) at 20–25° C. The reaction mixture was stirred at RT for 4 h, quenched with ice/water and extracted with ethyl acetate. The organic phase was washed with water and brine, dried over magnesium sulphate and concentrated. The residue was purified on silica gel using methylene chloride/methanol 2 and 5% as eluent to obtain the desired product (1.40 g) as a light yellow solid.

Example 194

(2S)-1-{[2-(1,5-Dimethyl-2-phenyl-1H-imidazol-4-yl)-1,1-dimethyl-ethylamino]-acetyl}-pyrrolidine-2-carbonitrile The title compound was obtained in analogy to example 186, steps B] to D] starting from (5-methyl-2-phenyl-1H-imidazol-4-yl)-methanol hydrochloride [CAS 32330-02-2]. Additionally an N-alkylation step B-1] was performed after step B]. This alkylation could be done in analogy to the method described in *J. Med. Chem.* 1986, 29, 261–267. After chromatography on silica gel using methylene chloride/methanol as eluent, the desired product was obtained as a colorless foam.

MS (ISP): 380.3 (MH$^+$)

Step B-1]: 1,5-Dimethyl-4-(2-methyl-2-nitro-propyl)-2-phenyl-1H-imidazole

Methyliodide (1.4 g) was added dropwise to a stirred mixture of 5-methyl-4-(2-methyl-2-nitro-propyl)-2-phenyl-1H-imidazole (2.0 g) and fine powdered potassium hydroxide (2.0 g) in DMF (30 ml) at 10–20° C. The reaction mixture was stirred at RT for 2 h, quenched with ice/water and extracted with ethyl acetate. The organic phase was washed with water and brine, dried over magnesium sulphate and concentrated. The residue was purified on silica gel using methylene chloride/methanol 2 and 5% as eluent to obtain the desired product (0.98 g) as a light yellow amorphous compound.

MS (ISP): 274.2(MH$^+$).

Example 195

(2S)-1-({2-[2-(3-fluoro-phenyl)-5-methyl-1H-imidazol-4-yl]-1,1-dimethyl-ethylamino}-acetyl)-pyrrolidine-2-carbonitrile The title compound was obtained in analogy to example 186, steps A] to D], starting from 3-fluorobenzamidine hydrochloride [CAS 75207-72-6] and 2,3-diketobutane [CAS 431-03-8]. After chromatography on silica gel using methylene chloride/methanol as eluent, the desired product was obtained as a colorless foam.

MS (ISP): 384.4 (MH$^+$).

Example 196

(2S)-1-({2-[2-(3-Methoxy-phenyl)-5-methyl-1H-imidazol-4-yl]-1,1-dimethyl-ethylamino}-acetyl)-pyrrolidine-2-carbonitrile The title compound was obtained in analogy to example 186, steps A] to D], starting from 3-methoxy benzamidine hydrochloride [CAS 26113-44-0] and 2,3-diketobutane [CAS 431-03-8]. After chromatography on silica gel using methylene chloride/methanol as eluent, the desired product was obtained as a colorless foam.

MS (ISP): 396.4 (MH$^+$).

Example 197

(2S)-1-({2-[2-(3-Ethoxy-phenyl)-5-methyl-1H-imidazol-4-yl]-1,1-dimethyl-ethylamino}-acetyl)-pyrrolidine-2-carbonitrile The title compound was obtained in analogy to example 186, steps A] to D], starting from 3-ethoxybenzamidine hydrochloride [CAS 25027-74-1] and 2,3-diketobutane [CAS 431-03-8]. After chromatography on silica gel using methylene chloride/methanol as eluent, the desired product was obtained as a colorless foam.

MS (ISP): 410.4 (MH$^+$).

Example 198

(2S)-1-({2-[2-(3,5-Difluoro-phenyl)-5-methyl-1H-imidazol-4-yl]-1,1-dimethyl-ethylamino}-acetyl)-pyrrolidine-2-carbonitrile The title compound was obtained in analogy to example 186, steps A] to D], starting from 3,5-difluoro benzamidine hydrochloride [CAS 144797-68-2] and 2,3-diketobutane [CAS 431-03-8]. After chromatography on silica gel using methylene chloride/methanol as eluent, the desired product was obtained as a colorless foam.

MS (ISP): 402.3 (MH$^+$).

Example 199

(2S)-1-({2-[2-(3,5-Dimethoxy-phenyl)-5-methyl-1H-imidazol-4-yl]-1,1-dimethyl-ethylamino}-acetyl)-pyrrolidine-2-carbonitrile The title compound was obtained in analogy to example 186, steps A] to D], starting from 3,5-dimethoxy benzamidine hydrochloride [CAS 61416-81-7] and 2,3-diketobutane [CAS 431-03-8]. After chromatography on silica gel using methylene chloride/methanol as eluent, the desired product was obtained as a colorless foam.

MS (ISP): 426.4 (MH$^+$).

Example 200

(2S)-1-({1,1-Dimethyl-2-[5-methyl-2-(3-trifluoromethyl-phenyl)-1H-imidazol-4-yl]-ethylamino}-acetyl)-pyrrolidine-2-carbonitrile The title compound was obtained in analogy to example 186, steps A] to D], starting from 3-(trifluoromethyl) benzamidine hydrochloride [CAS 62980-03-4] and 2,3-diketobutane [CAS 431-03-8]. After chromatography on silica gel using methylene chloride/methanol as eluent, the desired product was obtained as a colorless foam.

MS (ISP): 434.3 (MH$^+$).

Example 201

(2S)-1-{[-Dimethyl-2-(5-methyl-2-pyridin-2-yl-1H-imidazol-4-yl)-ethylamino]-acetyl}-pyrrolidine-2-carbonitrile The title compound was obtained in analogy to example 186, steps A] to D], starting from pyridine-2-carboximidamide hydrochloride [CAS 51285-26-8] and 2,3-diketobutane [CAS 431-03-8]. In this case, the nitro to

Example 202
(2S)-1-{[1,-Dimethyl-2-(5-methyl-2-pyridin-3-yl-1H-imidazol-4-yl)-ethylamino]-acetyl}-pyrrolidine-2-carbonitrile The title compound was obtained in analogy to example 186, steps A] to D], starting from pyridine-3-carboximidamide hydrochlorid [CAS 7356-60-7] and 2,3-diketobutane [CAS 431-03-8]. In this case, the nitro to amino group reduction (step C]) was performed with Pd/C and ammonium formate as described in Tetrahedron Lett., 1985, 25,3415–3418. After chromatography on silica gel using methylene chloride/methanol as eluent, the desired product was obtained as a colorless foam.
MS (ISP): 367.3 (MH+).

Example 203
(2S)-1-{[1,1-Dimethyl-2-(5-methyl-2-pyridin-4-1-1H-imidazol-4-yl)-ethlamino]-acetyl}-pyrrolidine-2-carbonitrile The title compound was obtained in analogy to example 186, steps A] to D], starting from pyridine-4-carboximidamide hydrochloride [CAS 6345-27-33] and 2,3-diketobutane [CAS 431-03-8]. In this case, the nitro to amino group reduction (step C]) was performed with Pd/C and ammonium formate as described in Tetrahedron Lett., 1985, 25, 3415–3418. After chromatography on silica gel using methylene chloride/methanol as eluent, the desired product was obtained as a colorless foam.
MS (ISP): 367.3 (MH+).

Example 204
(2S)-1-(1,1-Dimethyl-2-[5-methyl-2-(3-trifluoromethoxyphenyl)-1H-imidazol-4-yl]-ethylamino}-acetyl)-pyrrolidine-2-carbonitrile The title compound was obtained in analogy to example 186, steps A] to D], starting from 3-trifluoromethoxy benzamidine hydrochloride [CAS 62980-03-4] and 2,3-diketobutane [CAS 431-03-8]. After chromatography on silica gel using methylene chloride/methanol as eluent, the desired product was obtained as a colorless foam.
MS (ISP): 449.4 (MH+).

Example 205
(2S)-1-{[1,1-Dimethyl-2-(5-methyl-2-phenyl-1H-imidazol-4-yl)-ethylamino]-acetyl}-pyrrolidine-2-carbonitrile The title compound was obtained in analogy to example 186, steps B] to D], starting from (5-methyl-2-phenyl-1H-imidazol-4-yl)-methanol hydrochloride [CAS 32330-02-2]. After chromatography on silica gel using methylene chloride/methanol as eluent, the desired product was obtained as a colorless foam.
MS (ISP): 366.3 (MH+).

Example 206
(2S)-1-({2-[2-(4-Chloro-phenyl)-5-methyl-1H-imidazol-4-yl]-1,1-dimethyl-ethylamino}-acetyl)-pyrrolidine-2-carbonitrile The title compound was obtained in analogy to example 186, steps B] to D], starting [2-(4-chloro-phenyl)-5-methyl-1H-imidazol-4-yl]-methanol hydrochloride [CAS 14401-51-5]. After chromatography on silica gel using methylene chloride/methanol as eluent, the desired product was obtained as a colorless foam.
MS (ISP): 400.4 (MH+).

Example 207
(2S)-1-{[1,1-Dimethyl-2-(5-methyl-2-p-tolyl-1H-imidazol-4-yl)-ethylamino]-acetyl}-pyrrolidine-2-carbonitrile The title compound was obtained in analogy to example 186, steps B] to D], starting from (5-methyl-2-p-tolyl-1H-imidazol-4-yl)-methanol hydrochloride [CAS 6326-27-8]. After chromatography on silica gel using methylene chloride/methanol as eluent, the desired product was obtained as a colorless foam.
MS (ISP): 380.4 (MH+).

Example 208
(2S)-1-({2-[2-(3-Chloro-4-methyl-phenyl)-5-methyl-1H-imidazol-4-yl]-1,1-dimethyl-ethylamino}-acetyl)-pyrrolidine-2-carbonitrile The title compound was obtained in analogy to example 186, steps B] to D], starting from [2-(3-chloro-4-methyl-phenyl)-5-methyl-1H-imidazol-4-yl]-methanol hydrochloride [CAS 116940-45-5]. After chromatography on silica gel using methylene chloride/methanol as eluent, the desired product was obtained as a colorless foam.
MS (ISP): 414.2 (MH+).

Example 209
(2S)-1-({1,1-Dimethyl-2-[2-(3-acetamidophenyl)-5-methyl-1H-imidazol-4-yl]-ethylamino}-acetyl)-pyrrolidine-2-carbonitrile The title compound was obtained in analogy to example 186, steps A] to D], starting from N-[3-(aminoiminomethyl)phenyl]-acetamide and 2,3-diketobutane [CAS 431-03-8]. The starting material could be prepared from N-(3-cyanophenyl)-acetamide [CAS 58202-84-9] by means of a Pinner reaction as for example described in J. Poupaert et al., Synthesis 1972, 622. After chromatography on silica gel using methylene chloride/methanol as eluent, the desired product was obtained as a colorless foam.
MS (ISP): 423.4 (MH+).

EXAMPLES

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcristalline cellulose and the mixture is granulated with a solution of polyvinylpyrrolidon in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene Glycol 400 | 150.0 mg |
| Acetic Acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by Acetic Acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| | |
|---|---|
| Capsule contents | |
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula (I) | 50.0 mg |
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesiumstearate | 10.0 mg |
| Flavoring additives | 1.0 mg |

The active ingredient is mixed with lactose, microcristalline cellulose and sodium carboxymethyl cellulose and granulated with a mixture of polyvinylpyrrolidon in water. The granulate is mixed with magnesiumstearate and the flavouring additives and filled into sachets.

It should be understood, of course, that the foregoing relates to preferred embodiments of the invention and that modifications may be made without departing from the spirit and scope of the invention as set forth in the following claims.

We claim:

1. A compound of formula (I)

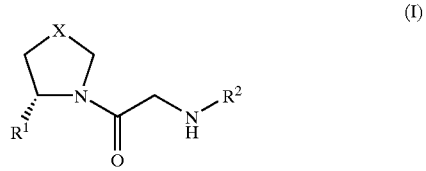

(I)

wherein $R^1$ is CN, $R^2$ is $-C(R^3,R^4)-(CH_2)_n-R^5$, $R^3$ is hydrogen, lower-alkyl, benzyl, or hydroxybenzyl, $R^4$ is hydrogen or lower-alkyl, $R^5$ is oxazolyl or imidazolyl which can be unsubstituted or substituted with 1 to 3 substituents independently selected from the group consisting of lower-alkyl, lower-alkoxy, halogen, CN, $CF_3$, trifluoroacetyl, pyridinyl and phenyl, which pyridinyl can be unsubstituted or substituted with 1 to 3 substituents independently selected from the group consisting of lower-alkyl, lower-alkoxy, hologen, and $CF_3$, and which phenyl can be unsubstituted or substituted with 1 to 3 substituents independently selected from the aroup consisting of lower-alkyl, lower-alkoxy, benzyloxy, halogen, $CF_3$, $CF_3-O$, CN and NH—CO—lower-alkyl, X is $C(R^8,R^9)$, $R^8$ and $R^9$ independently from each other are H or lower-alkyl, n is 0,1 or 2, or a pharmaceutically acceptable salt thereof.

2. A compound according to claim 1, wherein $R^5$ is oxazolyl or imidazolyl which can be unsubstituted or substituted with 1 to 3 substituents independently selected from the group consisting of lower-alkyl, lower-alkoxy, halogen, CN, $CF_3$, trifluoroacetyl, and phenyl which can be unsubstituted or substituted with 1 to 3 substituents independently selected from the group consisting of lower-alkyl, lower-alkoxy, benzyloxy, halogen, $CF_3$, and CN, or a pharmaceutically acceptable salt thereof.

3. A compound according to claim 1, wherein X is —CH$_2$—.

4. A compound according to claim 1, wherein R$^5$ is selected from the group consisting of 5-Methyl-2-phenyl-oxazol-4-yl, 2-(4Fluoro-phenyl)-5-methyl-oxazol-4-yl, 2-(4-Benzyloxy-phenyl)-5-methyl-oxazol-4-yl, 2-(2-Ethoxy-4-fluoro-phenyl)5-methyl-oxazol-4-yl, 2-(4-Chloro-phenyl)-5-methyl-oxazol-4-yl, 2-(3-Methyl-phenyl)-5-methyl-oxazol-4-yl, 2-(3,5-Dimethoxy-phenyl)-5-methyl-oxazol-4-yl, 2-(4-Fluoro-3-methyl-phenyl)-5-methyl-oxazol4-yl, 2-(3-Chloro-phenyl)-5-methyl-oxazol-4-yl, 2-(2-Chloro-phenyl)-5-methyl-oxazol-4-yl, 2-phenyl-oxazol-4-yl, 2-methyl-4-pyridin-3-yl-imidazol-1-yl, 4-phenyl-imidazol-1-yl, 4-pyridin-2-yl-imidazol-1-yl, 4-pyridin-3-yl-imidazol-1-yl, 2-phenyl-1H-imidazol-4-yl, 5-Methyl-2-phenyl-1H-imidazol-4-yl, 5-Methyl-2-pyridin-4-yl-1H-imidazol-4-yl, 5-Methyl-2-pyridin-3-yl-1H-imidazol-4-yl, 5-Methyl-2-pyridin-2-yl-1H-imidazol-4-yl, 2-(3-Fluoro-4-methyl-phenyl)-5-methyl-1H-imidazol-4-yl, 5-methyl-2-(4-trifluoromethyl-phenyl)-1H-imidazol-4-yl, 5-methyl-2-m-tolyl-1H-imidazol-4-yl, 5-methyl-2-(3-chlorophenyl)-1H-imidazol-4-yl, 2-(3,5-Bis-trifluoromethyl-phenyl)-5-methyl-1H-imidazol-4-yl, 2-(3,5-Dichloro-phenyl)-5-methyl-1H-imidazol-4-yl, 1-methyl-2-phenyl-1H-imidazol-4-yl, 1,5-Dimethyl-2-phenyl-1H-imidazol-4-yl, 2-(3-Fluoro-phenyl)-5-methyl-1H-imidazol-4-yl, 2-(3-Methoxy-phenyl)-5-methyl-1H -imidazol-4-yl, 2-(3-Ethoxy-phenyl)-5-methyl-1H-imidazol-4-yl, 2-(3,5-Difluoro-phenyl)-5-methyl-1H-imidazol-4-yl, 2-(3,5-Dimethoxy-phenyl)-5-methyl-1H-imidazol-4-yl, 5-methyl-2-(3-trifluoromethyl-phenyl)-1H-imidazol-4-yl, 5-methyl-2-(3-trifluoromethoxy-phenyl)-1H -imidazol-4-yl, 2-(4-Chloro-phenyl)-5-methyl-1H-imidazol-4-yl, 5-methyl-2-p-tolyl-1H -imidazol-4-yl, 2-(3-Chloro-4-methyl-phenyl)-5-methyl-1H-imidazol-4-yl, and 2-(3-acetamidophenyl)-5-methyl-1H-imidazol-4-yl, and R$^3$ and R$^4$ independently from each other are hydrogen or methyl.

5. A compound according to claim 4, wherein R$^5$ is selected from the group consisting of 2-(4-Fluoro-phenyl)-5-methyl-oxazol-4-yl, 2-(4-Benzyloxy-phenyl)-5-methyl-oxazol-4-yl, 5-methyl-2-phenyl-oxazol-4-yl, 2-methyl-4-pyridin-3-yl-imidazol-1-yl, and 4-pyridin-3-yl-imidazol-1-yl, and R$^3$ and R$^4$ independently from each other are hydrogen or methyl.

6. A compound according to claim 1, selected from the group consisting of (2S)-1-{[2-(5-Methyl-2-pheny-oxazol-4-yl)-ethylamino]-acetyl}-pyrrolidine-2-carbonitrile, (2S)-1-({2-[2-(4-Fluoro-phenyl)-5-methyl-oxazol-4-yl]-ethylamino}-acetyl)-pyrrolidine-2-carbonitrile, (2S)-1-({2-[2-(4-Benxyloxy-phenyl)-5-methyl-oxazol-4-yl]-ethylamino}-acetyl)-pyrrolidine-2-carbonitrile, (2S)-1-{[1,1-Dimethyl-2-(5-methyl-2-phenyl-oxazol-4-yl)-ethylamino]-acetyl}-pyrrolidifle-2-carbonitrile, and pharmaceutically acceptable salts thereof.

7. A compound according to claim 1, selected from the group consisting of (2S)-1-{[1,1-Dimethyl-3-(2-methyl-4-pyridin-3-yl-imidazol-1-yl)-propylamino}-acetyl}-pyrrolidine-2-carbonitrile, (2S) 1-{[1,1-Dimethyl-3-(4-pyridin-3-yl-imidazol-1-yl)-propylamino]-acetyl}-pyrrolidine-2-carbonitrile, and pharmaceutically acceptable salts thereof.

8. A pharmaceutical composition comprising:
a compound of formula (I)

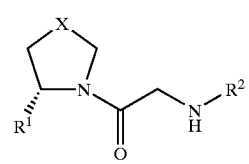

(I)

wherein

R$^1$ is CN,

R$^2$ is —C(R$^3$,R$^4$)—(CH$_2$)$_n$—R$^5$,

R$^3$ is hydrogen, lower-alkyl, benzyl, or hydroxybenzyl,

R$^4$ is hydrogen or lower-alkyl,

R$^5$ is oxazolyl or imidazolyl which can be unsubstituted or substituted with 1 to 3 substituents independently selected from the group consisting of lower-alkyl, lower-alkoxy, halogen, CN, CF$_3$, trifluoroacetyl, pyridinyl and phenyl, which pyridinyl can be unsubstituted or substituted with 1 to 3 substituents independently selected from the group consisting of lower-alkyl, lower-alkoxy, halogen, and CF$_3$, and which phepyl can be unsubstituted or substituted with 1 to 3 substituents independently selected from the group consisting of lower-alkyl, lower-alkoxy, benzyloxy, halogen, CF$_3$, CF$_3$—O, CN and NH—CO—lower-alkyl, X is C(R$^8$,R$^9$), R$^8$ and R$^9$ independently from each other are H or lower-alkyl, n is 0,1 or 2, or a pharmaceutically acceptable salt thereof; and a pharmaceutically acceptable carrier.

* * * * *

UNITED STATES PATENT AND TRADEMARK OFFICE
CERTIFICATE OF CORRECTION

PATENT NO. : 6,861,440 B2
DATED : March 1, 2005
INVENTOR(S) : Markus Boehringer et al.

It is certified that error appears in the above-identified patent and that said Letters Patent is hereby corrected as shown below:

<u>Column 102,</u>
Line 50, "...selected from the aroup..." should be -- ...selected from the group... --

<u>Column 104,</u>
Line 6, "...acetyl}-pyrrolidifle..." should be -- ...acetyl}-pyrrolidine... --
Line 11, "...-propylamino}-..." should be -- ...-propylamino]-... --
Line 42, "phepyl..." should be -- phenyl --

Signed and Sealed this

Thirty-first Day of May, 2005

JON W. DUDAS
*Director of the United States Patent and Trademark Office*